(12) United States Patent
Thielen et al.

(10) Patent No.: US 7,125,719 B2
(45) Date of Patent: Oct. 24, 2006

(54) ION TRANSPORTER STRESS-RELATED POLYPEPTIDES AND METHODS OF USE IN PLANTS

(75) Inventors: Nocha Van Thielen, Chapel Hill, NC (US); Oswaldo da Costa e Silva, Rheinland-Pfalz (DE); Ruoying Chen, Apex, NC (US)

(73) Assignee: BASF Plant Science GmbH, Ludwigshafen (DE)

( * ) Notice: Subject to any disclaimer, the term of this patent is extended or adjusted under 35 U.S.C. 154(b) by 615 days.

(21) Appl. No.: 10/335,592

(22) Filed: Dec. 31, 2002

(65) Prior Publication Data

US 2003/0163850 A1    Aug. 28, 2003

Related U.S. Application Data

(60) Provisional application No. 60/345,816, filed on Dec. 31, 2001.

(51) Int. Cl.
 A01H 5/00   (2006.01)
 C12N 15/82  (2006.01)
 C12N 15/87  (2006.01)
 C12N 5/14   (2006.01)
 C12P 21/04  (2006.01)

(52) U.S. Cl. .................. 435/468; 435/320.1; 435/419; 800/281; 800/289; 536/23.6

(58) Field of Classification Search ........ 800/278–289; 435/320.1, 419, 468; 536/23.6
See application file for complete search history.

(56) References Cited

U.S. PATENT DOCUMENTS 5,608,145 A    3/1997    Schroeder et al.

FOREIGN PATENT DOCUMENTS

AU    5016499    4/2000
JP    11187878   7/1999

OTHER PUBLICATIONS

Keskin et al., Protein Science, 13:1043-1055, 2004.*
Thornton et al., Nature structural Biology, structural genomics supplement, pp. 991-994, Nov. 2000.*
Guo et al., PNAS, 101: 9205-9210, 2004.*
Grotz, et al, "Identification of a Family of Zinc Transporter Genes from Arabidopsis that Respond to Zinc Deficiency," 1998, Proc. Natl. Acad. Sci, 195:7220-7224.
Rubio et al, "Sodium-driven Potassium Uptake by the Plant Transporter HKT1 and Mutations Conferring Salt Tolerance," 1995 Science, 270:1660-1663.
Su et al., "The Expression of HAK-Type K +Transporters is Regulated in Response to Salinity Stress Common Ice Plant," 2002, Plant Physiol. 129:1482-1493.

Bohnert et al., "Strategies for engineering water-stress tolerance in plants", 1996, *Trends in Biotech.*, 14:89-97.
Ehret et al., "Potassium Loss from Stomatal Guard Cells at Low Water Potentials", 1979, *J. Exper. Bot.*, 30:225-234.
Fairbairn, D.J. et al., "Characterisation of two distinct HKT1-like potassium transporters from *Eucalyptus camaldulensis*", 2000, *Plant Molec. Biol.* 43:515-25.
Gaymard, F. et al., "Identification and Disruption of a Plant Shaker-like Outward Channel Involved in K+ Release into the Xylem Sap", 1998, *Cell*, 94:647-55.
Hirsch et al., "A Role for the AKT1 Potassium Channel in Plant Nutrition", 1998, *Science*, 280:918-921.
Hirsch, et al., "Improving nutrient capture from soil by the genetic manipulation of crop plants", 1999, *Trends in Biotech.*, 17:356-361.
Ichida, A.M. et al., "Expression of a Cs+-Resistant Guard Cell K+ Channel Confers Cs+-Resistant, Light-Induced Stomatal Opening in Transgenic Arabidopsis", 1997, *The Plant Cell*, 9:1843-57.
Machuka, Jesse, et al., "Sequence analysis of Expressed Sequence Tags from an ABA-Treated cDNA Library Identifies Stress Response Genes in the Moss *Physcomitrella patens*", 1999, *Plant Cell Physiol.*, 40(4), pp. 378-387.
Munns et al., "Solute Accumulation in the Apex and Leaves of Wheat during Water Stress", 1979, *Aust. J. Plant Physiol.*, 6:379-389.
Pastore, D. et al., "The Existence of the K+ Channel in Plant Mitochondria", 1999, *Journal of Biolog. Chem.*, 274(38):26683-90.
Quarrie SA, "New molecular tools to improve the efficiency of breeding for increased drought resistance", 1996, *Plant Growth Reg.*, 20:167-178.
Roberts, S.K., "Regulation of K + Channels in Maize Roots by Water Stress and Abscisic Acid", 1998, *Plant Physiol.*, 116:145-53.
Ros R. et al., "Molecular determinants of the *Arabidopsis* AKT1 K+ channel ionic selectivity investigated by expression in yeast of randomly mutated channels", 1999, *Physiologia Plantarum*, 105:459-68.
Serrano, R., "Salt Tolerance in Plants and Microorganisms: Toxicity Targets and Defense Responses", 1996, *Int'l Review of Cytology*, 165:1-52.
Smirnoff, N., "Plant resistance to environmental stress", 1998, *Curr. Opin. Biotech.*, 9(2):214-219.
Terry et al., "Effects of Potassium Deficiency on the Photosynthesis and Respiration of Leaves of Sugar Beet", 1973, *Plant Physiol.*, 51:783-786.
Zhu, J.-K. et al., "Genetic Analysis of Salt Tolerance in Arabidopsis: Evidence for a Critical Role of Potassium Nutrition", 1998, *The Plant Cell*, 10:1181-91.

* cited by examiner

Primary Examiner—Ashwin Mehta
Assistant Examiner—Vinod Kumar
(74) Attorney, Agent, or Firm—Ruoying Chen; Mark Westhafer

(57) ABSTRACT

A transgenic plant transformed by an Ion Transporter Stress-Related Polypeptide (ITSRP) coding nucleic acid, wherein expression of the nucleic acid sequence in the plant results in increased tolerance to environmental stress as compared to a wild type variety of the plant. Also provided are agricultural products, including seeds, produced by the transgenic plants. Also provided are isolated ITSRPs, and isolated nucleic acid coding ITSRPs, and vectors and host cells containing the latter.

30 Claims, 2 Drawing Sheets

SEQUENCE LISTING

<160> NUMBER OF SEQ ID NOS: 34

<210> SEQ ID NO 1
<211> LENGTH: 697
<212> TYPE: DNA
<213> ORGANISM: Physcomitrella patens

<400> SEQUENCE: 1

```
gcacgagcag atgaaggctg agtcacttcg gaagtgcagt gatcgtctct gtttctgagg      60
aatatttatc gtacagtgct cgttttgttg aactcgtctt tatgtcttgg tcgcgaagcc     120
ttccgtgacg cggatttgat agcagttttg cagctcactg ggtaggagcg ttcttcacgc     180
tcatggtttc agtttggatg ttgtcgctgg ctttagattg cctttggacg atgactcaat     240
tcggtgaaaa ttcgataagt tgcgtttcgt agtgagcagt ctcccagagg aatctgccat     300
tgtgtagcga ggtgtaggat catggggtgg tcggtaagcg ggttgaccca caaggtcctt     360
ggagcagtgg ggctgatgaa gtacggcaat cagcgcaagg cctctacccc agcatcttc      420
agccatgcat acagcagcgg aatgttgccg gctcttggat ccaaccagag tacgaagaac     480
gtccttcaaa agaaatacgt tattcatcct acaacaaga attacaggta ctggcagggg      540
attttggtgg tgctagtgtt ttactccgca tgggtgtcac ctttcgagtt tgggttcgtg     600
caaaatcctc gcggtgctct gttaactgtc gacaatattg tcaactttct cttcttcatc     660
gacatcgtat tgaccttctt cgtcgcgtat ctcgaca                              697
```

<210> SEQ ID NO 2
<211> LENGTH: 3020
<212> TYPE: DNA
<213> ORGANISM: Physcomitrella patens

<400> SEQUENCE: 2

```
gaattcgccc ttatcccggg cgtttcgtag tgagcagtct cccagaggaa tctgccattg      60
tgtagcgagg tgtaggatca tggggtggtc ggtaagcggg ttgacccaca aggtccttgg     120
agcagtgggg ctgatgaagt acggcaatca gcgcaaggcc tctaccccca gcatcttcag     180
ccatgcatac agcagcggaa tgttgccggc tcttggatcc aaccagagta cgaagaacgt     240
ccttcaaaag aaatacgtta ttcatcctta caacaagaat tacaggtact ggcagggat     300
tttggtggtg ctagtgtttt actccgcatg gtgtcaccct ttcgagttg gttcgtgca      360
aaatcctcgc ggtgctctgt taactgtcga caatattgtc aactttctct tcttcatcga     420
catcgtattg accttcttcg tcgcgtatct cgacacctca acttttttga tggaagacaa     480
cttgaagaag atcgccatca ggtatttgag aacatggttt attttggatg ttgtgtcgac     540
tgttccattg gccgcagtaa tagcgatttt cactggaaaa tatgagacag ggtttgcggc     600
cagttttgtc aatttgttgc gcctctggcg attgcgccgt gtgagtgacg tgtttgcgag     660
ggtggagaag aatgtgaaat ttagttactt ctggactcga tgcctcaaac tctttctggt     720
gactgtgttt gtttgccact tgcggcctg ctcgtactac ttattggctg ctcgacatcc     780
ggcaagcaaa gaggcagata cgtggctagg agctgtgctc ccaaatttta aagaggagtc     840
actgtgggcg cggtacgtga cgagtatgta ctggtccatc actacactgg cgactgtggg     900
atatggcgat ttgcatccag tcaaccgtgg tgaaatgatc ttcaccatcc tttacatgtt     960
gctgaatctg gcattgactg cgtacatcat aggaaacatg accaatctca tcactcgtct    1020
taccgcacga actcgtgact atcgtgactc ggtgcaacaa ttggtggagt ttgcaactag    1080
```

-continued

```
aaatcagttg ccacgcaagc ttcacgagca aatgatctcc cacgtgcagc tcaagttcaa   1140
gacagagagc cttcagcatc aagggaccat agccacccta ccaaaggcta tccgctcatc   1200
tgttgcgcaa tttctgtttt taacacagt cgagaaagtg tacctttttcc aaggcacttc   1260 ttacaatttt cgtactcagc tggtgtcgga gatgaaggtc gagttcttcc ctcctcgcga   1320
ggaaattatt ctggttaacg aggcccctc cgagttttac atagttgtga atggttccgc    1380
ggatgtaata attcgaaggg aggaagccgg atcagagcaa attctaatga cggctcaggc   1440
aactgatgta attggcgaga tagggtgat ttgttacagg ccacagcctt tcactgtgcg    1500
aagtcgaaag ttatcccagc tcttgcgact tgaccgcatt gtgtttatga acattgtgca   1560
acaatacaag gaagacggcc agaagattgt tgacaatctg ttgcagcgct tgcgagaagc   1620
ctatgatcct cgatttgagg agctttcctc tgagattgaa gccctccttg ttgaaggcgg   1680
cgaaatatcg gaaccaagcg tatgtgcggt tgctgccgga ggaaatgtgg aggttatgca   1740
gcagctgttg agcaaaggcg cggaggtgga caagacagat tatcacggtc ggactgctct   1800
ggtcattgca tcatcaaaag gttacgagga gtgcgtcaag ctccttctgg aacacggagc   1860
tgaccccaac aaggctgatg tgtatgggaa ggttcctcta cttgaggccc ttattgcccg   1920
cgacacggct accgtgaagc tcttatcaga aacggggcg accttgaaaa atgcggacat    1980
gggggtatac ctcgggcaag ctgtgctcga ctgtaatcga gacctcattg acgactactt   2040
aaaatatgga accgacataa acacagcagg cgaatctgaa ggactgagtg cgctccacat   2100
tgctgttatt gatggcaaca tggatatggt gaggttttta gtatcccgag agccgaccc    2160 tcacatcaag cctggtgatg aggccaccct taccgcatac gagctagctg agagaagtgc   2220
agatcacccc gaaatagctt cctttttgaa ggcccaatca gtccgcgatg aaccatacag   2280
ttccatcacg cctagagagt cgacatctaa cgcaaatcag aagaggcttc caaggaaggg   2340
aagctccaat gttgaattcc agattgatga ggtaacaccc ccgcctagtc caaataaagg   2400
atttccggga gagcgaacga tacactcatt aatgcgaaag cagtcggctc ggggccgtct   2460
catgactata agaggacaga aaaccctcag ccggcaacta aacgcaaacc agaaccccttc  2520 aggttgggc ttgagacggc gtgacaatcg agaccctctt cagactttc catcagctgg     2580 cgctgctaag gaggttcctc ttcgtgtcat catccattct tatcatcctt ggaacaagga   2640
agcggtggga cttggaaagg tcgtttttgct gccgaaaact attgaagagg ttctcaagat   2700
tgcgaacgag aaattcaaca atcatccaac gaaggtgttg aacaaagagg cagctgagat   2760
tgacgacttg agtgtcatcc gagaaaacga caacttgtat gtcattaacg attcagagaa   2820
gttgaacacg agttcccccc cagggatgga cacagatgac ctcatagcaa gattgcaagc   2880
aatagtcaca gcattgtctc aacccaaacc atagactcat gcatgcgacc aaggttgggt   2940
atgtacttct cataagctta ggactcgact aggatatca cgagatcagc gacagtgtct    3000
gagctcgcaa gggcgaattc                                               3020
```

<210> SEQ ID NO 3
<211> LENGTH: 944
<212> TYPE: PRT
<213> ORGANISM: Physcomitrella patens

<400> SEQUENCE: 3

Met Gly Trp Ser Val Ser Gly Leu Thr His Lys Val Leu Gly Ala Val
1               5                   10                  15

Gly Leu Met Lys Tyr Gly Asn Gln Arg Lys Ala Ser Thr Pro Ser Ile

-continued

```
                    20                  25                  30
Phe Ser His Ala Tyr Ser Ser Gly Met Leu Pro Ala Leu Gly Ser Asn
            35                  40                  45

Gln Ser Thr Lys Asn Val Leu Gln Lys Lys Tyr Val Ile His Pro Tyr
        50                  55                  60

Asn Lys Asn Tyr Arg Tyr Trp Gln Gly Ile Leu Val Leu Val Phe
65                  70                  75                  80

Tyr Ser Ala Trp Val Ser Pro Phe Glu Phe Gly Phe Val Gln Asn Pro
                    85                  90                  95

Arg Gly Ala Leu Leu Thr Val Asp Asn Ile Val Asn Phe Leu Phe Phe
                100                 105                 110

Ile Asp Ile Val Leu Thr Phe Phe Val Ala Tyr Leu Asp Thr Ser Thr
            115                 120                 125

Phe Leu Met Glu Asp Asn Leu Lys Lys Ile Ala Ile Arg Tyr Leu Arg
        130                 135                 140

Thr Trp Phe Ile Leu Asp Val Val Ser Thr Val Pro Leu Ala Ala Val
145                 150                 155                 160

Ile Ala Ile Phe Thr Gly Lys Tyr Glu Thr Gly Phe Ala Ala Ser Phe
                    165                 170                 175

Val Asn Leu Leu Arg Leu Trp Arg Leu Arg Arg Val Ser Asp Val Phe
                180                 185                 190

Ala Arg Val Glu Lys Asn Val Lys Phe Ser Tyr Phe Trp Thr Arg Cys
            195                 200                 205

Leu Lys Leu Phe Leu Val Thr Val Phe Val Cys His Phe Ala Ala Cys
        210                 215                 220

Ser Tyr Tyr Leu Leu Ala Ala Arg His Pro Ala Ser Lys Glu Ala Asp
225                 230                 235                 240

Thr Trp Leu Gly Ala Val Leu Pro Asn Phe Lys Glu Ser Leu Trp
                    245                 250                 255

Ala Arg Tyr Val Thr Ser Met Tyr Trp Ser Ile Thr Thr Leu Ala Thr
                260                 265                 270

Val Gly Tyr Gly Asp Leu His Pro Val Asn Arg Gly Glu Met Ile Phe
            275                 280                 285

Thr Ile Leu Tyr Met Leu Leu Asn Leu Ala Leu Thr Ala Tyr Ile Ile
        290                 295                 300

Gly Asn Met Thr Asn Leu Ile Thr Arg Leu Thr Ala Arg Thr Arg Asp
305                 310                 315                 320

Tyr Arg Asp Ser Val Gln Gln Leu Val Glu Phe Ala Thr Arg Asn Gln
                    325                 330                 335

Leu Pro Arg Lys Leu His Glu Gln Met Ile Ser His Val Gln Leu Lys
                340                 345                 350

Phe Lys Thr Glu Ser Leu Gln His Gln Gly Thr Ile Ala Thr Leu Pro
            355                 360                 365

Lys Ala Ile Arg Ser Ser Val Ala Gln Phe Leu Phe Phe Asn Thr Val
        370                 375                 380

Glu Lys Val Tyr Leu Phe Gln Gly Thr Ser Tyr Asn Phe Arg Thr Gln
385                 390                 395                 400

Leu Val Ser Glu Met Lys Val Glu Phe Phe Pro Pro Arg Glu Ile
                    405                 410                 415

Ile Leu Val Asn Glu Ala Pro Ser Glu Phe Tyr Ile Val Val Asn Gly
                420                 425                 430

Ser Ala Asp Val Ile Ile Arg Arg Glu Glu Ala Gly Ser Glu Gln Ile
            435                 440                 445
```

-continued

```
Leu Met Thr Ala Gln Ala Thr Asp Val Ile Gly Glu Ile Gly Val Ile
    450                 455                 460
Cys Tyr Arg Pro Gln Pro Phe Thr Val Arg Ser Arg Lys Leu Ser Gln
465                 470                 475                 480
Leu Leu Arg Leu Asp Arg Ile Val Phe Met Asn Ile Val Gln Gln Tyr
                485                 490                 495
Lys Glu Asp Gly Gln Lys Ile Val Asp Asn Leu Leu Gln Arg Leu Arg
            500                 505                 510
Glu Ala Tyr Asp Pro Arg Phe Glu Glu Leu Ser Ser Glu Ile Glu Ala
        515                 520                 525
Leu Leu Val Glu Gly Gly Glu Ile Ser Glu Pro Ser Val Cys Ala Val
    530                 535                 540
Ala Ala Gly Gly Asn Val Glu Val Met Gln Gln Leu Leu Ser Lys Gly
545                 550                 555                 560
Ala Glu Val Asp Lys Thr Asp Tyr His Gly Arg Thr Ala Leu Val Ile
                565                 570                 575
Ala Ser Ser Lys Gly Tyr Glu Glu Cys Val Lys Leu Leu Leu Glu His
            580                 585                 590
Gly Ala Asp Pro Asn Lys Ala Asp Val Tyr Gly Lys Val Pro Leu Leu
        595                 600                 605
Glu Ala Leu Ile Ala Arg Asp Thr Ala Thr Val Lys Leu Leu Ser Glu
    610                 615                 620
Asn Gly Ala Thr Leu Lys Asn Ala Asp Met Gly Val Tyr Leu Gly Gln
625                 630                 635                 640
Ala Val Leu Asp Cys Asn Arg Asp Leu Ile Asp Asp Tyr Leu Lys Tyr
                645                 650                 655
Gly Thr Asp Ile Asn Thr Ala Gly Glu Ser Glu Gly Leu Ser Ala Leu
            660                 665                 670
His Ile Ala Val Ile Asp Gly Asn Met Asp Met Val Arg Phe Leu Val
        675                 680                 685
Ser Arg Gly Ala Asp Pro His Ile Lys Pro Gly Asp Glu Ala Thr Leu
    690                 695                 700
Thr Ala Tyr Glu Leu Ala Glu Arg Ser Ala Asp His Pro Glu Ile Ala
705                 710                 715                 720
Ser Phe Leu Lys Ala Gln Ser Val Arg Asp Glu Pro Tyr Ser Ser Ile
                725                 730                 735
Thr Pro Arg Glu Ser Thr Ser Asn Ala Asn Gln Lys Arg Leu Pro Arg
            740                 745                 750
Lys Gly Ser Ser Asn Val Glu Phe Gln Ile Asp Glu Val Thr Pro Pro
        755                 760                 765
Pro Ser Pro Asn Lys Gly Phe Ser Gly Glu Arg Thr Ile His Ser Leu
    770                 775                 780
Met Arg Lys Gln Ser Ala Arg Gly Arg Leu Met Thr Ile Arg Gly Gln
785                 790                 795                 800
Lys Thr Leu Ser Arg Gln Leu Asn Ala Asn Gln Asn Pro Ser Gly Trp
                805                 810                 815
Gly Leu Arg Arg Arg Asp Asn Arg Asp Pro Leu Gln Thr Phe Pro Ser
            820                 825                 830
Ala Gly Ala Ala Lys Glu Val Pro Leu Arg Val Ile Ile His Ser Tyr
        835                 840                 845
His Pro Trp Asn Lys Glu Ala Val Gly Leu Gly Lys Val Val Leu Leu
    850                 855                 860
```

```
Pro Lys Thr Ile Glu Glu Val Leu Lys Ile Ala Asn Glu Lys Phe Asn
865                 870                 875                 880

Asn His Pro Thr Lys Val Leu Asn Lys Glu Ala Ala Glu Ile Asp Asp
                885                 890                 895

Leu Ser Val Ile Arg Glu Asn Asp Asn Leu Tyr Val Ile Asn Asp Ser
            900                 905                 910

Glu Lys Leu Asn Thr Ser Ser Pro Pro Gly Met Asp Thr Asp Asp Leu
        915                 920                 925

Ile Ala Arg Leu Gln Ala Ile Val Thr Ala Leu Ser Gln Pro Lys Pro
    930                 935                 940

<210> SEQ ID NO 4
<211> LENGTH: 999
<212> TYPE: DNA
<213> ORGANISM: Physcomitrella patens

<400> SEQUENCE: 4
gctacttcaa atgatgcgtg ggatggattg actgtatgct tcggtcgatc gagtcctctc    60
aacgaatcca agaattgttc gtcgtcaaaa gaacaattat gccgttggaa cgggattgga   120
actctcagac gtaatactcc atgcccacct tcagcaacct gtctttaggg atgcttaagt   180
acagcgtgtt gttgcggcag ttccgtcgca aaaacttgta atcttattg atgatgatgc    240 gtttaggaaa ccacgagtcg ctcttggcgt ggatgtcact gtcgccaagc acgtacacga   300
cgcctgcttc tctggccttc tgcaagaaca gaacttcctc gttggtgtaa gcttcttgat   360
cggcttccag ctcatccaca gtctttgcgc cgatgtctga cccacaggag tcgttcgaaa   420
ccgacgactc gcagggccta tctaatttgt gatggctagg agaggcggca tgggaggagg   480
ccagccctga ttcaggagtg acttccgccg cttccgttct gatgaacctt tccaggctcg   540
caaggagcat gttttcaaag gtctggccgt ctgattcagc ccatccaca tgatctgtgt    600 agccgtagcg aactgcacaa cggaacatgc ggtagtttct gggaccgagc tgcggataa    660 ggattcgctc atcttcgggg acggtgctga cagagatgtg gcggatgcag acgaacacta   720
gagtggagtg gatagcaggg agattcgaga tgaagtggcg aaatattgct ggaactccct   780
gcggaagctc agtgtatacg agcccgactc ccggaactcg agagattcct aggctatggc   840
caagagacag aacccagtcc aaggaaatct tatgagagac ctcatacaag cgtttcatcc   900
tggtgccgaa gttccacgag tacatgatcg tgaggaagca tgcggcgata acgaggggaa   960
cccatccgcc ctgcgtcacc ttggagagca ccctggtgc                         999

<210> SEQ ID NO 5
<211> LENGTH: 2553
<212> TYPE: DNA
<213> ORGANISM: Physcomitrella patens

<400> SEQUENCE: 5
atcccgggcg tcgcgtttac gtgtgttcac cgtatatctg gtcaattctt gatcatggag    60
acgtcggcgg ttgaattgca aatgtctaca gacgcagtcc atcagagaga aactggagag   120
agacctccat tagaacaaac tgcgcaagat gaagagacca gtcgggaggc cttgcacgcg   180
gatgaggctg cctatcgaga gaaggaaggt ccctttcgac ggttgtcgcg gaagctcacg   240
cggcccgatt cccttgacgt ggagtccatg cgagtgaaag aaatggacca tgctgcacct   300
gtagcatcgt tttcgttcat tctgaagctg gcgtatcaga gcatcggggt ggtgtatggt   360
gatctgggta cgtccccgct ctacgtgtac agtagcactt tcacaagcgg catcaaaacg   420
```

| | |
|---|---|
| aacgacgaca ttctgggcgt tctctgtctc atcatctaca ccatcattgc cactccgctc | 480 |
| gtcaagtaca tctttatcgt ccttcgggca aacgacaatg gcgaaggggg tacatttgcg | 540 |
| ttgtattcat tgatttgtcg acacgttaag ctgagcgggg ctcacgcgca gcagcccaca | 600 |
| gacttgaaca tttcaagcta caagctggag acaccgtcca cgaagatggc tagggcgacg | 660 |
| cgcattaagg aggcgcttga gaaaagcaga gcttggcaga atgtcctgct tctgattgtt | 720 |
| ctgttagggc cttgcttggt catcggcgat gggtccctaa cgcccgccat ctcagttcta | 780 |
| tcggccattc agggtatcag cgtgaacgtt agtggccttt ctcccaatgt gtcggtgatt | 840 |
| atcacggtcg ttgtattggc agccctcttc agccttcagc gatttggcac tcacagggtg | 900 |
| gctttcttgt tcggaccagc gatgttggct tggttcttct ccatcggcat catagggctg | 960 |
| tacaacattt tcagatggga tccttcggtg ttcaaggctc tcaatccttg gtatggactt | 1020 |
| aattacttca tcagaaacaa agtagacgct tgggcttccc tcggaggtat cgttctctgc | 1080 |
| attacaggaa gcgaggcgat gtttgcagat ttgggccatt ttactgtcaa gtcaatgcag | 1140 |
| gttgccttca cattcttggt gttcccgtct ctcctatgtg catacatcgg ccaggcttca | 1200 |
| tttcttatga agaatcagct tgatgacgat gtggcctaca cattctaccg ctccgttcca | 1260 |
| aagcctattt actggcccat gttcggggtc gctacatgcg cggcgatcat cgccagtcaa | 1320 |
| gctatgattt cagcgacata ctcgatgatc agaaatgcca tgtccctggg ttgcttcccg | 1380 |
| cgtgtcacca tagttcacac tctaagaaag gtgcacggcc agatttacat tccggagatc | 1440 |
| aattggatca tcatggtgtt gagtatcacc atcgtcggag ggttccgcag caccactcaa | 1500 |
| atcggccacg cctacgggat tgcggtagtg ggggtgtttt tcatctccac gtgcctcctc | 1560 |
| acgctcatca tgctcatgat ctggcagaca aatattttcc tgtgcgcctt gttctttacc | 1620 |
| gtcttcttta tcatcgaggg aatttatttc tcagcggtgc tctccaaggt gacgcagggc | 1680 |
| ggatgggttc ccctcgttat cgccgcatgc ttcctcacga tcatgtactc gtggaacttc | 1740 |
| ggcaccagga tgaaacgctt gtatgaggtc tctcataaga tttccttgga ctgggttctg | 1800 |
| tctcttggcc atagcctagg aatctctcga gttccgggag tcgggctcgt atacactgag | 1860 |
| cttccgcagg gagttccagc aatatttcgc cacttcatct cgaatctccc tgctatccac | 1920 |
| tccactctag tgttcgtctg catccgccac atctctgtca gcaccgtccc cgaagatgag | 1980 |
| cgaatcctta tccgcaggct cggtcccaga aactaccgca tgttccgttg tgcagttcgc | 2040 |
| tacggctaca cagatcatgt ggatggggct gaatcagacg gccagacctt tgaaaacatg | 2100 |
| ctccttgcga gcctggaaag gttcatcaga acggaagcgg cggaagtcac tcctgaatca | 2160 |
| gggctggcct cctcccatgc cgcctctcct agccatcaca aattagatag gccctgcgag | 2220 |
| tcgtcggttt cgaacgactc ctgtgggtca gacatcggcg caaagactgt ggatgagctg | 2280 |
| gaagccgatc aagaagctta caccaacgag gaagttctgt tcttgcagaa ggccagagaa | 2340 |
| gcaggcgtcg tgtacgtgct tggcgacagt gacatccacg ccaagagcga ctcgtggttt | 2400 |
| cctaaacgca tcatcatcaa taagatttac aagtttttgc gacggaactg ccgcaacaac | 2460 |
| acgctgtact taagcatccc taaagacagg ttgctgaagg tgggcatgga gtattacgtc | 2520 |
| tgagagttcc aatcccgttc caacggagct cgc | 2553 |

<210> SEQ ID NO 6
<211> LENGTH: 822
<212> TYPE: PRT
<213> ORGANISM: Physcomitrella patens

<400> SEQUENCE: 6

```
Met Glu Thr Ser Ala Val Glu Leu Gln Met Ser Thr Asp Ala Val His
 1               5                  10                  15

Gln Arg Glu Thr Gly Glu Arg Pro Leu Glu Gln Thr Ala Gln Asp
            20                  25                  30

Glu Glu Thr Ser Arg Glu Ala Leu His Ala Asp Glu Ala Ala Tyr Arg
             35                  40                  45

Glu Lys Glu Gly Pro Phe Arg Arg Leu Ser Arg Lys Leu Thr Arg Pro
 50                  55                  60

Asp Ser Leu Asp Val Glu Ser Met Arg Val Lys Glu Met Asp His Ala
 65              70                  75                  80

Ala Pro Val Ala Ser Phe Ser Phe Ile Leu Lys Leu Ala Tyr Gln Ser
                 85                  90                  95

Ile Gly Val Val Tyr Gly Asp Leu Gly Thr Ser Pro Leu Tyr Val Tyr
                100                 105                 110

Ser Ser Thr Phe Thr Ser Gly Ile Lys Thr Asn Asp Asp Ile Leu Gly
            115                 120                 125

Val Leu Cys Leu Ile Ile Tyr Thr Ile Ile Ala Thr Pro Leu Val Lys
    130                 135                 140

Tyr Ile Phe Ile Val Leu Arg Ala Asn Asp Asn Gly Glu Gly Gly Thr
145                 150                 155                 160

Phe Ala Leu Tyr Ser Leu Ile Cys Arg His Val Lys Leu Ser Gly Ala
                165                 170                 175

His Ala Gln Gln Pro Thr Asp Leu Asn Ile Ser Ser Tyr Lys Leu Glu
            180                 185                 190

Thr Pro Ser Thr Lys Met Ala Arg Ala Thr Arg Ile Lys Glu Ala Leu
        195                 200                 205

Glu Lys Ser Arg Ala Trp Gln Asn Val Leu Leu Ile Val Leu Leu
    210                 215                 220

Gly Pro Cys Leu Val Ile Gly Asp Gly Ser Leu Thr Pro Ala Ile Ser
225                 230                 235                 240

Val Leu Ser Ala Ile Gln Gly Ile Ser Val Asn Val Ser Gly Leu Ser
                245                 250                 255

Pro Asn Val Ser Val Ile Ile Thr Val Val Leu Ala Ala Leu Phe
            260                 265                 270

Ser Leu Gln Arg Phe Gly Thr His Arg Val Ala Phe Leu Phe Gly Pro
        275                 280                 285

Ala Met Leu Ala Trp Phe Phe Ser Ile Gly Ile Ile Gly Leu Tyr Asn
    290                 295                 300

Ile Phe Arg Trp Asp Pro Ser Val Phe Lys Ala Leu Asn Pro Trp Tyr
305                 310                 315                 320

Gly Leu Asn Tyr Phe Ile Arg Asn Lys Val Asp Ala Trp Ala Ser Leu
                325                 330                 335

Gly Gly Ile Val Leu Cys Ile Thr Gly Ser Glu Ala Met Phe Ala Asp
            340                 345                 350

Leu Gly His Phe Thr Val Lys Ser Met Gln Val Ala Phe Thr Phe Leu
        355                 360                 365

Val Phe Pro Ser Leu Leu Cys Ala Tyr Ile Gly Gln Ala Ser Phe Leu
    370                 375                 380

Met Lys Asn Gln Leu Asp Asp Val Ala Tyr Thr Phe Tyr Arg Ser
385                 390                 395                 400

Val Pro Lys Pro Ile Tyr Trp Pro Met Phe Gly Val Ala Thr Cys Ala
                405                 410                 415
```

-continued

```
Ala Ile Ile Ala Ser Gln Ala Met Ile Ser Ala Thr Tyr Ser Met Ile
            420                 425                 430

Arg Asn Ala Met Ser Leu Gly Cys Phe Pro Arg Val Thr Ile Val His
            435                 440                 445

Thr Ser Lys Lys Val His Gly Gln Ile Tyr Ile Pro Glu Ile Asn Trp
            450                 455                 460

Ile Ile Met Val Leu Ser Ile Thr Ile Val Gly Gly Phe Arg Ser Thr
465                 470                 475                 480

Thr Gln Ile Gly His Ala Tyr Gly Ile Ala Val Val Gly Val Phe Phe
                485                 490                 495

Ile Ser Thr Cys Leu Leu Thr Leu Ile Met Leu Met Ile Trp Gln Thr
                500                 505                 510

Asn Ile Phe Leu Cys Ala Leu Phe Phe Thr Val Phe Phe Ile Ile Glu
            515                 520                 525

Gly Ile Tyr Phe Ser Ala Val Leu Ser Lys Val Thr Gln Gly Gly Trp
            530                 535                 540

Val Pro Leu Val Ile Ala Ala Cys Phe Leu Thr Ile Met Tyr Ser Trp
545                 550                 555                 560

Asn Phe Gly Thr Arg Met Lys Arg Leu Tyr Glu Val Ser His Lys Ile
                565                 570                 575

Ser Leu Asp Trp Val Leu Ser Leu Gly His Ser Leu Gly Ile Ser Arg
                580                 585                 590

Val Pro Gly Val Gly Leu Val Tyr Thr Glu Leu Pro Gln Gly Val Pro
            595                 600                 605

Ala Ile Phe Arg His Phe Ile Ser Asn Leu Pro Ala Ile His Ser Thr
            610                 615                 620

Leu Val Phe Val Cys Ile Arg His Ile Ser Val Ser Thr Val Pro Glu
625                 630                 635                 640

Asp Glu Arg Ile Leu Ile Arg Arg Leu Gly Pro Arg Asn Tyr Arg Met
                645                 650                 655

Phe Arg Cys Ala Val Arg Tyr Gly Tyr Thr Asp His Val Asp Gly Ala
                660                 665                 670

Glu Ser Asp Gly Gln Thr Phe Glu Asn Met Leu Leu Ala Ser Leu Glu
            675                 680                 685

Arg Phe Ile Arg Thr Glu Ala Ala Glu Val Thr Pro Glu Ser Gly Leu
            690                 695                 700

Ala Ser Ser His Ala Ala Ser Pro Ser His His Lys Leu Asp Arg Pro
705                 710                 715                 720

Cys Glu Ser Ser Val Ser Asn Asp Ser Cys Gly Ser Asp Ile Gly Ala
                725                 730                 735

Lys Thr Val Asp Glu Leu Glu Ala Asp Gln Glu Ala Tyr Thr Asn Glu
                740                 745                 750

Glu Val Leu Phe Leu Gln Lys Ala Arg Glu Ala Gly Val Val Tyr Val
            755                 760                 765

Leu Gly Asp Ser Asp Ile His Ala Lys Ser Asp Ser Trp Phe Pro Lys
            770                 775                 780

Arg Ile Ile Ile Asn Lys Ile Tyr Lys Phe Leu Arg Arg Asn Cys Arg
785                 790                 795                 800

Asn Asn Thr Leu Tyr Leu Ser Ile Pro Lys Asp Arg Leu Leu Lys Val
                805                 810                 815

Gly Met Glu Tyr Tyr Val
                820
```

<210> SEQ ID NO 7
<211> LENGTH: 879
<212> TYPE: DNA
<213> ORGANISM: Physcomitrella patens
<220> FEATURE:
<221> NAME/KEY: modified_base
<222> LOCATION: (728)
<223> OTHER INFORMATION: a, t, c, g, unknown or other
<220> FEATURE:
<221> NAME/KEY: modified_base
<222> LOCATION: (843)
<223> OTHER INFORMATION: a, t, c, g, unknown or other

<400> SEQUENCE: 7

```
gcacgaggcg atacaagaag gagtctattt ctctccagcg ttgagcattt ctgggcactg      60
catgtcgcac tggttgtcca cattgttgct gatgaaatga tgtctcccac ttgtagaagg     120
tctggttccg tgcgtgctcg ggtgaccaca ggaaactgcg ttgaaaggat tgggaagatt     180
gctcggtttg taacgctgtt attgattttt gctgtttgga tagagcttgc tgcggctcac     240
ggcggtgcag ctgatgaagc aacaccggaa gacggacctc cgccgaactt gcgggcgaag     300
ggcctgattc ttgtgaaggt gtattgcctg ataatcgtgt tttttgtgac gctgttgggt     360
ggaatctcgc cctacttcgt tccatggaac gcttcgtttt tggtgctggg aactcagtat     420
gccgcaggtg tatttctgac gactgcgttg ctacatttcc tgagcgacgc gcacaacatc     480
tttcaagcgc ttactaccaa acagtatgcg tttgcggaga tgcttgccat tgcaggctat     540
ttgatcacac tgtttggcga cctcatcatc cagcggctga tcctccgcgg tgctcgttcg     600
tctgcgcagc taggttcttt ggacggcgaa aaggatgggg ctgcgaatta tgatgagaagg    660
gtcgggccag aagtgaattg cgacgctgtt acatcgagct tcatttggag aatactctgt     720
ggtcatcngg gcctgtgttc cactctgtct tgaaggatgc cacgggtcag agaacagaa      780
catggaaact tggaatactt caaagattcc cgctgcggtt gcctgctgtg ccacgcctgt     840
gtnattgggc ccacacggtg tggtcatccc acggcgttc                            879
```

<210> SEQ ID NO 8
<211> LENGTH: 1462
<212> TYPE: DNA
<213> ORGANISM: Physcomitrella patens

<400> SEQUENCE: 8

```
tccacattgt tgctgatgaa atgatgtctc ccacttgtag aaggtctggt tccgtgcgtg      60
ctcgggtgac acaggaaac tgcgttgaaa ggattgggaa gattgctcgg tttgtaacgc      120
tgttattgat ttttgctgtt tggatagagc ttgctgcggc tcacggcggt gcagctgatg     180
aagcaacacc ggaagacgga cctccgccga acttgcgggc gaagggcctg attcttgtga     240
aggtgtattg cctgataatc gtgttttttg tgacgctgtt gggtggaatc tcgccctact     300
tcgttccatg gaacgcttcg tttttggtgc tgggaactca gtatgccgca ggtgtatttc     360
tgacgactgc gttgctacat ttcctgagcg acgcgcacaa catctttcaa gcgcttacta     420
ccaaacagta tgcgtttgcg gagatgcttg ccattgcagg ctatttgatc acactgtttg     480
gcgacctcat catccagcgg ctgatcctcc gcggtgctcg ttcgtctgcg cagctaggtt     540
ctttggacgg cgaaaaggat ggggctgcga aattagatga aagggtcggg cagaagtga      600
atgcgacgct gttacatcga gcttcatttg gagatactct gctgctcatt ctggccctgt     660
gtttccactc tgtctttgaa ggcattgcca tcggcgtttc agtgacgaag caggacgcat     720
ggaaagcctt ttggacaatt actcttcaca agtattcgc agccattgcc atgggtatcg     780
```

```
cactcttgcg catgctgcca aatcggccac tcctgtcgtg cttctgctat tcttttgcat    840
tcgccatctc cactccaatc ggtattgcaa tcggcatcat cattgatgcc actacagaag    900
gcgctgtggc agactggatt tatgcgattg ccatggggtt agccacggga gtgttcatct    960
atgtggccat caaccatctg cttggcaagg agtacatgcc ttccaaaact tctgtggaac   1020
agcccttcaa gaaattcatt gcccttacct tgggagctgc aaccatggct attgtcatga   1080
tctgggatgc ttgactttct atttcgcttg acttctattt cacttgataa gagacagttt   1140
aaccatcttc atagtggtgc atgttctcaa atattgtttc atgttcgctg tacagcgtgc   1200
tcagagggag agcatcactg gttattaggg cttttgcgat tcacatctga gtgttgacaa   1260
cttaggctcg aagtaccaaa caaggtagcc ggcagattgt cgtcaggttt tgtgcgttga   1320
tgcctttcct ggaatcgaag ccaattccag ttgattgaaa gattaaacag tttcctcaat   1380
ccatttaatg tattaaacaa atccacctta atatggaaaa tttgatctca atgaccaaag   1440
cggtgatgtt tttgagacca ag                                             1462
```

<210> SEQ ID NO 9
<211> LENGTH: 357
<212> TYPE: PRT
<213> ORGANISM: Physcomitrella patens

<400> SEQUENCE: 9

```
Met Met Ser Pro Thr Cys Arg Arg Ser Gly Ser Val Arg Ala Arg Val
 1               5                  10                  15

Thr Thr Gly Asn Cys Val Glu Arg Ile Gly Lys Ile Ala Arg Phe Val
            20                  25                  30

Thr Leu Leu Leu Ile Phe Ala Val Trp Ile Glu Leu Ala Ala Ala His
        35                  40                  45

Gly Gly Ala Ala Asp Glu Ala Thr Pro Glu Asp Gly Pro Pro Pro Asn
    50                  55                  60

Leu Arg Ala Lys Gly Leu Ile Leu Val Lys Val Tyr Cys Leu Ile Ile
65                  70                  75                  80

Val Phe Phe Val Thr Leu Leu Gly Gly Ile Ser Pro Tyr Phe Val Pro
                85                  90                  95

Trp Asn Ala Ser Phe Leu Val Leu Gly Thr Gln Tyr Ala Ala Gly Val
            100                 105                 110

Phe Leu Thr Thr Ala Leu Leu His Phe Leu Ser Asp Ala His Asn Ile
        115                 120                 125

Phe Gln Ala Leu Thr Thr Lys Gln Tyr Ala Phe Ala Glu Met Leu Ala
    130                 135                 140

Ile Ala Gly Tyr Leu Ile Thr Leu Phe Gly Asp Leu Ile Ile Gln Arg
145                 150                 155                 160

Leu Ile Leu Arg Gly Ala Arg Ser Ser Ala Gln Leu Gly Ser Leu Asp
                165                 170                 175

Gly Glu Lys Asp Gly Ala Ala Lys Leu Asp Glu Lys Gly Arg Ala Glu
            180                 185                 190

Val Asn Ala Thr Leu Leu His Arg Ala Ser Phe Gly Asp Thr Leu Leu
        195                 200                 205

Leu Ile Leu Ala Leu Cys Phe His Ser Val Phe Glu Gly Ile Ala Ile
    210                 215                 220

Gly Val Ser Val Thr Lys Gln Asp Ala Trp Lys Ala Phe Trp Thr Ile
225                 230                 235                 240

Thr Leu His Lys Val Phe Ala Ala Ile Ala Met Gly Ile Ala Leu Leu
                245                 250                 255
```

```
Arg Met Leu Pro Asn Arg Pro Leu Leu Ser Cys Phe Cys Tyr Ser Phe
            260                 265                 270

Ala Phe Ala Ile Ser Thr Pro Ile Gly Ile Ala Ile Gly Ile Ile Ile
            275                 280                 285

Asp Ala Thr Thr Glu Gly Ala Val Ala Asp Trp Ile Tyr Ala Ile Ala
            290                 295                 300

Met Gly Leu Ala Thr Gly Val Phe Ile Tyr Val Ala Ile Asn His Leu
305                 310                 315                 320

Leu Gly Lys Glu Tyr Met Pro Ser Lys Thr Ser Val Glu Gln Pro Phe
                325                 330                 335

Lys Lys Phe Ile Ala Leu Thr Leu Gly Ala Ala Thr Met Ala Ile Val
            340                 345                 350

Met Ile Trp Asp Ala
            355

<210> SEQ ID NO 10
<211> LENGTH: 2604
<212> TYPE: DNA
<213> ORGANISM: Brassica napus

<400> SEQUENCE: 10
```

| | | | | | |
|---|---|---|---|---|---|
| gcagctctta | cgacattccc | tctttaagca | ctttcctgtc | ttcttgaaaa | atctgtttgt | 60 |
| atttgtgaaa | agtttcacac | tttttattgtt | ttgcttgtaa | agatctgagc | tttatgagtt | 120 |
| aaaaaaaatg | gcggcaagag | tagaagcagc | aacaatgggt | ggtggtgaga | ttgatgaaga | 180 |
| gagtgatgag | agaggtagca | tgtgggattt | ggaccagaag | cttgatcaat | ctatggatga | 240 |
| agaagctggt | cggcttagga | acatgtacaa | agaaaagaaa | ttctctgctc | ttctgcttct | 300 |
| gcagctttcg | tttcagagcc | tcggtgttgt | gtatggagac | ttagggactt | ctcctctcta | 360 |
| tgttttctac | aatacattcc | ctcatgggat | caaagatcct | gaagatacca | ttggagctct | 420 |
| atctctcatt | atctattcac | tcacactcat | ccctctcctc | aaatacgttt | tcgttgtatg | 480 |
| taaagccaat | gacaatggtc | aaggtggaac | ctttgctctg | tattcattgc | tatgtagaca | 540 |
| tgccaaagtg | aaaacgataa | agaaccagca | ccgtaccgat | gaagagctta | ctacttacag | 600 |
| ccggtctacc | tttcatgagc | attcctttgc | tgccaaaacc | aaaaggtggt | tagaagacag | 660 |
| gacatctagg | aaaacagctc | ttcttgtttt | ggttcttgtt | ggtacttgta | tggtcattgg | 720 |
| tgatggtatc | cttactccag | ccatttctgt | tctgtcagct | gcaggtgggc | taagagtaaa | 780 |
| ccttcctcat | ataagcaatg | gtgttgttgt | tcttgttgct | gttgtgatac | tagtcagctt | 840 |
| gtttagcgta | cagcattacg | gaacagaccg | tgttggttgg | cttttcgctc | ccattgtctt | 900 |
| tctctggttt | ctctccattg | caagtatcgg | tatgtacaac | atctggaaac | acgacaccac | 960 |
| cgtcttgaaa | gctttctccc | ctgtgtatat | ctaccgttat | ttcaaaagag | gagtataga | 1020 |
| tcgctggaca | tctcttggag | gcatcatgct | tagtataaca | gggattgaag | cactcttcgc | 1080 |
| tgacctatct | cactttcctg | tttccgctgt | tcaaatagct | ttcactgcca | ttgtgtttcc | 1140 |
| ttgccttctc | ttggcttata | gtggacaagc | tgcctacatt | agaaaccacc | ctcatcacgt | 1200 |
| ggctgatgcg | ttttaccgtt | ccattccagg | aagtgtgtat | tggccaatgt | tcattattgc | 1260 |
| aactgctgca | gccattgttg | caagccaagc | acgatctca | gccacgttct | ctttgatcaa | 1320 |
| gcaagctcta | gcacacggtt | gtttccctag | ggttaaagta | gtccacactt | ctagaaagtt | 1380 |
| tcttggtcag | atctacgttc | cggacatcaa | ctggatcttg | atgatcctct | gcatcgccgt | 1440 |
| cacggctgga | ttcaagaacc | agagtcagat | aggtaacgct | tacggaacag | cagttgtgat | 1500 |

-continued

```
cgtcatgctt gtcacaactc tgcttatgac attgatcatg atcctagtgt ggcgttgcca      1560
ttgggttctt gttcttgtgt tcaccgtcct ctcgcttgtg gttgaatgca cttacttctc      1620
agccatgcta ttcaaagtgg accaaggagg ttgggttccg cttgttatcg ctgcagcgtt      1680
tctcctcatc atgtcggtat ggcattacgg aactttgaag aggtatgagt ttgagatgca      1740
tagtagagtc tcaatggctt ggattcttgg acttgggcct agccttgggc ttgttcgtgt      1800
tcctggtgtt gggcttgtct cactgagct agctagtgga gtccctcaca tcttctctca       1860
cttcattaca aacctaccgg ctattcactc tgttgtggtg tttgtatgcg tcaagaacct      1920
tccggtttac actgttcccg aggaagaacg gttccttgtt aaaggattg gtcctaaaaa       1980 acttccacat gttccgttgc gttgcaaggt atggatatgg agacttgcac aagaaagacg      2040
atgacttcaa aaacgtctc ttcgagagcc tcttcttgtt catacgactt gagtccatga       2100
tggaaggagg ctgttctgat tcagatgact acagcatatg tggaagccag aatcatttca      2160 aagaaagaa cgagaatgtt gcaacctttg atacgtttga ctctatagag tccataacgc       2220
cggtgaaacg ggtgagccac acggtgacgg cgtcgagcca gatgagcggt ggagtggatg      2280
agctggagtt tataaatagg tgtagagatg cgggagtggt gcatataatg gggaacacgg      2340
tggttagagc gaggaggcaa gcgaggttct acaagaagat agctattgat tatgtgtatg      2400
cgtttttgag gaagatttgt agagaacata gtgttatctt caatgttcct caggagagcc      2460
ttctgaatgt tggtcagatc ttctatgtat aagatatgag atatgtgtat gcactaatgc      2520
acggatgata ttgcatgtgt tgtatgtata tccctttttg aatgtaatgt tgtctatcat      2580
gttgtcaaaa aaaaaaaaaa aaaa                                             2604
```

<210> SEQ ID NO 11
<211> LENGTH: 638
<212> TYPE: PRT
<213> ORGANISM: Brassica napus

<400> SEQUENCE: 11

```
Met Ala Ala Arg Val Glu Ala Ala Thr Met Gly Gly Gly Glu Ile Asp
  1               5                  10                  15

Glu Glu Ser Asp Glu Arg Gly Ser Met Trp Asp Leu Asp Gln Lys Leu
             20                  25                  30

Asp Gln Ser Met Asp Glu Glu Ala Gly Arg Leu Arg Asn Met Tyr Lys
         35                  40                  45

Glu Lys Lys Phe Ser Ala Leu Leu Leu Gln Leu Ser Phe Gln Ser
     50                  55                  60

Leu Gly Val Val Tyr Gly Asp Leu Gly Thr Ser Pro Leu Tyr Val Phe
 65                  70                  75                  80

Tyr Asn Thr Phe Pro His Gly Ile Lys Asp Pro Glu Asp Thr Ile Gly
                 85                  90                  95

Ala Leu Ser Leu Ile Ile Tyr Ser Leu Thr Leu Ile Pro Leu Leu Lys
            100                 105                 110

Tyr Val Phe Val Val Cys Lys Ala Asn Asp Asn Gly Gln Gly Gly Thr
        115                 120                 125

Phe Ala Leu Tyr Ser Leu Leu Cys Arg His Ala Lys Val Lys Thr Ile
    130                 135                 140

Lys Asn Gln His Arg Thr Asp Glu Glu Leu Thr Thr Tyr Ser Arg Ser
145                 150                 155                 160

Thr Phe His Glu His Ser Phe Ala Ala Lys Thr Lys Arg Trp Leu Glu
                165                 170                 175
```

```
Asp Arg Thr Ser Arg Lys Thr Ala Leu Leu Val Leu Val Leu Val Gly
            180                 185                 190

Thr Cys Met Val Ile Gly Asp Gly Ile Leu Thr Pro Ala Ile Ser Val
        195                 200                 205

Leu Ser Ala Ala Gly Gly Leu Arg Val Asn Leu Pro His Ile Ser Asn
        210                 215                 220

Gly Val Val Val Leu Val Ala Val Val Ile Leu Val Ser Leu Phe Ser
225                 230                 235                 240

Val Gln His Tyr Gly Thr Asp Arg Val Gly Trp Leu Phe Ala Pro Ile
                245                 250                 255

Val Phe Leu Trp Phe Leu Ser Ile Ala Ser Ile Gly Met Tyr Asn Ile
                260                 265                 270

Trp Lys His Asp Thr Thr Val Leu Lys Ala Phe Ser Pro Val Tyr Ile
            275                 280                 285

Tyr Arg Tyr Phe Lys Arg Gly Gly Ile Asp Arg Trp Thr Ser Leu Gly
        290                 295                 300

Gly Ile Met Leu Ser Ile Thr Gly Ile Glu Ala Leu Phe Ala Asp Leu
305                 310                 315                 320

Ser His Phe Pro Val Ser Ala Val Gln Ile Ala Phe Thr Ala Ile Val
                325                 330                 335

Phe Pro Cys Leu Leu Leu Ala Tyr Ser Gly Gln Ala Ala Tyr Ile Arg
                340                 345                 350

Asn His Pro His His Val Ala Asp Ala Phe Tyr Arg Ser Ile Pro Gly
            355                 360                 365

Ser Val Tyr Trp Pro Met Phe Ile Ile Ala Thr Ala Ala Ile Val
        370                 375                 380

Ala Ser Gln Ala Thr Ile Ser Ala Thr Phe Ser Leu Ile Lys Gln Ala
385                 390                 395                 400

Leu Ala His Gly Cys Phe Pro Arg Val Lys Val Val His Thr Ser Arg
                405                 410                 415

Lys Phe Leu Gly Gln Ile Tyr Val Pro Asp Ile Asn Trp Ile Leu Met
            420                 425                 430

Ile Leu Cys Ile Ala Val Thr Ala Gly Phe Lys Asn Gln Ser Gln Ile
        435                 440                 445

Gly Asn Ala Tyr Gly Thr Ala Val Val Ile Val Met Leu Val Thr Thr
        450                 455                 460

Leu Leu Met Thr Leu Ile Met Ile Leu Val Trp Arg Cys His Trp Val
465                 470                 475                 480

Leu Val Leu Val Phe Thr Val Leu Ser Leu Val Val Glu Cys Thr Tyr
                485                 490                 495

Phe Ser Ala Met Leu Phe Lys Val Asp Gln Gly Gly Trp Val Pro Leu
            500                 505                 510

Val Ile Ala Ala Ala Phe Leu Leu Ile Met Ser Val Trp His Tyr Gly
            515                 520                 525

Thr Leu Lys Arg Tyr Glu Phe Glu Met His Ser Arg Val Ser Met Ala
        530                 535                 540

Trp Ile Leu Gly Leu Gly Pro Ser Leu Gly Leu Val Arg Val Pro Gly
545                 550                 555                 560

Val Gly Leu Val Tyr Thr Glu Leu Ala Ser Gly Val Pro His Ile Phe
                565                 570                 575

Ser His Phe Ile Thr Asn Leu Pro Ala Ile His Ser Val Val Phe
            580                 585                 590
```

```
Val Cys Val Lys Asn Leu Pro Val Tyr Thr Val Pro Glu Glu Glu Arg
        595                 600                 605

Phe Leu Val Lys Arg Ile Gly Pro Lys Lys Leu Pro His Val Pro Leu
        610                 615                 620

Arg Cys Lys Val Trp Ile Trp Arg Leu Ala Gln Glu Arg Arg
625                 630                 635

<210> SEQ ID NO 12
<211> LENGTH: 1217
<212> TYPE: DNA
<213> ORGANISM: Glycine max

<400> SEQUENCE: 12
cccatggctt cttccaacaa aatgaagatc atcaagtcaa cgttccttgt tttgtgcctc      60
tcagcctcgt cgttcctctg tccaatcaag gctcacggag gaagcggtga ttctcatgac     120
gatgaatctg atagcgaagg tttgcattct cggggtctga tcgtggtgaa aatatggtgt     180
ttgatcatct tccttgtgag cactttcgct ggtgggtttt ctccttactt ctaccgttgg     240
aacgagtctt tcttcttttt ggggactcag ttcgctggtg gggttttctt gggaaccctct    300
ttgatgcatt tcttgagcga ttctgatgag accttccgag accttaccac aaaatcttac     360
ccttttgcct atatgctggc ttcatctggg taccttctca ccatgcttgg tgactgtgtt     420
atcacttatg tcaccagcaa tagcaagagg gaagccaaag tggtggaact ggaaggaggg     480
acaacaccac cccaagagca tgagcatgac caagccagag tcattgcgc agtggcggag      540
acaacaaacc ctgtattatt gaagacttct tctgttggga caccattct actcatcctt      600
gcactgtgtt tccattcagt ttttgagggc attgcagttg gagttgcagg tactaaggcg     660
gacgcatgga ggaacttatg gacaatatcc ttgcacaaga tatttgctgc tattgcaatg     720
ggaattgctt tgctaaggat gttacctaag agaccctttg taacaacagc agcatattca     780
ttggcctttg ctgtctcaag ccccattggt gtggggattg gcattgccat aaatgccaca     840
acacaaggaa gcaccgcaga ttggatgttc gctataacaa tgggtattgc ttgtggggtc     900
ttcatctatg ttgctatcaa tcatttaata tccaaaggct caaaccaca caagacaaca     960
cgttacgaca ctccctggtt taggtttgtc gccgtgcttt ctggtgttgc tgttatagct    1020
gtagtcatga tctgggactg atcatcatgt ttcaattcct gtttttcttt gttcattaat    1080
aattgttcta cgaaattgtg cgtgtgtgat aattatgatg aatgtaccat tatatgctcg   1140
ccacaatatt aaacgttcgt ttaatatttt gaataaaaat ttatagtctt tgttctttca   1200
aaaaaaaaaa aaaaaaa                                                   1217

<210> SEQ ID NO 13
<211> LENGTH: 345
<212> TYPE: PRT
<213> ORGANISM: Glycine max

<400> SEQUENCE: 13

Met Ala Ser Ser Asn Lys Met Lys Ile Ile Lys Ser Thr Phe Leu Val
1               5                   10                  15

Leu Cys Leu Ser Ala Ser Ser Phe Leu Cys Pro Ile Lys Ala His Gly
            20                  25                  30

Gly Ser Gly Asp Ser His Asp Asp Glu Ser Asp Ser Glu Gly Leu His
        35                  40                  45

Ser Arg Gly Leu Ile Val Val Lys Ile Trp Cys Leu Ile Ile Phe Leu
    50                  55                  60
```

```
Val Ser Thr Phe Ala Gly Gly Val Ser Pro Tyr Phe Tyr Arg Trp Asn
 65                  70                  75                  80

Glu Ser Phe Leu Leu Leu Gly Thr Gln Phe Ala Gly Gly Val Phe Leu
                 85                  90                  95

Gly Thr Ser Leu Met His Phe Leu Ser Asp Ser Asp Glu Thr Phe Arg
            100                 105                 110

Asp Leu Thr Thr Lys Ser Tyr Pro Phe Ala Tyr Met Leu Ala Ser Ser
        115                 120                 125

Gly Tyr Leu Leu Thr Met Leu Gly Asp Cys Val Ile Thr Tyr Val Thr
    130                 135                 140

Ser Asn Ser Lys Arg Glu Ala Lys Val Val Glu Leu Glu Gly Gly Thr
145                 150                 155                 160

Thr Pro Pro Gln Glu His Glu His Asp Gln Ala Arg Asp His Cys Ala
                165                 170                 175

Val Ala Glu Thr Thr Asn Pro Val Leu Leu Lys Thr Ser Ser Val Gly
            180                 185                 190

Asp Thr Ile Leu Leu Ile Leu Ala Leu Cys Phe His Ser Val Phe Glu
        195                 200                 205

Gly Ile Ala Val Gly Val Ala Gly Thr Lys Ala Asp Ala Trp Arg Asn
    210                 215                 220

Leu Trp Thr Ile Ser Leu His Lys Ile Phe Ala Ile Ala Met Gly
225                 230                 235                 240

Ile Ala Leu Leu Arg Met Leu Pro Lys Arg Pro Phe Val Thr Thr Ala
                245                 250                 255

Ala Tyr Ser Leu Ala Phe Ala Val Ser Ser Pro Ile Gly Val Gly Ile
            260                 265                 270

Gly Ile Ala Ile Asn Ala Thr Thr Gln Gly Ser Thr Ala Asp Trp Met
        275                 280                 285

Phe Ala Ile Thr Met Gly Ile Ala Cys Gly Val Phe Ile Tyr Val Ala
    290                 295                 300

Ile Asn His Leu Ile Ser Lys Gly Phe Lys Pro His Lys Thr Thr Arg
305                 310                 315                 320

Tyr Asp Thr Pro Trp Phe Arg Phe Val Ala Val Leu Ser Gly Val Ala
                325                 330                 335

Val Ile Ala Val Val Met Ile Trp Asp
            340                 345

<210> SEQ ID NO 14
<211> LENGTH: 1630
<212> TYPE: DNA
<213> ORGANISM: Glycine max

<400> SEQUENCE: 14
acattaccat attccaataa aaaaaaatgt caccttcttt tcgcacatcc ctcttcctct      60
tcacactctc ccttctcttc ttcttctccc tctccgtctc cgcccacagc ggccacctcg    120
acgacgacga cgacgacgac gcggacgccg gaggcgacgc catccccaac ctccgtgctc    180
ggtccttgat tctcgcaaag gtgtggtgtt tgatcgttat ttttttttgct acttttgtat    240 cgggcgtttc cccctacatt ctgaaatgga acgaggggtt cttagttctg gggacccagt    300
ttgctggagg agtgtttctg ggaactgcaa tgatgcattt tctcagcgac gctaatgaaa    360
ccttcgggga cttaactcgc aaggagtacc ccttcgcgtt catgctcgcg tgtgcagggt    420
acttgatgac cctgctcgct gatgctgtca tttcctcggt tttgaagaat acggggcgtg    480
accaaccgcg tgatgctgag gatgtccaag ttcaagggc tgatgtgagc aaagtaagta    540
```

-continued

```
acaacagtgt tagatctcag tcacaacacc ggagccattc tatttctagc tctgatcatc    600
atcacttagc aaaccctgca cttggatctg tccgttcgct tggagacacc attttattga    660
ttgttgccct ttgtgcacat tctgtgtttg agggcttagc aattggagtt gctgagacca    720
aagcaaatgc atggaaagcc ttatggacaa tctgtctgca caagatattt gcagccattg    780
ccatgggaat tgctctcctc agaatgattc ctaaccgtcc ccttgtgtcg tgtgcagcct    840
atgcttttgc ttttgccatc tcgagtccaa ttggtgtggc cattggaatt atattggatg    900
ccacaactca gggtcatgtg gcggattgga tctttgccat tcaatgggt ctggcttgtg     960 gagtatttat ctatgtatca gtaaaccatc tgttggcaaa agggtacatg ccccacatac   1020
caacaaaggt tgactcagcc tatttcaagt tccttgccgt gttgttgggt gtgggagtga   1080
tagcggttgt gatgatttgg gacacctaag gttgttccaa gataacttct ctttacagca   1140
tttgcagaat cttttctctt ttctttttt tatcttttg ataatgaata cgtacattac     1200 agaaaagtt gtggtagttc ctaggtcaga tttggtattt ggatattctt gtcagaaatg    1260
atttcgtcaa tcatttataa ggtagaaaag atgacagaaa tttgcctcaa atgatagaaa   1320
agatgagcat gtattgagaa ttaagaggac ttataaaagt cttgggaaga agggtagttc   1380
acatggaggg tagcctaaat cattataggc aaagggaac ggagaagaaa tatatacaaa    1440
gctatagaaa tgaatttata gatcaatagt ttgtctgtag acatgattta aatagaagc    1500 tatgctgtta tttaattcat gtagcctata ccaccttgtg gggaaaaagg ttggttggtg   1560
gtggtgtgta tactttattg attgaataat tattatgagt tttgttcgta ataaaaaaaa   1620
aaaaaaaaa                                                           1630
```

<210> SEQ ID NO 15
<211> LENGTH: 360
<212> TYPE: PRT
<213> ORGANISM: Glycine max

<400> SEQUENCE: 15

Met Ser Pro Ser Phe Arg Thr Ser Leu Phe Leu Phe Thr Leu Ser Leu
1               5                   10                  15

Leu Phe Phe Phe Ser Leu Ser Val Ser Ala His Ser Gly His Leu Asp
                20                  25                  30

Asp Asp Asp Asp Asp Ala Asp Ala Gly Gly Asp Ala Ile Pro Asn
            35                  40                  45

Leu Arg Ala Arg Ser Leu Ile Leu Ala Lys Val Trp Cys Leu Ile Val
        50                  55                  60

Ile Phe Phe Ala Thr Phe Val Ser Gly Val Ser Pro Tyr Ile Leu Lys
65                  70                  75                  80

Trp Asn Glu Gly Phe Leu Val Leu Gly Thr Gln Phe Ala Gly Gly Val
                85                  90                  95

Phe Leu Gly Thr Ala Met Met His Phe Leu Ser Asp Ala Asn Glu Thr
            100                 105                 110

Phe Gly Asp Leu Thr Arg Lys Glu Tyr Pro Phe Ala Phe Met Leu Ala
        115                 120                 125

Cys Ala Gly Tyr Leu Met Thr Leu Leu Ala Asp Ala Val Ile Ser Ser
    130                 135                 140

Val Leu Lys Asn Thr Gly Arg Asp Gln Pro Arg Asp Ala Glu Asp Val
145                 150                 155                 160

Gln Val Gln Gly Ala Asp Val Ser Lys Val Ser Asn Asn Ser Val Arg
                165                 170                 175

```
Ser Gln Ser Gln His Arg Ser His Ser Ile Ser Ser Asp His His
            180                 185                 190

His Leu Ala Asn Pro Ala Leu Gly Ser Val Arg Ser Leu Gly Asp Thr
        195                 200                 205

Ile Leu Leu Ile Val Ala Leu Cys Ala His Ser Val Phe Glu Gly Leu
        210                 215                 220

Ala Ile Gly Val Ala Glu Thr Lys Ala Asn Ala Trp Lys Ala Leu Trp
225                 230                 235                 240

Thr Ile Cys Leu His Lys Ile Phe Ala Ile Ala Met Gly Ile Ala
                245                 250                 255

Leu Leu Arg Met Ile Pro Asn Arg Pro Leu Val Ser Cys Ala Ala Tyr
            260                 265                 270

Ala Phe Ala Phe Ala Ile Ser Ser Pro Ile Gly Val Ala Ile Gly Ile
        275                 280                 285

Ile Leu Asp Ala Thr Thr Gln Gly His Val Ala Asp Trp Ile Phe Ala
        290                 295                 300

Ile Ser Met Gly Leu Ala Cys Gly Val Phe Ile Tyr Val Ser Val Asn
305                 310                 315                 320

His Leu Leu Ala Lys Gly Tyr Met Pro His Ile Pro Thr Lys Val Asp
                325                 330                 335

Ser Ala Tyr Phe Lys Phe Leu Ala Val Leu Leu Gly Val Gly Val Ile
            340                 345                 350

Ala Val Val Met Ile Trp Asp Thr
            355                 360

<210> SEQ ID NO 16
<211> LENGTH: 1286
<212> TYPE: DNA
<213> ORGANISM: Oryza sativa

<400> SEQUENCE: 16
cgcacccgtc atcggtcgaa caccacacct gcgtccatgg cgggaggcag gggagcccgc    60
gccagcctcc acctccacct cgcctggctc tgcgccttcg cgaccaccgc gtgggcgcat   120
ggcggtggcg gcggcggggg cgattctgac gccgacgccg acggcggcgg cgaggggaag   180
ccggacctgc gggcgcgggg gctggtggcg gcgaagctgt ggtgcttggc ggtggtgttc   240
gccgggacgc tggccggcgg cgtgtccccc tacttcatgc ggtggaacga tgcgttcctg   300
gcgctgggca gcagttcgc gggggagtc ttcctcggca ccgccatgat gcacttcctc   360
gccgacgcca acgagacttt cgccgacctc ctccccggca ccgcctaccc cttcgcgttc   420
atgctcgcct gcgccggcta cgtcctcacc atgctcgccg actgcgccat ctccttcgtc   480
gtcgcccgcg cggcggccg gaccgaaccc gccgccgccg ccggtgcagg gctggaggag   540
ggtaagctga gcagcacaaa tggcaacgcc tctgacccac cagcagctga tgcggcggcg   600
caagaccact ccgtggcgtc gatgctgcgg aacgcgagca cgctcggcga cagcgtgctg   660
ctcatcgccg cgctctgctt ccactccgtc ttcgagggca tcgccatcgg agtcgccgag   720
acgaaggctg acgcatggaa ggcgctgtgg acgatcagcc tgcacaagat cttcgcggcc   780
atcgccatgg gcatcgcgct gctccggatg ctgccggacc ggccgttcct ctcctgcttc   840
ggctacgcct tcgccttcgc cgtctccagc cccgtcggcg tcggcatcgg catcgtcatc   900
gacgccacca gcagggccg ggtggccgac tggatcttcg ccgtctccat gggcctcgcc   960
accggcatct tcatctacgt ctccatcaac cacctcctct ccaagggcta caccccgctg  1020
```

-continued

```
aggcccgtcg ccgccgacac gccggcgggg aggctgctcg ccgtcgtcct cggcgtcgcc    1080
gtcatcgccg tcgtcatgat ctgggacacc tgatgccgct catgatttcg acgtttgtt    1140 ggttcttgca ggaatgtgtg tgtgtagtaa gttcgtcgtg aaattagcat gtgtaaagtt    1200
tgtgccactc caaccaaagt ttcaggatta tttatagctt tgaatatatc atcaacgctg    1260
gggcaccaaa aaaaaaaaaa aaaaaa                                          1286
```

<210> SEQ ID NO 17
<211> LENGTH: 358
<212> TYPE: PRT
<213> ORGANISM: Oryza sativa

<400> SEQUENCE: 17

```
Met Ala Gly Gly Arg Gly Ala Arg Ala Ser Leu His Leu His Leu Ala
  1               5                  10                  15

Trp Leu Cys Ala Phe Ala Thr Thr Ala Trp Ala His Gly Gly Gly Gly
             20                  25                  30

Gly Gly Gly Asp Ser Asp Ala Asp Ala Asp Gly Gly Gly Glu Gly Lys
         35                  40                  45

Pro Asp Leu Arg Ala Arg Gly Leu Val Ala Ala Lys Leu Trp Cys Leu
     50                  55                  60

Ala Val Val Phe Ala Gly Thr Leu Ala Gly Val Ser Pro Tyr Phe
 65                  70                  75                  80

Met Arg Trp Asn Asp Ala Phe Leu Ala Leu Gly Thr Gln Phe Ala Gly
                 85                  90                  95

Gly Val Phe Leu Gly Thr Ala Met Met His Phe Leu Ala Asp Ala Asn
            100                 105                 110

Glu Thr Phe Ala Asp Leu Leu Pro Gly Thr Ala Tyr Pro Phe Ala Phe
        115                 120                 125

Met Leu Ala Cys Ala Gly Tyr Val Leu Thr Met Leu Ala Asp Cys Ala
    130                 135                 140

Ile Ser Phe Val Val Ala Arg Gly Gly Gly Arg Thr Glu Pro Ala Ala
145                 150                 155                 160

Ala Ala Gly Ala Gly Leu Glu Glu Gly Lys Leu Ser Ser Thr Asn Gly
                165                 170                 175

Asn Ala Ser Asp Pro Pro Ala Ala Asp Ala Ala Gln Asp His Ser
            180                 185                 190

Val Ala Ser Met Leu Arg Asn Ala Ser Thr Leu Gly Asp Ser Val Leu
        195                 200                 205

Leu Ile Ala Ala Leu Cys Phe His Ser Val Phe Glu Gly Ile Ala Ile
    210                 215                 220

Gly Val Ala Glu Thr Lys Ala Asp Ala Trp Lys Ala Leu Trp Thr Ile
225                 230                 235                 240

Ser Leu His Lys Ile Phe Ala Ala Ile Ala Met Gly Ile Ala Leu Leu
                245                 250                 255

Arg Met Leu Pro Asp Arg Pro Phe Leu Ser Cys Phe Gly Tyr Ala Phe
            260                 265                 270

Ala Phe Ala Val Ser Ser Pro Val Gly Val Gly Ile Gly Ile Val Ile
        275                 280                 285

Asp Ala Thr Thr Gln Gly Arg Val Ala Asp Trp Ile Phe Ala Val Ser
    290                 295                 300

Met Gly Leu Ala Thr Gly Ile Phe Ile Tyr Val Ser Ile Asn His Leu
305                 310                 315                 320

Leu Ser Lys Gly Tyr Thr Pro Leu Arg Pro Val Ala Ala Asp Thr Pro
```

```
                    325                 330                 335
Ala Gly Arg Leu Leu Ala Val Val Leu Gly Val Ala Val Ile Ala Val
            340                 345                 350

Val Met Ile Trp Asp Thr
        355
```

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 18
caggaaacag ctatgacc                                           18

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 19
ctaaagggaa caaaagctg                                          19

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 20
tgtaaaacga cggccagt                                           18

<210> SEQ ID NO 21
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 21
atcccgggcg tttcgtagtg agcagtctcc ca                           32

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 22
gcgagctcag acactgtcgc tgatctcgtg at                           32

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 23
ccaagccaac atcgctggtc cgaac                                   25

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 24
gagcccgact cccggaactc gagag                                    25

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 25
atcccgggcg tcgcagttta cgtgtgttca cc                            32

<210> SEQ ID NO 26
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 26
atcccgggcg tcgcagttta cgtgtgttca cc                            32

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 27
ctgagctcaa gtcccactat aagaagtagt ct                            32

<210> SEQ ID NO 28
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 28
tgagctcaag tcaagcatcc cagatcatga ca                            32

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 29
actccgcatg ggtgtcacct ttcga                                    25

<210> SEQ ID NO 30
<211> LENGTH: 25
<212> TYPE: DNA
<213> ORGANISM: Artificial Sequence
<220> FEATURE:

-continued

```
<223> OTHER INFORMATION: Description of Artificial Sequence: Primer

<400> SEQUENCE: 30
cttctccacc ctcgcaaaca cgtca                                     25

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 31
caggaagcga ggcgatgttt gcag                                      24

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 32
gagcatgatg agcgtgagga ggcacgt                                   27

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 33
ggcgacctca tcatccagcg gctga                                     25

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 34
ccagtctgcc acagcgcctt ctgtag                                    26
```

ION TRANSPORTER STRESS-RELATED POLYPEPTIDES AND METHODS OF USE IN PLANTS

CROSS-REFERENCE TO RELATED APPLICATIONS

The present invention claims the priority benefit of U.S. Provisional Patent Application Ser. No. 60/345,816 filed Dec. 31, 2001, the entire contents of which are hereby incorporated by reference.

BACKGROUND OF THE INVENTION

1. Field of the Invention

This invention relates generally to nucleic acid sequences encoding polypeptides that are associated with abiotic stress responses and abiotic stress tolerance in plants. In particular, this invention relates to nucleic acid sequences encoding polypeptides that confer drought, cold, and/or salt tolerance to plants.

2. Background Art

Abiotic environmental stresses, such as drought stress, salinity stress, heat stress, and cold stress, are major limiting factors of plant growth and productivity. Crop losses and crop yield losses of major crops such as soybean, rice, maize (corn), cotton, and wheat caused by these stresses represent a significant economic and political factor and contribute to food shortages in many underdeveloped countries.

Plants are typically exposed during their life cycle to conditions of reduced environmental water content. Most plants have evolved strategies to protect themselves against these conditions of desiccation. However, if the severity and duration of the drought conditions are too great, the effects on development, growth, and yield of most crop plants are profound. Continuous exposure to drought conditions causes major alterations in the plant metabolism which ultimately lead to cell death and consequently yield losses.

Developing stress-tolerant plants is a strategy that has the potential to solve or mediate at least some of these problems. However, traditional plant breeding strategies to develop new lines of plants that exhibit resistance (tolerance) to these types of stresses are relatively slow and require specific resistant lines for crossing with the desired line. Limited germplasm resources for stress tolerance and incompatibility in crosses between distantly related plant species represent significant problems encountered in conventional breeding. Additionally, the cellular processes leading to drought, cold, and salt tolerance in model drought- and/or salt-tolerant plants are complex in nature and involve multiple mechanisms of cellular adaptation and numerous metabolic pathways. This multi-component nature of stress tolerance has not only made breeding for tolerance largely unsuccessful, but has also limited the ability to genetically engineer stress tolerant plants using biotechnological methods.

Drought stresses, cold stresses, and salt stresses have a common theme important for plant growth and that is water availability. As discussed above, most plants have evolved strategies to protect themselves against conditions of desiccation; however, if the severity and duration of the drought conditions are too great, the effects on plant development, growth and yield of most crop plants are profound. Furthermore, most of the crop plants are very susceptible to higher salt concentrations in the soil. Because high salt content in some soils results in less water being available for cell intake, high salt concentration has an effect on plants similar to the effect of drought on plants. Additionally, under freezing temperatures, plant cells lose water as a result of ice formation that starts in the apoplast and withdraws water from the symplast. A plant's molecular response mechanisms to each of these stress conditions are common, and ion transporters play an essential role in these molecular mechanisms.

Common damage from different stresses such as drought, salinity, and cold stress, appears to be mostly due to dehydration (Smirnoff, 1998, Curr. Opin. Biotech. 9:214–219). Drought (water stress)-tolerant and -sensitive plants can be clearly distinguished by the dramatic accumulation of ions and solutes in tolerant plants that leads to osmotic adjustments (Bohnert H. J and Jensen. R. G., 1996, TIBTECH 14:89–97). Drought and high salt conditions may interact with mineral nutrition in a number of ways as a consequence of (1) reduced transport of ions through the soil to the roots; and/or (2) modified uptake of ions by the roots.

Potassium is particularly important in plants not only as a nutrient, but also as an osmoticum. Potassium can make a 30–50% contribution to water potential, particularly in older leaf tissues (Munns R. et al., 1979, Aust. J. Plant Physiol. 6:379–389). After prolonged drought in the field, potassium accumulates in leaves of ryegrass and barley, and could have a role in osmotic adjustment. In addition, potassium plays a key role in the opening of the stomata. Because potassium is lost from the guard cells (Ehret, D. L. and Boyer, J. S., 1979, J. Exper. Bot. 30:225–234), a reduced supply of potassium reduces stomatal conductance to $CO_2$ much more than it reduces internal conductance (Terry, N. and Ulrich, A., 1973, Plant Physiol. 51:783–786).

Plant roots can absorb potassium over more than a 1000-fold concentration range, and the concentration dependence of potassium uptake by roots has complex kinetics, suggesting the presence of multiple potassium uptake systems. Gene families encoding inward-rectifying K+ channels have been identified in several plant species. The AKT1 K+ channel gene is predominantly expressed in roots and genetic analysis indicates that the AKT1 channel mediates the uptake of K+ in both the micromolar and millimolar ranges (Hirsch, R. H. et al., 1998, Science 280:918–921). Active transporters also participate in K+ uptake, and several candidate genes encoding energized transporters have been identified (Hirsch, R. E and Sussman, M. R., 1999, TIBTECH 17:356–361).

Little is known about the role of zinc ions in stress tolerance in plants. Zinc ions are often localized to the leaf vacuoles where they could have a role as an osmoticum. Zinc is also a co-factor for free-radical scavenging enzymes like Cu/Zn super-oxide dismutase. Zinc, like other metals, is often indirectly related to stress tolerance. An increase in the activity of zinc-chelating enzymes has been implicated in stress tolerance. However, there is no evidence to date that zinc transporters play a role in stress tolerance.

Although some genes that arc involved in stress responses in plants have been characterized, the characterization and cloning of plant genes that confer stress tolerance remains largely incomplete and fragmented. For example, certain studies have indicated that drought and salt stress in some plants may be due to additive gene effects, in contrast to other research that indicates specific genes are transcriptionally activated in vegetative tissue of plants under osmotic stress conditions. Although it is generally assumed that stress-induced proteins have a role in stress tolerance, direct evidence is still lacking, and the functions of many stress-responsive genes are unknown.

There is a need, therefore, to identify genes expressed in stress tolerant plants that have the capacity to confer stress resistance to its host plant and to other plant species. Newly generated stress tolerant plants will have many advantages, such as increasing the range in which crop plants can be cultivated by, for example, decreasing the water requirements of a plant species.

SUMMARY OF THE INVENTION

This invention fulfills in part the need to identify new, unique ion transporters capable of conferring stress tolerance to plants upon over-expression. The present invention describes a novel genus of Ion Transporter Stress-Related Polypeptides (ITSRPs) and ITSRP coding nucleic acids that are important for modulating a plant's response to an environmental stress. More particularly, over-expression of these ITSRP coding nucleic acids in a plant results in the plant's increased tolerance to an environmental stress.

Therefore, the present invention includes an isolated plant cell comprising an ITSRP coding nucleic acid, wherein expression of the nucleic acid sequence in the plant cell results in increased tolerance to environmental stress as compared to a wild type variety of the plant cell. Preferably, the ITSRP is an Active Potassium Channel Transporter (AKT) or a Zinc Transporter (ZT). More preferably, the Active Potassium Channel Transporter (AKT) or Zinc Transporter (ZT) is from *Physcomitrella patens, Brassica napus, Glycine max,* or *Oryza sativa*. Namely, described herein are the *Physcomitrella patens* Active Potassium Channel Transporter-1 (PpAKT-1), *Physcomitrella patens* Active Potassium Channel Transporter-2 (PpAKT-2), *Physcomitrella patens* Zinc Transporter-1 (PpZT-1), *Brassica napus* Active Potassium Channel Transporter-2 (BnAKT-2); *Glycine max* Zinc Transporter-1 (GmZT-1), *Glycine max* Zinc Transporter-2 (GmZT-2), and *Oryza sativa* Zinc Transporter-1 (OsZT-1).

The invention provides in some embodiments that the ITSRP and coding nucleic acid are those that are found in members of the genus *Physcomitrella, Brassica,* Glycine, or Oryza. In another preferred embodiment, the nucleic acid and polypeptide are from a *Physcomitrella patens* plant, a *Brassica napus* plant, a *Glycine max* plant, or an *Oryza sativa* plant. The invention provides that the environmental stress can be salinity, drought, temperature, metal, chemical, pathogenic and oxidative stresses, or combinations thereof. In preferred embodiments, the environmental stress can be selected from one or more of the group consisting of drought, high salt, and low temperature.

The invention further provides a seed produced by a transgenic plant transformed by an ITSRP coding nucleic acid, wherein the plant is true breeding for increased tolerance to environmental stress as compared to a wild type variety of the plant.

The invention further provides an agricultural product produced by any of the below-described transgenic plants, plant parts, or seeds. The invention further provides an isolated ITSRP as described below. The invention further provides an isolated ITSRP coding nucleic acid, wherein the ITSRP coding nucleic acid codes for an ITSRP as described below.

The invention further provides an isolated recombinant expression vector comprising an ITSRP coding nucleic acid as described below, wherein expression of the vector in a host cell results in increased tolerance to environmental stress as compared to a wild type variety of the host cell. The invention further provides a host cell containing the vector and a plant containing the host cell.

The invention further provides a method of producing a transgenic plant with an ITSRP coding nucleic acid, wherein expression of the nucleic acid in the plant results in increased tolerance to environmental stress as compared to a wild type variety of the plant comprising: (a) transforming a plant cell with an expression vector comprising an ITSRP coding nucleic acid, and (b) generating from the plant cell a transgenic plant with an increased tolerance to environmental stress as compared to a wild type variety of the plant. In preferred embodiments, the ITSRP and ITSRP coding nucleic acid are as described below.

The present invention further provides a method of identifying a novel ITSRP, comprising (a) raising a specific antibody response to an ITSRP, or fragment thereof, as described below; (b) screening putative ITSRP material with the antibody, wherein specific binding of the antibody to the material indicates the presence of a potentially novel ITSRP; and (c) identifying from the bound material a novel ITSRP in comparison to known ITSRP. Alternatively, hybridization with nucleic acid probes as described below can be used to identify novel ITSRP nucleic acids.

The present invention also provides methods of modifying stress tolerance of a plant comprising, modifying the expression of an ITSRP nucleic acid in the plant, wherein the ITSRP is as described below. The invention provides that this method can be performed such that the stress tolerance is either increased or decreased. Preferably, stress tolerance is increased in a plant via increasing expression of an ITSRP nucleic acid.

DETAILED DESCRIPTION OF THE INVENTION

Figure 1:
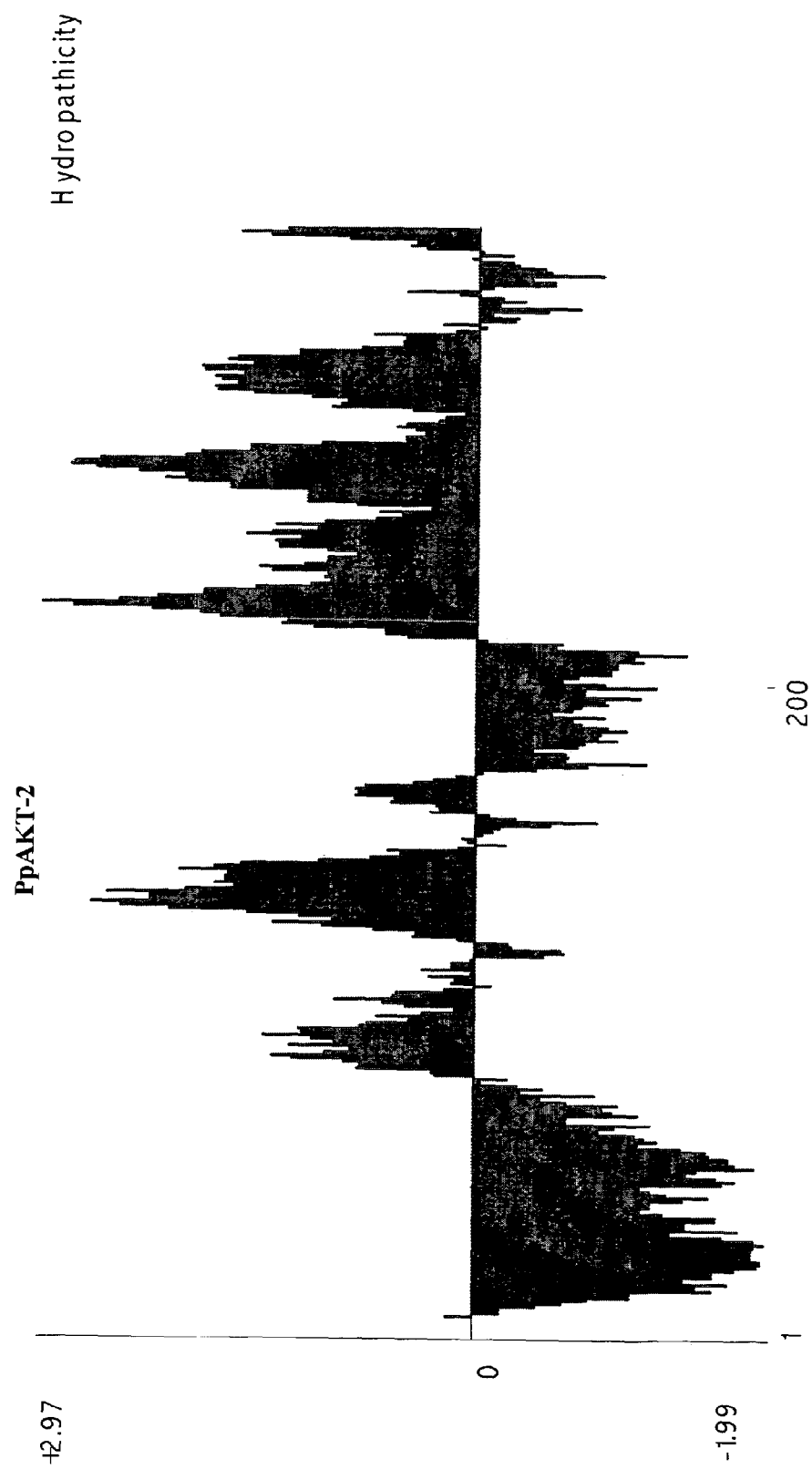
FIG. 1 shows the hydrophobicity plot of the predicted protein of PpAKT-2, showing the nine predicted transmembrane domains. Numbers below the graph indicate the amino acid position.
Figure 2:
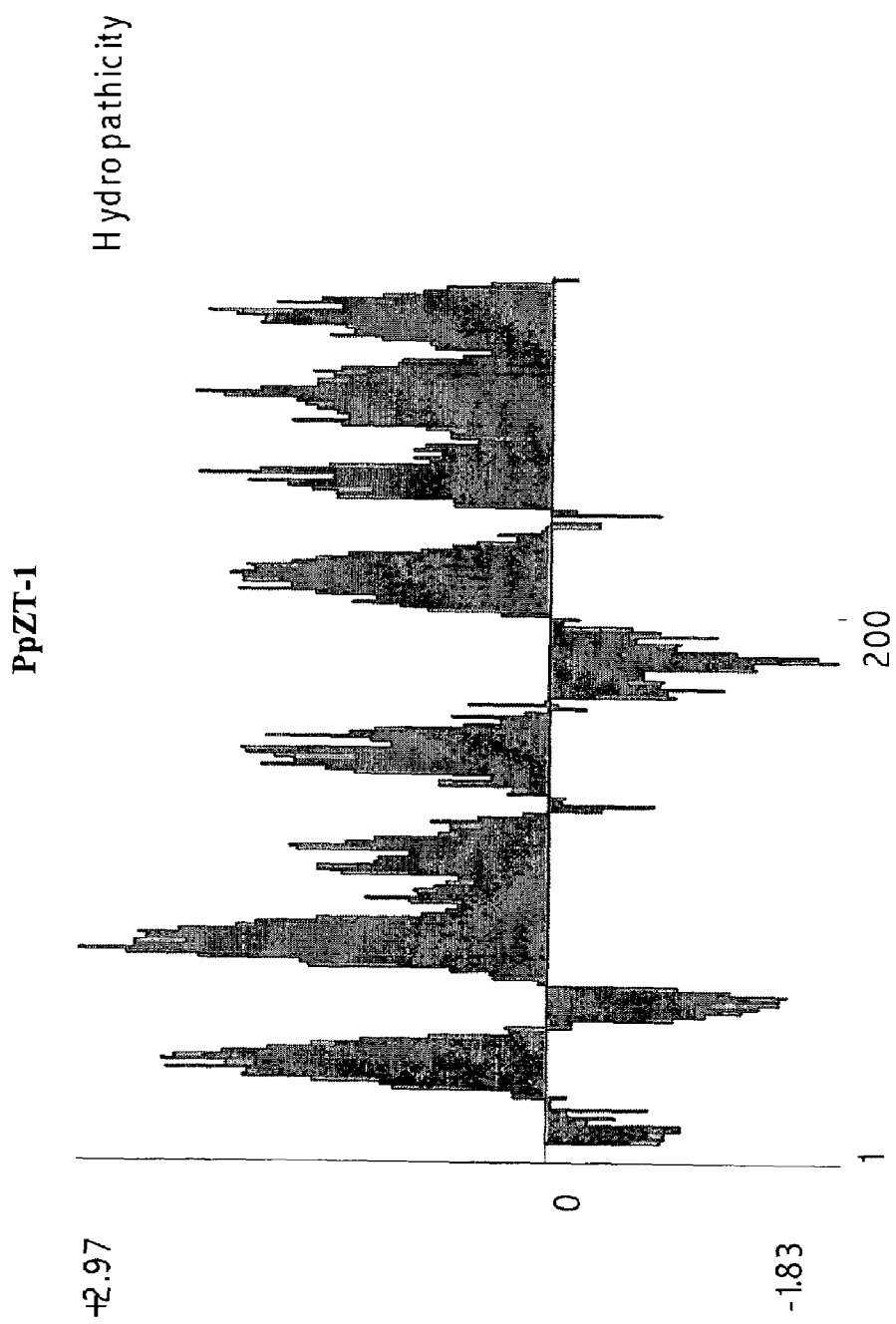
FIG. 2 shows the hydrophobicity plot of the predicted protein of PpZT-1, showing the eight predicted transmembrane domains. Numbers below the graph indicate the amino acid position.

The present invention may be understood more readily by reference to the following detailed description of the preferred embodiments of the invention and the Examples included herein. However, before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. In particular, the designation of the amino acid sequences as polypeptide "Ion Transporter Stress-Related Polypeptides" (ITSRPs), in no way limits the functionality of those sequences.

The present invention describes a novel genus of ITSRPs and ITSRP coding nucleic acids that are important for modulating a plant's response to an environmental stress. More particularly, over-expression of these ITSRP coding nucleic acids in a plant results in the plant's increased tolerance to an environmental stress. Representative members of the ITSRP genus include, but are not limited to, PpAKT-1, PpAKT-2, PpZT-1, BnAKT-2, GmZT-1, GmZT-2, and OsZT-1. In a preferred embodiment, all members of the genus are biologically active ion transporters. The PpAKT-1 polypeptides are described in PCT Patent Application No. PCT/US00/35356, the entire contents of which are hereby incorporated by reference, while PpAKT-2, PpZT-1, BnAKT-2, GmZT-1, GmZT-2, and OsZT-1 are described herein for the first time.

Accordingly, the present invention encompasses Active Potassium Transporter (AKT) and Zinc Transporter (ZT) polynucleotide and polypeptide sequences and their use for increasing a plant's tolerance to an environmental stress. In one embodiment, the AKT and ZT sequences are from a plant, preferably a *Physcomitrella* plant, a *Brassica* plant, a *Glycine* plant, or an Oryza plant, and more preferably a *Physcomitrella patens* plant, a *Brassica napus* plant, a *Glycine max* plant, or an *Oryza sativa* plant. The AKT sub-genus includes PpAKT-1 (SEQ ID NO:2 and SEQ ID NO:3), PpAKT-2 (SEQ ID NO:5 and SEQ ID NO:6), and BnAKT-2 (SEQ ID NO:10 and SEQ ID NO:11). PpAKT-1 and PpAKT-2 cDNAs have 46% identity, while the proteins have 12% identity and 25% similarity. The BnAKT-2 protein sequence has 39% identity and 53% similarity to the PpAKT-2 protein sequence (SEQ ID NO:6). The ZT sub-genus includes PpZT-1 (SEQ ID NO:8 and SEQ ID NO:9), GmZT-1 (SEQ ID NO:12 and SEQ ID NO:13), GmZT-2 (SEQ ID NO:14 and SEQ ID NO:15), and OsZT-1 (SEQ ID NO:16 and SEQ ID NO:17). The GmZT-1 protein sequence, the GmZT-2 protein sequence, and the OsZT-1 protein sequence have 47% identity and 63% similarity, 50% identity and 63% similarity, and 48% identity and 63% similarity, respectively, to the PpZT-1 protein sequence (SEQ ID NO:9).

It is plausible that high salt stress situations would lead to an imbalance in the concentration of some nutrients, including zinc. For this matter, the overexpression of a zinc-transporter could compensate for this nutritional imbalance under salt-stress conditions, thus leading to tolerance to high-salt conditions. It is also possible that removal of zinc from the cytoplasm would lead to stress tolerance.

The present invention provides a transgenic plant cell transformed by an ITSRP coding nucleic acid, wherein expression of the nucleic acid sequence in the plant cell results in increased tolerance to an environmental stress as compared to a wild type variety of the plant cell. The invention further provides transgenic plant parts and transgenic plants containing the plant cells described herein. Plant parts include, but are not limited to, stems, roots, ovules, stamens, leaves, embryos, meristematic regions, callus tissue, gametophytes, sporophytes, pollen, microspores, and the like. In one embodiment, the transgenic plant is male sterile. Also provided is a plant seed produced by a transgenic plant transformed by an ITSRP coding nucleic acid, wherein the seed contains the ITSRP coding nucleic acid, and wherein the plant is true breeding for increased tolerance to environmental stress as compared to a wild type variety of the plant. The invention further provides a seed produced by a transgenic plant expressing an ITSRP, wherein the seed contains the ITSRP, and wherein the plant is true breeding for increased tolerance to environmental stress as compared to a wild type variety of the plant. The invention also provides an agricultural product produced by any of the below-described transgenic plants, plant parts, and plant seeds. Agricultural products include, but are not limited to, plant extracts, proteins, amino acids, carbohydrates, fats, oils, polymers, vitamins, and the like.

As used herein, the term "variety" refers to a group of plants within a species that share constant characters that separate them from the typical form and from other possible varieties within that species. While possessing at least one distinctive trait, a variety is also characterized by some variation between individuals within the variety, based primarily on the Mendelian segregation of traits among the progeny of succeeding generations. A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from the transgenic expression of one or more DNA sequences introduced into a plant variety.

The present invention describes for the first time that the *Physcomitrella patens* ITSRPs, PpAKT-2 and PpZT-1; *Brassica napus* ITSRP, BnAKT-2; *Glycine max* ITSRPs, GmZT-1 and GmZT-2; and *Oryza sativa* ITSRP, OsZT-1 are useful for increasing a plant's tolerance to environmental stress. As used herein, the term polypeptide refers to a chain of at least four amino acids joined by peptide bonds. The chain may be linear, branched, circular, or combinations thereof. Accordingly, the present invention provides isolated ITSRPs selected from AKTs and ZTs, and more preferably PpAKT-2, PpZT-1, BnAKT-2, GmZT-1, GmZT-2, OsZT-1, and homologs thereof. In preferred embodiments, the ITSRP is selected from: 1) *Physcomitrella patens* Active Potassium Transporter-2 (PpAKT-2) polypeptide as defined in SEQ ID NO:6; 2) *Physcomitrella patens* Zinc Transporter-1 (PpZT-1) polypeptide as defined in SEQ ID NO:9; 3) *Brassica napus* Active Potassium Transporter-2 (BnAKT-2) as defined in SEQ ID NO:11; 4) *Glycine max* Zinc Transporter-1 (GmZT-1) as defined in SEQ ID NO:13; 5) *Glycine max* Zinc Transporter-2 (GmZT-2) as defined in SEQ ID NO:15; and 6) *Oryza sativa* Zinc Transporter-1 (OsZT-1) as defined in SEQ ID NO:17; and homologs and orthologs thereof. Homologs and orthologs of the amino acid sequences are defined below.

The ITSRPs of the present invention are preferably produced by recombinant DNA techniques. For example, a nucleic acid molecule encoding the polypeptide is cloned into an expression vector (as described below), the expression vector is introduced into a host cell (as described below) and the ITSRP is expressed in the host cell. The ITSRP can then be isolated from the cells by an appropriate purification scheme using standard polypeptide purification techniques. For the purposes of the invention, the term "recombinant polynucleotide" refers to a polynucleotide that has been altered, rearranged, or modified by genetic engineering. Examples include any cloned polynucleotide, and polynucleotides that are linked or joined to heterologous sequences. The term "recombinant" does not refer to alterations to polynucleotides that result from naturally occurring events, such as spontaneous mutations. Alternative to recombinant expression, an ITSRP, or peptide thereof, can be synthesized chemically using standard peptide synthesis techniques. Moreover, native ITSRP can be isolated from cells (e.g., *Physcomitrella patens, Brassica napus, Glycine max*, or *Oryza sativa* cells), for example using an anti-ITSRP antibody, which can be produced by standard techniques utilizing an ITSRP or fragment thereof.

As used herein, the term "environmental stress" refers to sub-optimal conditions associated with salinity, drought, temperature, metal, chemical, pathogenic and oxidative stresses, or combinations thereof. In preferred embodiments, the environmental stress can be selected from one or more of the group consisting of salinity, drought, or temperature, or combinations thereof, and in particular, can be selected from one or more of the group consisting of high salinity, low water content, or low temperature. It is also to be understood that as used in the specification and in the claims, "a" or "an" can mean one or more, depending upon the context in which it is used. Thus, for example, reference to "a cell" can mean that at least one cell can be utilized.

As also used herein, the term "nucleic acid" and "polynucleotide" refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine, and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

An "isolated" nucleic acid molecule is one that is substantially separated from other nucleic acid molecules, which are present in the natural source of the nucleic acid (i.e., sequences encoding other polypeptides). Preferably, an "isolated" nucleic acid is free of some of the sequences, which naturally flank the nucleic acid (i.e. sequences located at the 5' and 3' ends of the nucleic acid) in its naturally occurring replicon. For example, a cloned nucleic acid is considered isolated. In various embodiments, the isolated ITSRP nucleic acid molecule can contain less than about 5 kb, 4 kb, 3 kb, 2 kb, 1 kb, 0.5 kb, or 0.1 kb of nucleotide sequences which naturally flank the nucleic acid molecule in genomic DNA of the cell from which the nucleic acid is derived (e.g., a *Physcomitrella patens* cell, a *Brassica napus* cell, a *Glycine max* cell, or an *Oryza sativa* cell). A nucleic acid is also considered isolated if it has been altered by human intervention, or placed in a locus or location that is not its natural site, or if it is introduced into a cell by agroinfection. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

Specifically excluded from the definition of "isolated nucleic acids" are: naturally-occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified nucleic acid makes up less than 5% of the number of nucleic acid inserts in the vector molecules. Further specifically excluded are whole cell genomic DNA or whole cell RNA preparations (including whole cell preparations that are mechanically sheared or enzymatically digested). Even further specifically excluded are the whole cell preparations found as either an in vitro preparation or as a heterogeneous mixture separated by electrophoresis wherein the nucleic acid of the invention has not further been separated from the heterologous nucleic acids in the electrophoresis medium (e.g., further separating by excising a single band from a heterogeneous band population in an agarose gel or nylon blot).

A nucleic acid molecule of the present invention, e.g., a nucleic acid molecule having a nucleotide sequence of SEQ ID NO:4, SEQ ID NO:5, SEQ ID NO:7, SEQ ID NO:8, SEQ ID NO:10, SEQ ID NO:12, SEQ ID NO:14, SEQ ID NO:16, or a portion thereof, can be isolated using standard molecular biology techniques and the sequence information provided herein. For example, a *P. patens* ITSRP cDNA can be isolated from a *P. patens* library using all or portion of one of the sequences of SEQ ID NO:4 and SEQ ID NO:7. Moreover, a nucleic acid molecule encompassing all or a portion of one of the sequences of SEQ ID NO:4, SEQ ID NO:5, SEQ ID NO:7, SEQ ID NO:8, SEQ ID NO:10, SEQ ID NO:12, SEQ ID NO:14, and SEQ ID NO:16 can be isolated by the polymerase chain reaction using oligonucleotide primers designed based upon this sequence. For example, mRNA can be isolated from plant cells (e.g., by the guanidinium-thiocyanate extraction procedure of Chirgwin et al., 1979, Biochemistry 18:5294–5299), and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in SEQ ID NO:4, SEQ ID NO:5, SEQ ID NO:7, SEQ ID NO:8, SEQ ID NO:10, SEQ ID NO:12, SEQ ID NO:14, and SEQ ID NO:16. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to an ITSRP nucleotide sequence can be prepared by standard synthetic techniques, e.g., using an automated DNA synthesizer.

In a preferred embodiment, an isolated nucleic acid molecule of the invention comprises one of the nucleotide sequences shown in SEQ ID NO:5, SEQ ID NO:8, SEQ ID NO:10, SEQ ID NO:12, SEQ ID NO:14, or SEQ ID NO:16. These cDNAs may comprise sequences encoding the ITSRPs, (i.e., the "coding region"), as well as 5' untranslated sequences and 3' untranslated sequences. It is to be understood that SEQ ID NO:5 and SEQ ID NO:8 comprise both coding regions and 5' and 3' untranslated regions. Alternatively, the nucleic acid molecules of the present invention can comprise only the coding region of any of the sequences in SEQ ID NO:5, SEQ ID NO:8, SEQ ID NO:10, SEQ ID NO:12, SEQ ID NO:14, and SEQ ID NO:16, or can contain whole genomic fragments isolated from genomic DNA. The coding regions of the sequences are as follows: the PpAKT-2 coding region comprises nucleotides 55–2523 of SEQ ID NO:5; the PpZT-1 coding region comprises nucleotides 21–1094 of SEQ ID NO:8; the BnAKT-2 coding region comprises nucleotides 128–2041 of SEQ ID NO:10; the GmZT-1 coding region comprises nucleotides 4–1038 of SEQ ID NO:12; the GmZT-2 coding region comprises nucleotides 27–1106 of SEQ ID NO:14; and the OsZT-1 coding region comprises nucleotides 37–1110 of SEQ ID NO:16. Accordingly, the present invention includes ITSRP nucleic acids comprising nucleotides 55–2523 of SEQ ID NO:5; nucleotides 21–1094 of SEQ ID NO:8; nucleotides 128–2041 of SEQ ID NO:10; nucleotides 4–1038 of SEQ ID NO:12; nucleotides 27–1106 of SEQ ID NO:14; or nucleotides 37–1110 of SEQ ID NO:16. The present invention also includes ITSRP coding nucleic acids that encode ITSRPs as described herein. Preferred is an ITSRP coding nucleic acid that encodes an ITSRP selected from the group consisting of PpAKT-2 (SEQ ID NO:6), PpZT-1 (SEQ ID NO:9), BnAKT-2 (SEQ ID NO:11), GmZT-1 (SEQ ID NO:13), GmZT-2 (SEQ ID NO:15), and OsZT-1 (SEQ ID NO:17).

Moreover, the nucleic acid molecule of the invention can comprise a portion of the coding region of one of the sequences in SEQ ID NO:5, SEQ ID NO:8, SEQ ID NO:10, SEQ ID NO:12, SEQ ID NO:14, and SEQ ID NO:16, for example, a fragment that can be used as a probe or primer or a fragment encoding a biologically active portion of an ITSRP. The nucleotide sequences determined from the cloning of the ITSRP genes from *P. patens, Brassica napus, Glycine max*, and *Oryza sativa* allow for the generation of probes and primers designed for use in identifying and/or cloning ITSRP homologs in other cell types and organisms, as well as ITSRP homologs from other mosses and related species. The portion of the coding region can also encode a biologically active fragment of an ITSRP.

As used herein, the term "biologically active portion of" an ITSRP is intended to include a portion, e.g., a domain/motif, of an ITSRP that participates in modulation of stress tolerance in a plant, and more preferably, drought tolerance or salt tolerance. For the purposes of the present invention, modulation of stress tolerance refers to at least a 10% increase or decrease in the stress tolerance of a transgenic plant comprising an ITSRP expression cassette (or expression vector) as compared to the stress tolerance of a non-transgenic control plant. Methods for quantitating stress tolerance are provided at least in Example 7 below. In a preferred embodiment, the biologically active portion of an ITSRP increases a plant's tolerance to an environmental stress.

Biologically active portions of an ITSRP include peptides comprising amino acid sequences derived from the amino acid sequence of an ITSRP, e.g., an amino acid sequence of SEQ ID NO:6, SEQ ID NO:9, SEQ ID NO:11, SEQ ID NO:13, SEQ ID NO:15, or SEQ ID NO:17, or the amino acid sequence of a polypeptide identical to an ITSRP, which include fewer amino acids than a full length ITSRP or the full length polypeptide which is identical to an ITSRP, and exhibit at least one activity of an ITSRP. Typically, biologically active portions (e.g., peptides which are, for example, 5, 10, 15, 20, 30, 35, 36, 37, 38, 39, 40, 50, 100, or more amino acids in length) comprise a domain or motif with at least one activity of an ITSRP. Moreover, other biologically active portions in which other regions of the polypeptide are deleted, can be prepared by recombinant techniques and evaluated for one or more of the activities described herein. Preferably, the biologically active portions of an ITSRP include one or more selected domains/motifs or portions thereof having biological activity such as a PFAM domain (See Tables 1 and 9).

The invention also provides ITSRP chimeric or fusion polypeptides. As used herein, an ITSRP "chimeric polypeptide" or "fusion polypeptide" comprises an ITSRP operatively linked to a non-ITSRP. An ITSRP refers to a polypeptide having an amino acid sequence corresponding to an ITSRP, whereas a non-ITSRP refers to a polypeptide having an amino acid sequence corresponding to a polypeptide which is not substantially identical to the ITSRP, e.g., a polypeptide that is different from the ITSRP and is derived from the same or a different organism. Within the fusion polypeptide, the term "operatively linked" is intended to indicate that the ITSRP and the non-ITSRP are fused to each other so that both sequences fulfill the proposed function attributed to the sequence used. The non-ITSRP can be fused to the N-terminus or C-terminus of the ITSRP. For example, in one embodiment, the fusion polypeptide is a GST-ITSRP fusion polypeptide in which the ITSRP sequences are fused to the C-terminus of the GST sequences. Such fusion polypeptides can facilitate the purification of recombinant ITSRPs. In another embodiment, the fusion polypeptide is an ITSRP containing a heterologous signal sequence at its N-terminus. In certain host cells (e.g., mammalian host cells), expression and/or secretion of an ITSRP can be increased through use of a heterologous signal sequence.

Preferably, an ITSRP chimeric or fusion polypeptide of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and re-amplified to generate a chimeric gene sequence (See, for example, Current Protocols in Molecular Biology, Eds. Ausubel et al. John Wiley & Sons: 1992). Moreover, many expression vectors are commercially available that already encode a fusion moiety (e.g., a GST polypeptide). An ITSRP encoding nucleic acid can be cloned into such an expression vector such that the fusion moiety is linked in-frame to the ITSRP.

In addition to fragments and fusion polypeptides of the ITSRPs described herein, the present invention includes homologs and analogs of naturally occurring ITSRPs and ITSRP encoding nucleic acids in a plant. "Homologs" are defined herein as two nucleic acids or polypeptides that have similar, or "identical," nucleotide or amino acid sequences, respectively. Homologs include allelic variants, orthologs, paralogs, agonists, and antagonists of ITSRPs as defined hereafter. The term "homolog" further encompasses nucleic acid molecules that differ from one of the nucleotide sequences shown in SEQ ID NO:5, SEQ ID NO:8, SEQ ID NO:10, SEQ ID NO:12, SEQ ID NO:14, and SEQ ID NO:16 (and portions thereof) due to degeneracy of the genetic code and thus encode the same ITSRP as that encoded by the nucleotide sequences shown in SEQ ID NO:5, SEQ ID NO:8, SEQ ID NO:10, SEQ ID NO:12, SEQ ID NO:14, or SEQ ID NO:16. As used herein, a "naturally occurring" ITSRP refers to an ITSRP amino acid sequence that occurs in nature. Preferably, a naturally occurring ITSRP comprises an amino acid sequence selected from the group consisting of SEQ ID NO:6, SEQ ID NO:9, SEQ ID NO:11, SEQ ID NO:13, SEQ ID NO:15, and SEQ ID NO:17.

An agonist of the ITSRP can retain substantially the same, or a subset, of the biological activities of the ITSRP. An antagonist of the ITSRP can inhibit one or more of the activities of the naturally occurring form of the ITSRP. For example, the ITSRP antagonist can competitively bind to a downstream or upstream member of the cell membrane component metabolic cascade that includes the ITSRP, or bind to an ITSRP that mediates transport of compounds across such membranes, thereby preventing translocation from taking place.

Nucleic acid molecules corresponding to natural allelic variants and analogs, orthologs, and paralogs of an ITSRP cDNA can be isolated based on their identity to the *Physcomitrella patens, Brassica napus, Glycine max*, or *Oryza sativa* ITSRP nucleic acids described herein using ITSRP cDNAs, or a portion thereof, as a hybridization probe according to standard hybridization techniques under stringent hybridization conditions. In an alternative embodiment, homologs of the ITSRP can be identified by screening combinatorial libraries of mutants, e.g., truncation mutants, of the ITSRP for ITSRP agonist or antagonist activity. In one embodiment, a variegated library of ITSRP variants is generated by combinatorial mutagenesis at the nucleic acid level and is encoded by a variegated gene library. A variegated library of ITSRP variants can be produced by, for example, enzymatically ligating a mixture of synthetic oligonucleotides into gene sequences such that a degenerate set of potential ITSRP sequences is expressible as individual polypeptides, or alternatively, as a set of larger fusion polypeptides (e.g., for phage display) containing the set of ITSRP sequences therein. There are a variety of methods that can be used to produce libraries of potential ITSRP homologs from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential ITSRP sequences. Methods for synthesizing degenerate oligonucleotides are known in the art (See, e.g., Narang, S. A., 1983, Tetrahedron 39:3; Itakura et al., 1984, Annu. Rev. Biochem. 53:323; Itakura et al., 1984, Science 198:1056; Ike et al., 1983, Nucleic Acid Res. 11:477).

In addition, libraries of fragments of the ITSRP coding regions can be used to generate a variegated population of ITSRP fragments for screening and subsequent selection of homologs of an ITSRP. In one embodiment, a library of coding sequence fragments can be generated by treating a double stranded PCR fragment of an ITSRP coding sequence with a nuclease under conditions wherein nicking occurs only about once per molecule, denaturing the double stranded DNA, renaturing the DNA to form double stranded DNA, which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal, and internal fragments of various sizes of the ITSRP.

Several techniques, are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of ITSRP homologs. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify ITSRP homologs (Arkin and Yourvan, 1992, PNAS 89:7811–7815; Delgrave et al., 1993, Polypeptide Engineering 6(3):327–331). In another embodiment, cell based assays can be exploited to analyze a variegated ITSRP library, using methods well known in the art. The present invention further provides a method of identifying a novel ITSRP, comprising (a) raising a specific antibody response to an ITSRP, or a fragment thereof, as described herein; (b) screening putative ITSRP material with the antibody, wherein specific binding of the antibody to the material indicates the presence of a potentially novel ITSRP; and (c) analyzing the bound material in comparison to known ITSRP, to determine its novelty.

As stated above, the present invention includes ITSRPs and homologs thereof. To determine the percent sequence identity of two amino acid sequences (e.g., one of the sequences of SEQ ID NO:6, SEQ ID NO:9, SEQ ID NO:11, SEQ ID NO:13, SEQ ID NO:15, and SEQ ID NO:17, and a mutant form thereof), the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence (e.g., one of the sequences of SEQ ID NO:6, SEQ ID NO:9, SEQ ID NO:11, SEQ ID NO:13, SEQ ID NO:15, and SEQ ID NO:17) is occupied by the same amino acid residue at the corresponding position in the other sequence (e.g., a mutant form of the sequence of SEQ ID NO:6, SEQ ID NO:9, SEQ ID NO:11, SEQ ID NO:13, SEQ ID NO:15, and SEQ ID NO:17), then the molecules are identical at that position. The same type of comparison can be made between two nucleic acid sequences.

The percent sequence identity between the two sequences is a function of the number of identical positions shared by the sequences (i.e., percent sequence identity=numbers of identical positions/total numbers of positions×100). Preferably, the isolated amino acid homologs included in the present invention are at least about 50–60%, preferably at least about 60–70%, and more preferably at least about 70–75%, 75–80%, 80–85%, 85–90%, or 90–95%, and most preferably at least about 96%, 97%, 98%, 99%, or more identical to an entire amino acid sequence shown in SEQ ID NO:6, SEQ ID NO:9, SEQ ID NO:11, SEQ ID NO:13, SEQ ID NO:15, or SEQ ID NO:17. In yet another embodiment, the isolated amino acid homologs included in the present invention are at least about 50–60%, preferably at least about 60–70%, and more preferably at least about 70–75%, 75–80%, 80–85%, 85–90%, or 90–95%, and most preferably at least about 96%, 97%, 98%, 99%, or more identical to an entire amino acid sequence encoded by a nucleic acid sequence shown in SEQ ID NO:5, SEQ ID NO:8, SEQ ID NO:10, SEQ ID NO:12, SEQ ID NO:14, or SEQ ID NO:16. In other embodiments, the ITSRP amino acid homologs have sequence identity over at least 15 contiguous amino acid residues, more preferably at least 25 contiguous amino acid residues, and most preferably at least 35 contiguous amino acid residues of SEQ ID NO:6, SEQ ID NO:9, SEQ ID NO:11, SEQ ID NO:13, SEQ ID NO:15, or SEQ ID NO:17.

In another preferred embodiment, an isolated nucleic acid homolog of the invention comprises a nucleotide sequence which is at least about 40–60%, preferably at least about 60–70%, more preferably at least about 70–75%, 75–80%, 80–85%, 85–90%, or 90–95%, and even more preferably at least about 95%, 96%, 97%, 98%, 99%, or more identical to a nucleotide sequence shown in SEQ ID NO:5, SEQ ID NO:8, SEQ ID NO:10, SEQ ID NO:12, SEQ ID NO:14, or SEQ ID NO:16, or to a portion comprising at least 60 consecutive nucleotides thereof. In one embodiment, the ITSRP homolog nucleotide sequence is about 47% identical to a nucleotide sequence shown in SEQ ID NO:5. The preferable length of sequence comparison for nucleic acids is at least 75 nucleotides, more preferably at least 100 nucleotides, and most preferably the entire length of the coding region. It is even more preferable that the nucleic acid homologs encode proteins having homology with SEQ ID NO:6, SEQ ID NO:9, SEQ ID NO:11, SEQ ID NO:13, SEQ ID NO:15, or SEQ ID NO:17 over the PFAM domains shown in Tables 1 and 9.

It is further preferred that the isolated nucleic acid homolog of the invention encodes an ITSRP, or portion thereof, that is at least 70% identical to an amino acid sequence of SEQ ID NO:6, SEQ ID NO:9, SEQ ID NO:11, SEQ ID NO:13, SEQ ID NO:15, or SEQ ID NO:17 and that functions as a modulator of an environmental stress response in a plant. In a more preferred embodiment, overexpression of the nucleic acid homolog in a plant increases the tolerance of the plant to an environmental stress. In a further preferred embodiment, the nucleic acid homolog encodes an ITSRP that functions as an ion transporter.

For the purposes of the invention, the percent sequence identity between two nucleic acid or polypeptide sequences is determined using the Vector NTI 6.0 (PC) software package (InforMax, 7600 Wisconsin Ave., Bethesda, Md. 20814). A gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings. For purposes of a multiple alignment (Clustal W algorithm), the gap opening penalty is 10, and the gap extension penalty is 0.05 with blosum62 matrix. It is to be understood that for the purposes of determining sequence identity when comparing a DNA sequence to an RNA sequence, a thymidine nucleotide is equivalent to a uracil nucleotide.

In another aspect, the invention provides an isolated nucleic acid comprising a polynucleotide that hybridizes to the polynucleotide of SEQ ID NO:5, SEQ ID NO:8, SEQ ID NO:10, SEQ ID NO:12, SEQ ID NO:14, or SEQ ID NO:16 under stringent conditions. More particularly, an isolated nucleic acid molecule of the invention is at least 15 nucleotides in length and hybridizes under stringent conditions to the nucleic acid molecule comprising a nucleotide sequence of SEQ ID NO:5, SEQ ID NO:8, SEQ ID NO:10, SEQ ID NO:12, SEQ ID NO:14, or SEQ ID NO:16. In other embodiments, the nucleic acid is at least 30, 50, 100, 250, or more nucleotides in length. Preferably, an isolated nucleic acid homolog of the invention comprises a nucleotide sequence which hybridizes under highly stringent conditions to the nucleotide sequence shown in SEQ ID NO:5, SEQ ID NO:8, SEQ ID NO:10, SEQ ID NO:12, SEQ ID NO:14, or SEQ ID NO:16 and functions as a modulator of stress tolerance in a plant. In a further preferred embodiment, overexpression of the isolated nucleic acid homolog in a plant increases a plant's tolerance to an environmental stress. In an even further preferred embodiment, the isolated nucleic acid homolog encodes an ITSRP that functions as an ion transporter.

As used herein with regard to hybridization for DNA to a DNA blot, the term "stringent conditions" refers to hybridization overnight at 60° C. in 10× Denhart's solution, 6×SSC, 0.5% SDS, and 100 µg/ml denatured salmon sperm DNA. Blots are washed sequentially at 62° C. for 30 minutes each time in 3×SSC/0.1% SDS, followed by 1×SSC/0.1% SDS, and finally 0.1×SSC/0.1% SDS. As also used herein, "highly stringent conditions" refers to hybridization overnight at 65° C. in 10× Denharts solution, 6×SSC, 0.5% SDS, and 100 µg/ml denatured salmon sperm DNA. Blots are washed sequentially at 65° C. for 30 minutes each time in 3×SSC/0.1% SDS, followed by 1×SSC/0.1% SDS, and finally 0.1×SSC/0.1% SDS. Methods for nucleic acid hybridizations are described in Meinkoth and Wahl, 1984, Anal. Biochem. 138:267–284; Current Protocols in Molecular Biology, Chapter 2, Ausubel et al. Eds., Greene Publishing and Wiley-Interscience, New York, 1995; and Tijssen, 1993, Laboratory Techniques in Biochemistry and Molecular Biology: Hybridization with Nucleic Acid Probes, Part I, Chapter 2, Elsevier, New York, 1993. Preferably, an isolated nucleic acid molecule of the invention that hybridizes under stringent or highly stringent conditions to a sequence of SEQ ID NO:5, SEQ ID NO:8, SEQ ID NO:10, SEQ ID NO:12, SEQ ID NO:14, or SEQ ID NO:16 corresponds to a naturally occurring nucleic acid molecule. As used herein, a "naturally occurring" nucleic acid molecule refers to an RNA or DNA molecule having a nucleotide sequence that occurs in nature (e.g., encodes a natural polypeptide). In one embodiment, the nucleic acid encodes a naturally occurring *Physcomitrella patens* ITSRP, *Brassica napus* ITSRP, *Glycine max* ITSRP, or an *Oryza sativa* ITSRP.

Using the above-described methods, and others known to those of skill in the art, one of ordinary skill in the art can isolate homologs of the ITSRPs comprising amino acid sequences shown in SEQ ID NO:6, SEQ ID NO:9, SEQ ID NO:11, SEQ ID NO:13, SEQ ID NO:15, or SEQ ID NO:17. One subset of these homologs is allelic variants. As used herein, the term "allelic variant" refers to a nucleotide sequence containing polymorphisms that lead to changes in the amino acid sequences of an ITSRP and that exist within a natural population (e.g., a plant species or variety). Such natural allelic variations can typically result in 1–5% variance in an ITSRP nucleic acid. Allelic variants can be identified by sequencing the nucleic acid sequence of interest in a number of different plants, which can be readily carried out by using hybridization probes to identify the same ITSRP genetic locus in those plants. Any and all such nucleic acid variations and resulting amino acid polymorphisms or variations in an ITSRP that are the result of natural allelic variation and that do not alter the functional activity of an ITSRP, are intended to be within the scope of the invention.

Moreover, nucleic acid molecules encoding ITSRPs from the same or other species such as ITSRP analogs, orthologs, and paralogs, are intended to be within the scope of the present invention. As used herein, the term "analogs" refers to two nucleic acids that have the same or similar function, but that have evolved separately in unrelated organisms. As used herein, the term "orthologs" refers to two nucleic acids from different species, but that have evolved from a common ancestral gene by speciation. Normally, orthologs encode polypeptides having the same or similar functions. As also used herein, the term "paralogs" refers to two nucleic acids that are related by duplication within a genome. Paralogs usually have different functions, but these functions may be related (Tatusov, R. L. et al., 1997, Science 278(5338): 631–637). Analogs, orthologs, and paralogs of a naturally occurring ITSRP can differ from the naturally occurring ITSRP by post-translational modifications, by amino acid sequence differences, or by both. Post-translational modifications include in vivo and in vitro chemical derivatization of polypeptides, e.g., acetylation, carboxylation, phosphorylation, or glycosylation, and such modifications may occur during polypeptide synthesis or processing or following treatment with isolated modifying enzymes. In particular, orthologs of the invention will generally exhibit at least 80–85%, more preferably, 85–90% or 90–95%, and most preferably 95%, 96%, 97%, 98%, or even 99% identity, or 100% sequence identity, with all or part of a naturally occurring ITSRP amino acid sequence, and will exhibit a function similar to an ITSRP. Preferably, an ITSRP ortholog of the present invention functions as a modulator of an environmental stress response in a plant and/or functions as an ion transporter. More preferably, an ITSRP ortholog increases the stress tolerance of a plant. In one embodiment, the ITSRP orthologs maintain the ability to participate in the metabolism of compounds necessary for the construction of cellular membranes in a plant, or in the transport of molecules across these membranes.

In addition to naturally-occurring variants of an ITSRP sequence that may exist in the population, the skilled artisan will further appreciate that changes can be introduced by mutation into a nucleotide sequence of SEQ ID NO:5, SEQ ID NO:8, SEQ ID NO:10, SEQ ID NO:12, SEQ ID NO:14, or SEQ ID NO:16, thereby leading to changes in the amino acid sequence of the encoded ITSRP, without altering the functional activity of the ITSRP. For example, nucleotide substitutions leading to amino acid substitutions at "non-essential" amino acid residues can be made in a sequence of SEQ ID NO:5, SEQ ID NO:8, SEQ ID NO:10, SEQ ID NO:12, SEQ ID NO:14, or SEQ ID NO:16. A "non-essential" amino acid residue is a residue that can be altered from the wild-type sequence of one of the ITSRPs without altering the activity of said ITSRP, whereas an "essential" amino acid residue is required for ITSRP activity. Other amino acid residues, however, (e.g., those that are not conserved or only semi-conserved in the domain having ITSRP activity) may not be essential for activity and thus are likely to be amenable to alteration without altering ITSRP activity.

Accordingly, another aspect of the invention pertains to nucleic acid molecules encoding ITSRPs that contain changes in amino acid residues that are not essential for ITSRP activity. Such ITSRPs differ in amino acid sequence from a sequence contained in SEQ ID NO:6, SEQ ID NO:9, SEQ ID NO:11, SEQ ID NO:13, SEQ ID NO:15, or SEQ ID NO:17, yet retain at least one of the ITSRP activities described herein. In one embodiment, the isolated nucleic acid molecule comprises a nucleotide sequence encoding a polypeptide, wherein the polypeptide comprises an amino acid sequence at least about 50% identical to an amino acid sequence of SEQ ID NO:6, SEQ ID NO:9, SEQ ID NO:11, SEQ ID NO:13, SEQ ID NO:15, or SEQ ID NO:17. Preferably, the polypeptide encoded by the nucleic acid molecule is at least about 50–60% identical to one of the sequences of SEQ ID NO:6, SEQ ID NO:9, SEQ ID NO:11, SEQ ID NO:13, SEQ ID NO:15, and SEQ ID NO:17, more preferably at least about 60–70% identical to one of the sequences of SEQ ID NO:6, SEQ ID NO:9, SEQ ID NO:11, SEQ ID NO:13, SEQ ID NO:15, and SEQ ID NO:17, even more preferably at least about 70–75%, 75–80%, 80–85%, 85–90%, or 90–95% identical to one of the sequences of SEQ ID NO:6, SEQ ID NO:9, SEQ ID NO:11, SEQ ID NO:13, SEQ ID NO:15, and SEQ ID NO:17, and most preferably at least about 96%, 97%, 98%, or 99% identical to one of the sequences of SEQ ID NO:6, SEQ ID NO:9, SEQ ID NO:11, SEQ ID NO:13, SEQ ID NO:15, and SEQ ID NO:17. The preferred ITSRP homologs of the present invention preferably participate in a stress tolerance response in a plant, or more particularly, participate in the transcription of a polypeptide involved in a stress tolerance response in a plant, and/or function as an ion transporter.

An isolated nucleic acid molecule encoding an ITSRP having sequence identity with a polypeptide sequence of SEQ ID NO:6, SEQ ID NO:9, SEQ ID NO:11, SEQ ID NO:13, SEQ ID NO:15, or SEQ ID NO:17 can be created by introducing one or more nucleotide substitutions, additions or deletions into a nucleotide sequence of SEQ ID NO:5, SEQ ID NO:8, SEQ ID NO:10, SEQ ID NO:12, SEQ ID NO:14, or SEQ ID NO:16, respectively, such that one or more amino acid substitutions, additions, or deletions are introduced into the encoded polypeptide. Mutations can be introduced into one of the sequences of SEQ ID NO:5, SEQ ID NO:8, SEQ ID NO:10, SEQ ID NO:12, SEQ ID NO:14, or SEQ ID NO:16 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Thus, a predicted nonessential amino acid residue in an ITSRP is preferably replaced with another amino acid residue from the same side chain family. Alternatively, in another embodiment, mutations can be introduced randomly along all or part of an ITSRP coding sequence, such as by saturation mutagenesis, and the resultant mutants can be screened for an ITSRP activity described herein to identify mutants that retain ITSRP activity. Following mutagenesis of one of the sequences of SEQ ID NO:5, SEQ ID NO:8, SEQ ID NO:10, SEQ ID NO:12, SEQ ID NO:14, or SEQ ID NO:16, the encoded polypeptide can be expressed recombinantly and the activity of the polypeptide can be determined by analyzing the stress tolerance of a plant expressing the polypeptide as described in Example 7.

Additionally, optimized ITSRP nucleic acids can be created. Preferably, an optimized ITSRP nucleic acid encodes an ITSRP that binds to a phosphate group and/or modulates a plant's tolerance to an environmental stress, and more preferably increases a plant's tolerance to an environmental stress upon its overexpression in the plant. As used herein, "optimized" refers to a nucleic acid that is genetically engineered to increase its expression in a given plant or animal. To provide plant optimized ITSRP nucleic acids, the DNA sequence of the gene can be modified to 1) comprise codons preferred by highly expressed plant genes; 2) comprise an A+T content in nucleotide base composition to that substantially found in plants; 3) form a plant initiation sequence; or 4) to eliminate sequences that cause destabilization, inappropriate polyadenylation, degradation and termination of RNA, or that form secondary structure hairpins or RNA splice sites. Increased expression of ITSRP nucleic acids in plants can be achieved by utilizing the distribution frequency of codon usage in plants in general or in a particular plant. Methods for optimizing nucleic acid expression in plants can be found in EPA 0359472; EPA 0385962; PCT Application No. WO 91/16432; U.S. Pat. No. 5,380,831; U.S. Pat. No. 5,436,391; Perlack et al., 1991, Proc. Natl. Acad. Sci. USA 88:3324–3328; and Murray et al., 1989, Nucleic Acids Res. 17:477–498.

As used herein, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell. The percent deviation of the frequency of preferred codon usage for a synthetic gene from that employed by a host cell is calculated first by determining the percent deviation of the frequency of usage of a single codon from that of the host cell followed by obtaining the average deviation over all codons. As defined herein, this calculation includes unique codons (i.e., ATG and TGG). In general terms, the overall average deviation of the codon usage of an optimized gene from that of a host cell is calculated using the equation $1A = n = 1Z \, X_n - Y_n X_n$ times $100 \, Z$ where $X_n$=frequency of usage for codon n in the host cell; $Y_n$=frequency of usage for codon n in the synthetic gene; n represents an individual codon that specifies an amino acid; and the total number of codons is Z. The overall deviation of the frequency of codon usage, A, for all amino acids should preferably be less than about 25%, and more preferably less than about 10%.

Hence, an ITSRP nucleic acid can be optimized such that its distribution frequency of codon usage deviates, preferably, no more than 25% from that of highly expressed plant genes and, more preferably, no more than about 10%. In addition, consideration is given to the percentage G+C content of the degenerate third base (monocotyledons appear to favor G+C in this position, whereas dicotyledons do not). It is also recognized that the XCG (where X is A, T, C, or G) nucleotide is the least preferred codon in dicots whereas the XTA codon is avoided in both monocots and dicots. Optimized ITSRP nucleic acids of this invention also preferably have CG and TA doublet avoidance indices closely approximating those of the chosen host plant (i.e., *Physcomitrella patens*, *Brassica napus*, *Glycine max*, or *Oryza sativa*). More preferably these indices deviate from that of the host by no more than about 10–15%.

In addition to the nucleic acid molecules encoding the ITSRPs described above, another aspect of the invention pertains to isolated nucleic acid molecules that are antisense thereto. Antisense polynucleotides are thought to inhibit gene expression of a target polynucleotide by specifically binding the target polynucleotide and interfering with transcription, splicing, transport, translation, and/or stability of the target polynucleotide. Methods are described in the prior art for targeting the antisense polynucleotide to the chromosomal DNA, to a primary RNA transcript, or to a processed mRNA. Preferably, the target regions include splice sites, translation initiation codons, translation termination codons, and other sequences within the open reading frame.

The term "antisense," for the purposes of the invention, refers to a nucleic acid comprising a polynucleotide that is sufficiently complementary to all or a portion of a gene, primary transcript, or processed mRNA, so as to interfere with expression of the endogenous gene. "Complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other. The term "antisense nucleic acid" includes single stranded RNA as well as double-stranded DNA expression cassettes that can be transcribed to produce an antisense RNA. "Active" antisense nucleic acids are antisense RNA molecules that are capable of selectively hybridizing with a primary transcript or mRNA encoding a polypeptide having at least 80% sequence identity with the polypeptide of SEQ ID NO:6, SEQ ID NO:9, SEQ ID NO:11, SEQ ID NO:13, SEQ ID NO:15, or SEQ ID NO:17.

The antisense nucleic acid can be complementary to an entire ITSRP coding strand, or to only a portion thereof. In one embodiment, an antisense nucleic acid molecule is antisense to a "coding region" of the coding strand of a nucleotide sequence encoding an ITSRP. The term "coding region" refers to the region of the nucleotide sequence comprising codons that are translated into amino acid residues. In another embodiment, the antisense nucleic acid molecule is antisense to a "noncoding region" of the coding strand of a nucleotide sequence encoding an ITSRP. The term "noncoding region" refers to 5' and 3' sequences that flank the coding region that are not translated into amino acids (i.e., also referred to as 5' and 3' untranslated regions). The antisense nucleic acid molecule can be complementary to the entire coding region of ITSRP mRNA, but more preferably is an oligonucleotide that is antisense to only a portion of the coding or noncoding region of ITSRP mRNA. For example, the antisense oligonucleotide can be complementary to the region surrounding the translation start site of ITSRP mRNA. An antisense oligonucleotide can be, for example, about 5, 10, 15, 20, 25, 30, 35, 40, 45, or 50 nucleotides in length. Typically, the antisense molecules of the present invention comprise an RNA having 60–100% sequence identity with at least 14 consecutive nucleotides of SEQ ID NO:5, SEQ ID NO:8, SEQ ID NO:10, SEQ ID NO:12, SEQ ID NO:14, or SEQ ID NO:16, or a polynucleotide encoding a polypeptide of SEQ ID NO:6, SEQ ID NO:9, SEQ ID NO:11, SEQ ID NO:13, SEQ ID NO:15, or SEQ ID NO:17. Preferably, the sequence identity will be at least 70%, more preferably at least 75%, 80%, 85%, 90%, 95%, or 98%, and most preferably 99%.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., 1987, Nucleic Acids. Res. 15:6625–6641). The antisense nucleic acid molecule can also comprise a 2'-o-methylribonucleotide (Inoue et al., 1987, Nucleic Acids Res. 15:6131–6148) or a chimeric RNA-DNA analogue (Inoue et al., 1987, FEBS Lett. 215: 327–330).

The antisense nucleic acid molecules of the invention are typically administered to a cell or generated in situ such that they hybridize with or bind to cellular mRNA and/or genomic DNA encoding an ITSRP to thereby inhibit expression of the polypeptide, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic (including plant) promoter are preferred.

As an alternative to antisense polynucleotides, ribozymes, sense polynucleotides, or double stranded RNA (dsRNA) can be used to reduce expression of an ITSRP polypeptide. As used herein, the term "ribozyme" refers to a catalytic RNA-based enzyme with ribonuclease activity that is capable of cleaving a single-stranded nucleic acid, such as an mRNA, to which it has a complementary region. Ribozymes (e.g., hammerhead ribozymes described in Haselhoff and Gerlach, 1988, Nature 334:585–591) can be used to catalytically cleave ITSRP mRNA transcripts to thereby inhibit translation of ITSRP mRNA. A ribozyme having specificity for an ITSRP-encoding nucleic acid can be designed based upon the nucleotide sequence of an ITSRP cDNA, as disclosed herein (i.e., SEQ ID NO:5, SEQ ID NO:8, SEQ ID NO:10, SEQ ID NO:12, SEQ ID NO:14, or SEQ ID NO:16) or on the basis of a heterologous sequence to be isolated according to methods taught in this invention. For example, a derivative of a Tetrahymena L-19 IVS RNA can be constructed in which the nucleotide sequence of the active site is complementary to the nucleotide sequence to be cleaved in an ITSRP-encoding mRNA. See, e.g., U.S. Pat. Nos. 4,987,071 and 5,116,742 to Cech et al. Alternatively, ITSRP mRNA can be used to select a catalytic RNA having a specific ribonuclease activity from a pool of RNA molecules. See, e.g., Bartel, D. and Szostak, J. W., 1993, Science 261:1411–1418. In preferred embodiments, the ribozyme will contain a portion having at least 7, 8, 9, 10, 12, 14, 16, 18, or 20 nucleotides, and more preferably 7 or 8 nucleotides, that have 100% complementarity to a portion of the target RNA. Methods for making ribozymes are known to those skilled in the art. See, e.g., U.S. Pat. Nos. 6,025,167; 5,773,260; and 5,496,698.

The term "dsRNA," as used herein, refers to RNA hybrids comprising two strands of RNA. The dsRNAs can be linear or circular in structure. In a preferred embodiment, dsRNA is specific for a polynucleotide encoding either the polypeptide of SEQ ID NO:6, SEQ ID NO:9, SEQ ID NO:11, SEQ ID NO:13, SEQ ID NO:15, or SEQ ID NO:17, or a polypeptide having at least 80% sequence identity with a polypeptide of SEQ ID NO:6, SEQ ID NO:9, SEQ ID NO:11, SEQ ID NO:13, SEQ ID NO:15, or SEQ ID NO:17. The hybridizing RNAs may be substantially or completely complementary. By "substantially complementary," is meant that when the two hybridizing RNAs are optimally aligned using the BLAST program as described above, the hybridizing portions are at least 95% complementary. Preferably, the dsRNA will be at least 100 base pairs in length. Typically, the hybridizing RNAs will be of identical length with no over hanging 5' or 3' ends and no gaps. However, dsRNAs having 5' or 3' overhangs of up to 100 nucleotides may be used in the methods of the invention.

The dsRNA may comprise ribonucleotides, ribonucleotide analogs such as 2'-O-methyl ribosyl residues, or combinations thereof. See, e.g., U.S. Pat. Nos. 4,130,641 and 4,024,222. A dsRNA polyriboinosinic acid:polyribocytidylic acid is described in U.S. Pat. No. 4,283,393. Methods for making and using dsRNA are known in the art. One method comprises the simultaneous transcription of two complementary DNA strands, either in vivo, or in a single in vitro reaction mixture. See, e.g., U.S. Pat. No. 5,795,715. In one embodiment, dsRNA can be introduced into a plant or plant cell directly by standard transformation procedures. Alternatively, dsRNA can be expressed in a plant cell by transcribing two complementary RNAs.

Other methods for the inhibition of endogenous gene expression, such as triple helix formation (Moser et al., 1987, Science 238:645–650 and Cooney et al., 1988, Science 241:456–459) and co-suppression (Napoli et al., 1990, The Plant Cell 2:279–289) are known in the art. Partial and full-length cDNAs have been used for the co-suppression of endogenous plant genes. See, e.g., U.S. Pat. Nos. 4,801,340, 5,034,323, 5,231,020, and 5,283,184; Van der Kroll et al., 1990, The Plant Cell 2:291–299; Smith et al., 1990, Mol. Gen. Genetics 224:477–481; and Napoli et al., 1990, The Plant Cell 2:279–289.

For sense suppression, it is believed that introduction of a sense polynucleotide blocks transcription of the corresponding target gene. The sense polynucleotide will have at least 65% sequence identity with the target plant gene or RNA. Preferably, the percent identity is at least 80%, 90%, 95%, or more. The introduced sense polynucleotide need not be full length relative to the target gene or transcript. Preferably, the sense polynucleotide will have at least 65% sequence identity with at least 100 consecutive nucleotides of SEQ ID NO:5, SEQ ID NO:8, SEQ ID NO:10, SEQ ID NO:12, SEQ ID NO:14, or SEQ ID NO:16. The regions of identity can comprise introns and/or exons and untranslated regions. The introduced sense polynucleotide may be present in the plant cell transiently, or may be stably integrated into a plant chromosome or extrachromosomal replicon.

Alternatively, ITSRP gene expression can be inhibited by targeting nucleotide sequences complementary to the regulatory region of an ITSRP nucleotide sequence (e.g., an ITSRP promoter and/or enhancer) to form triple helical structures that prevent transcription of an ITSRP gene in target cells. See generally, Helene, C., 1991, Anticancer Drug Des. 6(6):569–84; Helene, C. et al., 1992, Ann. N.Y. Acad. Sci. 660:27–36; and Maher, L. J., 1992, Bioassays 14(12):807–15.

In addition to the ITSRP nucleic acids and polypeptides described above, the present invention encompasses these nucleic acids and polypeptides attached to a moiety. These moieties include, but are not limited to, detection moieties, hybridization moieties, purification moieties, delivery moieties, reaction moieties, binding moieties, and the like. A typical group of nucleic acids having moieties attached are probes and primers. Probes and primers typically comprise a substantially isolated oligonucleotide. The oligonucleotide typically comprises a region of nucleotide sequence that hybridizes under stringent conditions to at least about 12, preferably about 25, more preferably about 40, 50, or 75 consecutive nucleotides of a sense strand of one of the sequences set forth in SEQ ID NO:5, SEQ ID NO:8, SEQ ID NO:10, SEQ ID NO:12, SEQ ID NO:14, or SEQ ID NO:16; an anti-sense sequence of one of the sequences set forth in SEQ ID NO:5, SEQ ID NO:8, SEQ ID NO:10, SEQ ID NO:12, SEQ ID NO:14, or SEQ ID NO:16; or naturally occurring mutants thereof. Primers based on a nucleotide sequence of SEQ ID NO:5, SEQ ID NO:8, SEQ ID NO:10, SEQ ID NO:12, SEQ ID NO:14, or SEQ ID NO:16 can be used in PCR reactions to clone ITSRP homologs. Probes based on the ITSRP nucleotide sequences can be used to detect transcripts or genomic sequences encoding the same or substantially identical polypeptides. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express an ITSRP, such as by measuring a level of an ITSRP-encoding nucleic acid, in a sample of cells, e.g., detecting ITSRP mRNA levels or determining whether a genomic ITSRP gene has been mutated or deleted.

In particular, a useful method to ascertain the level of transcription of the gene (an indicator of the amount of mRNA available for translation to the gene product) is to perform a Northern blot (For reference, see, for example, Ausubel et al., 1988, Current Protocols in Molecular Biology, Wiley: New York). The information from a Northern blot at least partially demonstrates the degree of transcription of the transformed gene. Total cellular RNA can be prepared from cells, tissues, or organs by several methods, all well-known in the art, such as that described in Bormann, E. R. et al., 1992, Mol. Microbiol. 6:317–326. To assess the presence or relative quantity of polypeptide translated from this mRNA, standard techniques, such as a Western blot, may be employed. These techniques are well known to one of ordinary skill in the art. (See, for example, Ausubel et al., 1988, Current Protocols in Molecular Biology, Wiley: New York).

The invention further provides an isolated recombinant expression vector comprising an ITSRP nucleic acid as described above, wherein expression of the vector in a host cell results in increased tolerance to environmental stress as compared to a wild type variety of the host cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. As used herein with respect to a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). Such regulatory sequences are described, for example, in Goeddel, Gene Expression Technology: Methods in Enzymology 185, Academic Press, San Diego, Calif. (1990) and Gruber and Crosby, in: Methods in Plant Molecular Biology and Biotechnology, eds. Glick and Thompson, Chapter 7, 89–108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., ITSRPs, mutant forms of ITSRPs, fusion polypeptides, etc.).

The recombinant expression vectors of the invention can be designed for expression of ITSRPs in prokaryotic or eukaryotic cells. For example, ITSRP genes can be expressed in bacterial cells such as *C. glutamicum*, insect cells (using baculovirus expression vectors), yeast and other fungal cells (See Romanos, M. A. et al., 1992, Foreign gene expression in yeast: a review, Yeast 8:423–488; van den Hondel, C. A. M. J. J. et al., 1991, Heterologous gene expression in filamentous fungi, in: More Gene Manipulations in Fungi, J. W. Bennet & L. L. Lasure, eds., p. 396–428: Academic Press: San Diego; and van den Hondel, C. A. M. J. J. & Punt, P. J., 1991, Gene transfer systems and vector development for filamentous fungi, in: Applied Molecular Genetics of Fungi, Peberdy, J. F. et al., eds., p. 1–28, Cambridge University Press: Cambridge), algae (Falciatore et al., 1999, Marine Biotechnology 1(3):239–251), ciliates of the types: Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella, and *Stylonychia*, especially of the genus *Stylonychia lemnae* with vectors following a transformation method as described in PCT Application No. WO 98/01572, and multicellular plant cells (See Schmidt, R. and Willmitzer, L., 1988, High efficiency *Agrobacterium tumefaciens*-mediated transformation of *Arabidopsis thaliana* leaf and cotyledon explants, Plant Cell Rep. 583–586; Plant Molecular Biology and Biotechnology, C Press, Boca Raton, Fla., chapter 6/7, S.71–119 (1993); F. F. White, B. Jenes et al., Techniques for Gene Transfer, in: Transgenic Plants, Vol. 1, Engineering and Utilization, eds. Kung und R. Wu, 128–43, Academic Press: 1993; Potrykus, 1991, Annu. Rev. Plant Physiol. Plant Molec. Biol. 42:205–225 and references cited therein), or mammalian cells. Suitable host cells are discussed further in Goeddel, Gene Expression Technology: Methods in Enzymology 185, Academic Press: San Diego, Calif. (1990). Alternatively, the recombinant expression vector can be transcribed and translated in vitro, for example using T7 promoter regulatory sequences and T7 polymerase.

Expression of polypeptides in prokaryotes is most often carried out with vectors containing constitutive or inducible promoters directing the expression of either fusion or non-fusion polypeptides. Fusion vectors add a number of amino acids to a polypeptide encoded therein, usually to the amino terminus of the recombinant polypeptide but also to the C-terminus or fused within suitable regions in the polypeptides. Such fusion vectors typically serve three purposes: 1) to increase expression of a recombinant polypeptide; 2) to increase the solubility of a recombinant polypeptide; and 3) to aid in the purification of a recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin, and enterokinase.

Typical fusion expression vectors include pGEX (Pharmacia Biotech Inc; Smith, D. B. and Johnson, K. S., 1988, Gene 67:31–40), pMAL (New England Biolabs, Beverly, Mass.), and pRIT5 (Pharmacia, Piscataway, N.J.) which fuse glutathione S-transferase (GST), maltose E binding polypeptide, or polypeptide A, respectively, to the target recombinant polypeptide. In one embodiment, the coding sequence of the ITSRP is cloned into a pGEX expression vector to create a vector encoding a fusion polypeptide comprising, from the N-terminus to the C-terminus, GST-thrombin cleavage site-X polypeptide. The fusion polypeptide can be purified by affinity chromatography using glutathione-agarose resin. Recombinant ITSRP unfused to GST can be recovered by cleavage of the fusion polypeptide with thrombin.

Examples of suitable inducible non-fusion *E. coli* expression vectors include pTrc (Amann et al., 1988, Gene 69:301–315) and pET 11d (Studier et al., Gene Expression Technology: Methods in Enzymology 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174 (DE3) from a resident λ prophage harboring a T7 gn1 gene under the transcriptional control of the lacUV 5 promoter.

One strategy to maximize recombinant polypeptide expression is to express the polypeptide in a host bacteria with an impaired capacity to proteolytically cleave the recombinant polypeptide (Gottesman, S., Gene Expression Technology: Methods in Enzymology 185, Academic Press, San Diego, Calif. (1990) 119–128). Another strategy is to alter the sequence of the nucleic acid to be inserted into an expression vector so that the individual codons for each amino acid are those preferentially utilized in the bacterium chosen for expression, such as *C. glutamicum* (Wada et al., 1992, Nucleic Acids Res. 20:2111–2118). Such alteration of nucleic acid sequences of the invention can be carried out by standard DNA synthesis techniques.

In another embodiment, the ITSRP expression vector is a yeast expression vector. Examples of vectors for expression in yeast *S. cerevisiae* include pYepSec1 (Baldari, et al., 1987, EMBO J. 6:229–234), pMFa (Kuijan and Herskowitz, 1982, Cell 30:933–943), pJRY88 (Schultz et al., 1987, Gene 54:113–123), and pYES2 (Invitrogen Corporation, San Diego, Calif.). Vectors and methods for the construction of vectors appropriate for use in other fungi, such as the filamentous fungi, include those detailed in: van den Hondel, C. A. M. J. J. & Punt, P. J., 1991, "Gene transfer systems and vector development for filamentous fungi," in: Applied Molecular Genetics of Fungi, J. F. Peberdy, et al., eds., p. 1–28, Cambridge University Press: Cambridge.

Alternatively, the ITSRPs of the invention can be expressed in insect cells using baculovirus expression vectors. Baculovirus vectors available for expression of polypeptides in cultured insect cells (e.g., Sf 9 cells) include the pAc series (Smith et al., 1983, Mol. Cell Biol. 3:2156–2165) and the pVL series (Lucklow and Summers, 1989, Virology 170:31–39).

In yet another embodiment, an ITSRP nucleic acid of the invention is expressed in mammalian cells using a mammalian expression vector. Examples of mammalian expression vectors include pCDM8 (Seed, B., 1987, Nature 329:840) and pMT2PC (Kaufman et al., 1987, EMBO J. 6:187–195). When used in mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook, J., Fritsh, E. F., and Maniatis, T. Molecular Cloning: A Laboratory Manual. latest ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, Genes Dev. 1:268–277), lymphoid-specific promoters (Calame and Eaton, 1988, Adv. Immunol. 43:235–275), in particular promoters of T cell receptors (Winoto and Baltimore, 1989, EMBO J. 8:729–733), and immunoglobulins (Banerji et al., 1983, Cell 33:729–740; Queen and Baltimore, 1983, Cell 33:741–748), neuron-specific promoters (e.g., the neurofilament promoter; Byrne and Ruddle, 1989, PNAS 86:5473–5477), pancreas-specific promoters (Edlund et al., 1985, Science 230:912–916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss, 1990, Science 249:374–379) and the fetopolypeptide promoter (Campes and Tilghman, 1989, Genes Dev. 3:537–546).

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics or herbicides) is generally introduced into the host cells along with the gene of interest. Preferred selectable markers include those that confer resistance to drugs, such as G418, hygromycin, and methotrexate, or in plants that confer resistance towards an herbicide such as glyphosate, glufosinate, or imidazolinone. Nucleic acid molecules encoding a selectable marker can be introduced into a host cell on the same vector as that encoding an ITSRP or can be introduced on a separate vector. Cells stably transfected with the introduced nucleic acid molecule can be identified by, for example, herbicide selection (e.g., cells that have incorporated the selectable marker gene will survive, while the other cells die).

In a preferred embodiment of the present invention, the ITSRPs are expressed in plants and plants cells such as unicellular plant cells (e.g. algae) (See Falciatore et al., 1999, Marine Biotechnology 1(3):239–251 and references therein) and plant cells from higher plants (e.g., the spermatophytes, such as crop plants). An ITSRP may be "introduced" into a plant cell by any means, including transfection, transformation or transduction, electroporation, particle bombardment, agroinfection, and the like. One transformation method known to those of skill in the art is the dipping of a flowering plant into an Agrobacteria solution, wherein the Agrobacteria contain the ITSRP nucleic acid, followed by breeding of the transformed gametes.

Other suitable methods for transforming or transfecting host cells including plant cells can be found in Sambrook, et al. (Molecular Cloning: A Laboratory Manual. latest ed., Cold Spring Harbor Laboratory, Cold Spring Harbor Laboratory Press, Cold Spring Harbor, N.Y., 1989) and other laboratory manuals such as Methods in Molecular Biology, 1995, Vol. 44, Agrobacterium protocols, ed: Gartland and Davey, Humana Press, Totowa, N.J. As biotic and abiotic stress tolerance is a general trait wished to be inherited into a wide variety of plants like maize, wheat, rye, oat, triticale, rice, barley, soybean, peanut, cotton, rapeseed and canola, manihot, pepper, sunflower and tagetes, solanaceous plants like potato, tobacco, eggplant, and tomato, Vicia species, pea, alfalfa, bushy plants (coffee, cacao, tea), Salix species, trees (oil palm, coconut), perennial grasses, and forage crops, these crop plants are also preferred target plants for a genetic engineering as one further embodiment of the present invention. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover, and Sweet Clover.

In one embodiment of the present invention, transfection of an ITSRP into a plant is achieved by *Agrobacterium* mediated gene transfer. *Agrobacterium* mediated plant transformation can be performed using for example the GV3101 (pMP90) (Koncz and Schell, 1986, Mol. Gen. Genet. 204: 383–396) or LBA4404 (Clontech) *Agrobacterium tumefaciens* strain. Transformation can be performed by standard transformation and regeneration techniques (Deblaere et al., 1994, Nucl. Acids. Res. 13:4777–4788; Gelvin, Stanton B. and Schilperoort, Robert A, Plant Molecular Biology Manual, $2^{nd}$ Ed.—Dordrecht: Kluwer Academic Publ., 1995.—in Sect., Ringbuc Zentrale Signatur: BT11-P ISBN 0-7923-2731-4; Glick, Bernard R.; Thompson, John E., Methods in Plant Molecular Biology and Biotechnology, Boca Raton: CRC Press, 1993 360 S., ISBN 0-8493-5164-2). For example, rapeseed can be transformed via cotyledon or hypocotyl transformation (Moloney et al., 1989, Plant Cell Report 8:238–242; De Block et al., 1989, Plant Physiol. 91:694–701). Use of antibiotics for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., 1994, Plant Cell Report 13:282–285. Additionally, transformation of soybean can be performed using for example a technique described in European Patent No. 0424 047, U.S. Pat. No. 5,322,783, European Patent No. 0397 687, U.S. Pat. No. 5,376,543, or U.S. Pat. No. 5,169, 770. Transformation of maize can be achieved by particle bombardment, polyethylene glycol mediated DNA uptake, or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387, and a specific example of wheat transformation can be found in PCT Application No. WO 93/07256.

According to the present invention, the introduced ITSRP may be maintained in the plant cell stably if it is incorporated into a non-chromosomal autonomous replicon or integrated into the plant chromosomes. Alternatively, the introduced ITSRP may be present on an extra-chromosomal non-replicating vector and may be transiently expressed or transiently active.

In one embodiment, a homologous recombinant microorganism can be created wherein the ITSRP is integrated into a chromosome, a vector is prepared which contains at least a portion of an ITSRP gene into which a deletion, addition, or substitution has been introduced to thereby alter, e.g., functionally disrupt, the ITSRP gene. Preferably, the ITSRP gene is a *Physcomitrella patens, Brassica napus, Glycine max*, or *Oryza sativa* ITSRP gene, but it can be a homolog from a related plant or even from a mammalian, yeast, or insect source. In one embodiment, the vector is designed such that, upon homologous recombination, the endogenous ITSRP gene is functionally disrupted (i.e., no longer encodes a functional polypeptide; also referred to as a knock-out vector). Alternatively, the vector can be designed such that, upon homologous recombination, the endogenous ITSRP gene is mutated or otherwise altered but still encodes a functional polypeptide (e.g., the upstream regulatory region can be altered to thereby alter the expression of the endogenous ITSRP). To create a point mutation via homologous recombination, DNA-RNA hybrids can be used in a technique known as chimeraplasty (Cole-Strauss et al., 1999, Nucleic Acids Research 27(5):1323–1330 and Kmiec, 1999, Gene Therapy American Scientist 87(3):240–247). Homologous recombination procedures in *Physcomitrella patens* are also well known in the art and are contemplated for use herein.

Whereas in the homologous recombination vector, the altered portion of the ITSRP gene is flanked at its 5' and 3' ends by an additional nucleic acid molecule of the ITSRP gene to allow for homologous recombination to occur between the exogenous ITSRP gene carried by the vector and an endogenous ITSRP gene, in a microorganism or plant. The additional flanking ITSRP nucleic acid molecule is of sufficient length for successful homologous recombination with the endogenous gene. Typically, several hundreds of base pairs up to kilobases of flanking DNA (both at the 5' and 3' ends) are included in the vector (See e.g., Thomas, K. R., and Capecchi, M. R., 1987, Cell 51:503 for a description of homologous recombination vectors or Strepp et al., 1998, PNAS, 95(8):4368–4373 for cDNA based recombination in *Physcomitrella patens*). The vector is introduced into a microorganism or plant cell (e.g., via polyethylene glycol mediated DNA), and cells in which the introduced ITSRP gene has homologously recombined with the endogenous ITSRP gene are selected using art-known techniques.

In another embodiment, recombinant microorganisms can be produced that contain selected systems that allow for regulated expression of the introduced gene. For example, inclusion of an ITSRP gene on a vector placing it under control of the lac operon permits expression of the ITSRP gene only in the presence of IPTG. Such regulatory systems are well known in the art.

Whether present in an extra-chromosomal non-replicating vector or a vector that is integrated into a chromosome, the ITSRP polynucleotide preferably resides in a plant expression cassette. A plant expression cassette preferably contains regulatory sequences capable of driving gene expression in plant cells that are operatively linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984, EMBO J. 3:835) or functional equivalents thereof, but also all other terminators functionally active in plants are suitable. As plant gene expression is very often not limited on transcriptional levels, a plant expression cassette preferably contains other operatively linked sequences like translational enhancers such as the overdrive-sequence containing the 5'-untranslated leader sequence from tobacco mosaic virus enhancing the polypeptide per RNA ratio (Gallie et al., 1987, Nucl. Acids Research 15:8693–8711). Examples of plant expression vectors include those detailed in: Becker, D., Kemper, E., Schell, J. and Masterson, R., 1992, New plant binary vectors with selectable markers located proximal to the left border, Plant Mol. Biol. 20: 1195–1197; and Bevan, M. W., 1984, Binary *Agrobacterium* vectors for plant transformation, Nucl. Acid. Res. 12:8711–8721; Vectors for Gene Transfer in Higher Plants; in: Transgenic Plants, Vol. 1, Engineering and Utilization, eds.: Kung and R. Wu, Academic Press, 1993, S. 15–38.

Plant gene expression should be operatively linked to an appropriate promoter conferring gene expression in a timely, cell specific, or tissue specific manner. Promoters useful in the expression cassettes of the invention include any promoter that is capable of initiating transcription in a plant cell. Such promoters include, but are not limited to, those that can be obtained from plants, plant viruses, and bacteria that contain genes that are expressed in plants, such as *Agrobacterium* and *Rhizobium*.

The promoter may be constitutive, inducible, developmental stage-preferred, cell type-preferred, tissue-preferred, or organ-preferred. Constitutive promoters are active under most conditions. Examples of constitutive promoters include the CaMV 19S and 35 S promoters (Odell et al., 1985, Nature 313:810–812), the sX CaMV 35S promoter (Kay et al., 1987, Science 236:1299–1302) the Sep1 promoter, the rice actin promoter (McElroy et al., 1990, Plant Cell 2:163–171), the *Arabidopsis* actin promoter, the ubiquitan promoter (Christensen et al., 1989, Plant Molec. Biol. 18:675–689), pEmu (Last et al., 1991, Theor. Appl. Genet. 81:581–588), the figwort mosaic virus 35S promoter, the Smas promoter (Velten et al., 1984, EMBO J 3:2723–2730), the GRP1–8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) promoter, and the like.

Inducible promoters are preferentially active under certain environmental conditions, such as the presence or absence of a nutrient or metabolite, heat or cold, light, pathogen attack, anaerobic conditions, and the like. For example, the hsp80 promoter from *Brassica* is induced by heat shock; the PPDK promoter is induced by light; the PR-1 promoter from tobacco, *Arabidopsis*, and maize are inducible by infection with a pathogen; and the Adh1 promoter is induced by hypoxia and cold stress. Plant gene expression can also be facilitated via an inducible promoter (For review, see Gatz, 1997, Annu. Rev. Plant Physiol. Plant Mol. Biol. 48:89–108). Chemically inducible promoters are especially suitable if gene expression is wanted to occur in a time specific manner. Examples of such promoters are a salicylic acid inducible promoter (PCT Application No. WO 95/19443), a tetracycline inducible promoter (Gatz et al., 1992, Plant J. 2:397–404), and an ethanol inducible promoter (PCT Application No. WO 93/21334).

In one preferred embodiment of the present invention, the inducible promoter is a stress-inducible promoter. For the purposes of the invention, stress inducible promoters are preferentially active under one or more of the following stresses: sub-optimal conditions associated with salinity, drought, temperature, metal, chemical, pathogenic, and oxidative stresses. Stress inducible promoters include, but are not limited to, Cor78 (Chak et al., 2000, Planta 210:875–883; Hovath et al., 1993, Plant Physiol. 103:1047–1053), Cor15a (Artus et al., 1996, PNAS 93(23): 13404–09), Rci2A (Medina et al., 2001, Plant Physiol. 125:1655–66; Nylander et al., 2001, Plant Mol. Biol.

45:341–52; Navarre and Goffeau, 2000, EMBO J. 19:2515–24; Capel et al., 1997, Plant Physiol. 115:569–76), Rd22 (Xiong et al., 2001, Plant Cell 13:2063–83; Abe et al., 1997, Plant Cell 9:1859–68; Iwasaki et al., 1995, Mol. Gen. Genet. 247:391–8), cDet6 (Lang and Palve, 1992, Plant Mol. Biol. 20:951–62), ADH1 (Hoeren et al., 1998, Genetics 149:479–90), KAT1 (Nakamura et al., 1995, Plant Physiol. 109:371–4), KST1 (Müller-Röber et al., 1995, EMBO 14:2409–16), Rha1 (Terryn et Plant Cell 5:1761–9; Terryn et al., 1992, FEBS Lett. 299(3):287–90), ARSK1 (Atkinson et al., 1997, GenBank Accession # L22302, and PCT Application No. WO 97/20057), PtxA (Plesch et al., GenBank Accession # X67427), SbHRGP3 (Ahn et al., 1996, Plant Cell 8:1477–90), GH3 (Liu et al., 1994, Plant Cell 6:645–57), the pathogen inducible PRP1-gene promoter (Ward et al., 1993, Plant. Mol. Biol. 22:361–366), the heat inducible hsp80-promoter from tomato (U.S. Pat. No. 5,187, 267), cold inducible alpha-amylase promoter from potato (PCT Application No. WO 96/12814), or the wound-inducible pinII-promoter (European Patent No. 375091). For other examples of drought, cold, and salt-inducible promoters, such as the RD29A promoter, see Yamaguchi-Shinozalei et al., 1993, Mol. Gen. Genet. 236:331–340.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, and leaf-preferred, stigma-preferred, pollen-preferred, anther-preferred, a petal-preferred, sepal-preferred, pedicel-preferred, silique-preferred, stem-preferred, root-preferred promoters, and the like. Seed pre-ferred promoters are preferentially expressed during seed development and/or germination. For example, seed pre-ferred promoters can be embryo-preferred, endosperm pre-ferred, and seed coat-preferred. See Thompson et al., 1989, BioEssays 10:108. Examples of seed preferred promoters include, but are not limited to, cellulose synthase (ce1A), Cim1, gamma-zein, globulin-1, maize 19 kD zein (cZ19BT), and the like.

Other suitable tissue-preferred or organ-preferred promoters include the napin-gene promoter from rapeseed (U.S. Pat. No. 5,608,152), the USP-promoter from Vicia faba (Baeumlein et al., 1991, Mol. Gen. Genet. 225(3):459–67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980), or the legumin B4 promoter (LeB4; Baeumlein et al., 1992, Plant Journal, 2(2):233–9), as well as promoters conferring seed specific expression in monocot plants like maize, barley, wheat, rye, rice, etc. Suitable promoters to note are the lpt2 or lpt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene, and rye secalin gene).

Other promoters useful in the expression cassettes of the invention include, but are not limited to, the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2, and bronze promoters, the Zm13 promoter (U.S. Pat. No. 5,086, 169), the maize polygalacturonase promoters (PG) (U.S. Pat. Nos. 5,412,085 and 5,545,546), and the SGB6 promoter (U.S. Pat. No. 5,470,359), as well as synthetic or other natural promoters.

Additional flexibility in controlling heterologous gene expression in plants may be obtained by using DNA binding domains and response elements from heterologous sources (i.e., DNA binding domains from non-plant sources). An example of such a heterologous DNA binding domain is the LexA DNA binding domain (Brent and Ptashne, 1985, Cell 43:729–736).

The invention further provides a recombinant expression vector comprising an ITSRP DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to an ITSRP mRNA. Regulatory sequences operatively linked to a nucleic acid molecule cloned in the antisense orientation can be chosen which direct the continuous expression of the antisense RNA molecule in a variety of cell types. For instance, viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus wherein antisense nucleic acids are produced under the control of a high efficiency regulatory region. The activity of the regulatory region can be determined by the cell type into which the vector is introduced. For a discussion of the regulation of gene expression using antisense genes, see Weintraub, H. et al., 1986, Antisense RNA as a molecular tool for genetic analysis, Reviews—Trends in Genetics, Vol. 1(1), and Mol et al., 1990, FEBS Letters 268:427–430.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, an ITSRP can be expressed in bacterial cells such as *C. glutamicum*, insect cells, fungal cells, or mammalian cells (such as Chinese hamster ovary cells (CHO) or COS cells), algae, ciliates, plant cells, fungi, or other microorganisms like *C. glutamicum*. Other suitable host cells are known to those skilled in the art.

A host cell of the invention, such as a prokaryotic or eukaryotic host cell in culture, can be used to produce (i.e., express) an ITSRP. Accordingly, the invention further provides methods for producing ITSRPs using the host cells of the invention. In one embodiment, the method comprises culturing the host cell of invention (into which a recombinant expression vector encoding an ITSRP has been introduced, or into which genome has been introduced a gene encoding a wild-type or altered ITSRP ) in a suitable medium until the ITSRP is produced. In another embodiment, the method further comprises isolating ITSRPs from the medium or the host cell.

Another aspect of the invention pertains to isolated ITSRPs, and biologically active portions thereof. An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of ITSRP in which the polypeptide is separated from some of the cellular components of the cells in which it is naturally or recombinantly produced. In one embodiment, the language "substantially free of cellular material" includes preparations of an ITSRP having less than about 30% (by dry weight) of non-ITSRP material (also referred to herein as a "contaminating polypeptide"), more preferably less than about 20% of non-ITSRP material, still more preferably less than about 10% of non-ITSRP material, and most preferably less than about 5% non-ITSRP material.

When the ITSRP or biologically active portion thereof is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of ITSRP in which the polypeptide is separated from chemical precursors or other chemicals that are involved in the synthesis of the polypeptide. In one embodiment, the language "substantially free of chemical precursors or other chemicals" includes preparations of an ITSRP having less than about 30% (by dry weight) of chemical precursors or non-ITSRP chemicals, more preferably less than about 20% chemical precursors or non-ITSRP chemicals, still more preferably less than about 10% chemical precursors or non-ITSRP chemicals, and most preferably less than about 5% chemical precursors or non-ITSRP chemicals. In preferred embodiments, isolated polypeptides, or biologically active portions thereof, lack contaminating polypeptides from the same organism from which the ITSRP is derived. Typically, such polypeptides are produced by recombinant expression of, for example, a *Physcomitrella patens, Brassica napus, Glycine max,* or *Oryza sativa* ITSRP in plants other than *Physcomitrella patens, Brassica napus, Glycine max,* or *Oryza sativa*, or microorganisms such as *C. glutamicum*, ciliates, algae, or fungi.

The nucleic acid molecules, polypeptides, polypeptide homologs, fusion polypeptides, primers, vectors, and host cells described herein can be used in one or more of the following methods: identification of *Physcomitrella patens, Brassica napus, Glycine max,* or *Oryza sativa* and related organisms; mapping of genomes of organisms related to *Physcomitrella patens, Brassica napus, Glycine max,* or *Oryza sativa*; identification and localization of *Physcomitrella patens, Brassica napus, Glycine max,* or *Oryza sativa* sequences of interest; evolutionary studies; determination of ITSRP regions required for function; modulation of an ITSRP activity; modulation of the metabolism of one or more cell functions; modulation of the transmembrane transport of one or more compounds; modulation of stress resistance; and modulation of expression of ITSRP nucleic acids. In one embodiment of these methods, the ITSRP functions as an active potassium transport protein. In another embodiment of these methods, the ITSRP functions as a zinc transporter.

The moss *Physcomitrella patens* represents one member of the mosses. It is related to other mosses such as *Ceratodon purpureus* that is capable of growth in the absence of light. Mosses like Ceratodon and *Physcomitrella* share a high degree of sequence identity on the DNA sequence and polypeptide level allowing the use of heterologous screening of DNA molecules with probes evolving from other mosses or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference points for the mapping of moss genomes, or of genomes of related organisms.

The ITSRP nucleic acid molecules of the invention have a variety of uses. Most importantly, the nucleic acid and amino acid sequences of the present invention can be used to transform plants, thereby inducing tolerance to stresses such as drought, high salinity, and cold. The present invention therefore provides a transgenic plant transformed by an ITSRP nucleic acid, wherein expression of the nucleic acid sequence in the plant results in increased tolerance to environmental stress as compared to a wild type variety of the plant. The transgenic plant can be a monocot or a dicot. The invention further provides that the transgenic plant can be selected from maize, wheat, rye, oat, triticale, rice, barley, soybean, peanut, cotton, rapeseed, canola, manihot, pepper, sunflower, tagetes, solanaceous plants, potato, tobacco, eggplant, tomato, Vicia species, pea, alfalfa, coffee, cacao, tea, Salix species, oil palm, coconut, perennial grass, and forage crops, for example.

In particular, the present invention describes using the expression of PpAKT-2 and PpZT-1 of *Physcomitrella patens*; BnAKT-2 of *Brassica napus*; GmZT-1 and GmZT-2 of *Glycine max*; and OsZT-1 of *Oryza sativa* to engineer drought-tolerant, salt-tolerant, and/or cold-tolerant plants. This strategy has herein been demonstrated for *Arabidopsis thaliana*, Rapeseed/Canola, soybeans, corn, and wheat, but its application is not restricted to these plants. Accordingly, the invention provides a transgenic plant containing an ITSRP such as PpAKT-2 as defined in SEQ ID NO:6, PpZT-1 as defined in SEQ ID NO:9, BnAKT-2 as defined in SEQ ID NO:11, GmZT-1 as defined in SEQ ID NO:13, GmZT-2 as defined in SEQ ID NO:15, and OsZT-1 as defined in SEQ ID NO:17, wherein the plant has an increased tolerance to an environmental stress selected from one or more of the group consisting of drought, increased salt, or decreased or increased temperature. In preferred embodiments, the environmental stress is drought or decreased temperature.

Accordingly, the invention provides a method of producing a transgenic plant with an ITSRP coding nucleic acid, wherein expression of the nucleic acid(s) in the plant results in increased tolerance to environmental stress as compared to a wild type variety of the plant comprising: (a) introducing into a plant cell an expression vector comprising an ITSRP nucleic acid, and (b) generating from the plant cell a transgenic plant with a increased tolerance to environmental stress as compared to a wild type variety of the plant. The plant cell includes, but is not limited to, a protoplast, gamete producing cell, and a cell that regenerates into a whole plant. As used herein, the term "transgenic" refers to any plant, plant cell, callus, plant tissue, or plant part, that contains all or part of at least one recombinant polynucleotide. In many cases, all or part of the recombinant polynucleotide is stably integrated into a chromosome or stable extra-chromosomal element, so that it is passed on to successive generations. In preferred embodiments, the ITSRP nucleic acid encodes a protein comprising the polypeptide of SEQ ID NO:6, SEQ ID NO:9, SEQ ID NO:11, SEQ ID NO:13, SEQ ID NO:15, or SEQ ID NO:17.

The present invention also provides a method of modulating a plant's tolerance to an environmental stress comprising, modifying the expression of an ITSRP coding nucleic acid in the plant. The plant's tolerance to the environmental stress can be increased or decreased as achieved by increasing or decreasing the expression of an ITSRP, respectively. Preferably, the plant's tolerance to the environmental stress is increased by increasing expression of an ITSRP. Expression of an ITSRP can be modified by any method known to those of skill in the art. The methods of increasing expression of ITSRPs can be used wherein the plant is either transgenic or not transgenic. In cases when the plant is transgenic, the plant can be transformed with a vector containing any of the above described ITSRP coding nucleic acids, or the plant can be transformed with a promoter that directs expression of native ITSRP in the plant, for example. The invention provides that such a promoter can be tissue preferred, developmentally regulated, stress inducible, or a combination thereof. Alternatively, non-transgenic plants can have native ITSRP expression modified by inducing a native promoter. The expression of PpAKT-2 as defined in SEQ ID NO:5, PpZT-1 as defined in SEQ ID NO:8, BnAKT-2 as defined in SEQ ID NO:10, GmZT-1 as defined in SEQ ID NO:12, GmZT-2 as defined in SEQ ID NO:14, or OsZT-1 as defined in SEQ ID NO:16 in target plants can be accomplished by, but is not limited to, one of the following examples: (a) constitutive promoter, (b) stress-inducible promoter, (c) chemical-induced promoter, and (d) engineered promoter overexpression with, for example, zinc-finger derived transcription factors (Greisman and Pabo, 1997, Science 275:657).

In a preferred embodiment, transcription of the ITSRP is modulated using zinc-finger derived transcription factors (ZFPs) as described in Greisman and Pabo, 1997, Science 275:657 and manufactured by Sangamo Biosciences, Inc. These ZFPs comprise both a DNA recognition domain and a functional domain that causes activation or repression of a target nucleic acid such as an ITSRP nucleic acid. Therefore, activating and repressing ZFPs can be created that specifically recognize the ITSRP promoters described above and used to increase or decrease ITSRP expression in a plant, thereby modulating the stress tolerance of the plant. The present invention also includes identification of the homologs of PpAKT-2 as defined in SEQ ID NO:5, PpZT-1 as defined in SEQ ID NO:8, BnAKT-2 as defined in SEQ ID NO:10, GmZT-1 as defined in SEQ ID NO:12, GmZT-2 as defined in SEQ ID NO:14, and OsZT-1 as defined in SEQ ID NO:16 in a target plant, as well as the homolog's promoter. The invention also provides a method of increasing expression of a gene of interest within a host cell as compared to a wild type variety of the host cell, wherein the gene of interest is transcribed in response to an ITSRP, comprising: (a) transforming the host cell with an expression vector comprising an ITSRP coding nucleic acid, and (b) expressing the ITSRP within the host cell, thereby increasing the expression of the gene transcribed in response to the ITSRP, as compared to a wild type variety of the host cell.

In addition to introducing the ITSRP nucleic acid sequences into transgenic plants, these sequences can also be used to identify an organism as being *Physcomitrella patens, Brassica napus, Glycine max, Oryza sativa*, or a close relative thereof. Also, they may be used to identify the presence of *Physcomitrella patens, Brassica napus, Glycine max, Oryza sativa*, or a relative thereof in a mixed population of microorganisms. The invention provides the nucleic acid sequences of a number of *Physcomitrella patens, Brassica napus, Glycine max*, and *Oryza sativa* genes; by probing the extracted genomic DNA of a culture of a unique or mixed population of microorganisms under stringent conditions with a probe spanning a region of a *Physcomitrella patens, Brassica napus, Glycine max*, or *Oryza sativa* gene that is unique to this organism, one can ascertain whether this organism is present.

Further, the nucleic acid and polypeptide molecules of the invention may serve as markers for specific regions of the genome. This has utility not only in the mapping of the genome, but also in functional studies of *Physcomitrella patens, Brassica napus, Glycine max*, or *Oryza sativa* polypeptides. For example, to identify the region of the genome to which a particular *Physcomitrella patens* DNA-binding polypeptide binds, the *Physcomitrella patens* genome could be digested, and the fragments incubated with the DNA-binding polypeptide. Those fragments that bind the polypeptide may be additionally probed with the nucleic acid molecules of the invention, preferably with readily detectable labels. Binding of such a nucleic acid molecule to the genome fragment enables the localization of the fragment to the genome map of *Physcomitrella patens*, and, when performed multiple times with different enzymes, facilitates a rapid determination of the nucleic acid sequence to which the polypeptide binds. Further, the nucleic acid molecules of the invention may be sufficiently identical to the sequences of related species such that these nucleic acid molecules may serve as markers for the construction of a genomic map in related mosses.

The ITSRP nucleic acid molecules of the invention are also useful for evolutionary and polypeptide structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the polypeptide that are essential for the functioning of the enzyme. This type of determination is of value for polypeptide engineering studies and may give an indication of what the polypeptide can tolerate in terms of mutagenesis without losing function.

Manipulation of the ITSRP nucleic acid molecules of the invention may result in the production of ITSRPs having functional differences from the wild-type ITSRPs. These polypeptides may be improved in efficiency or activity, may be present in greater numbers in the cell than is usual, or may be decreased in efficiency or activity.

There are a number of mechanisms by which the alteration of an ITSRP of the invention may directly affect stress response and/or stress tolerance. In the case of plants expressing ITSRPs, increased transport can lead to improved salt and/or solute partitioning within the plant tissue and organs. By either increasing the number or the activity of transporter molecules that export ionic molecules from the cell, it may be possible to affect the salt tolerance of the cell.

The effect of the genetic modification in plants, *C. glutamicum*, fungi, algae, or ciliates on stress tolerance can be assessed by growing the modified microorganism or plant under less than suitable conditions and then analyzing the growth characteristics and/or metabolism of the plant. Such analysis techniques are well known to one skilled in the art, and include dry weight, wet weight, polypeptide synthesis, carbohydrate synthesis, lipid synthesis, evapotranspiration rates, general plant and/or crop yield, flowering, reproduction, seed setting, root growth, respiration rates, photosynthesis rates, etc. (Applications of HPLC in Biochemistry in: Laboratory Techniques in Biochemistry and Molecular Biology, vol. 17; Rehm et al., 1993 Biotechnology, vol. 3, Chapter III: Product recovery and purification, page 469–714, VCH: Weinheim; Belter, P. A. et al., 1988, Bio-separations: downstream processing for biotechnology, John Wiley and Sons; Kennedy, J. F. and Cabral, J. M. S., 1992, Recovery processes for biological materials, John Wiley and Sons; Shaeiwitz, J. A. and Henry, J. D., 1988, Biochemical separations, in: Ulmann's Encyclopedia of Industrial Chemistry, vol. B3, Chapter 11, page 1–27, VCH: Weinheim; and Dechow, F. J., 1989, Separation and purification techniques in biotechnology, Noyes Publications).

For example, yeast expression vectors comprising the nucleic acids disclosed herein, or fragments thereof, can be constructed and transformed into *Saccharomyces cerevisiae* using standard protocols. The resulting transgenic cells can then be assayed for fail or alteration of their tolerance to drought, salt, and temperature stresses. Similarly, plant expression vectors comprising the nucleic acids disclosed herein, or fragments thereof, can be constructed and transformed into an appropriate plant cell such as *Arabidopsis*, soy, rape, maize, wheat, *Medicago truncatula*, etc., using standard protocols. The resulting transgenic cells and/or plants derived there from can then be assayed for fail or alteration of their tolerance to drought, salt, and temperature stresses.

The engineering of one or more ITSRP genes of the invention may also result in ITSRPs having altered activities which indirectly impact the stress response and/or stress tolerance of algae, plants, ciliates, or fungi, or other microorganisms like *C. glutamicum*. For example, the normal biochemical processes of metabolism result in the production of a variety of products (e.g., hydrogen peroxide and other reactive oxygen species) which may actively interfere with these same metabolic processes. For example, peroxynitrite is known to nitrate tyrosine side chains, thereby inactivating some enzymes having tyrosine in the active site (Groves, J. T., 1999, Curr. Opin. Chem. Biol. 3(2):226–235). While these products are typically excreted, cells can be genetically altered to transport more products than is typical for a wild-type cell. By optimizing the activity of one or more ITSRPs of the invention that are involved in the export of specific molecules, such as salt molecules, it may be possible to improve the stress tolerance of the cell.

Additionally, the sequences disclosed herein, or fragments thereof, can be used to generate knockout mutations in the genomes of various organisms, such as bacteria, mammalian cells, yeast cells, and plant cells (Girke, T., 1998, The Plant Journal 15:39–48). The resultant knockout cells can then be evaluated for their ability or capacity to tolerate various stress conditions, their response to various stress conditions, and the effect on the phenotype and/or genotype of the mutation. For other methods of gene inactivation, see U.S. Pat. No. 6,004,804 "Non-Chimeric Mutational Vectors" and Puttaraju et al., 1999, Spliceosome-mediated RNA trans-splicing as a tool for gene therapy, Nature Biotechnology 17:246–252.

The aforementioned mutagenesis strategies for ITSRPs resulting in increased stress resistance are not meant to be limiting; variations on these strategies will be readily apparent to one skilled in the art. Using such strategies, and incorporating the mechanisms disclosed herein, the nucleic acid and polypeptide molecules of the invention may be utilized to generate algae, ciliates, plants, fungi, or other microorganisms like *C. glutamicum* expressing mutated ITSRP nucleic acid and polypeptide molecules such that the stress tolerance is improved.

The present invention also provides antibodies that specifically bind to an ITSRP, or a portion thereof, as encoded by a nucleic acid described herein. Antibodies can be made by many well-known methods (See, e.g., Harlow and Lane, "Antibodies; A Laboratory Manual," Cold Spring Harbor Laboratory, Cold Spring Harbor, N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. (See, for example, Kelly et al., 1992, Bio/Technology 10:163–167; Bebbington et al., 1992, Bio/Technology 10:169–175).

The phrases "selectively binds" and "specifically binds" with the polypeptide refer to a binding reaction that is determinative of the presence of the polypeptide in a heterogeneous population of polypeptides and other biologics. Thus, under designated immunoassay conditions, the specified antibodies bound to a particular polypeptide do not bind in a significant amount to other polypeptides present in the sample. Selective binding of an antibody under such conditions may require an antibody that is selected for its specificity for a particular polypeptide. A variety of immunoassay formats may be used to select antibodies that selectively bind with a particular polypeptide. For example, solid-phase ELISA immunoassays are routinely used to select antibodies selectively immunoreactive with a polypeptide. See Harlow and Lane, "Antibodies, A Laboratory Manual" Cold Spring Harbor Publications, New York, (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., eds., "Basic and Clinical Immunology," (Lange Medical Publications, Los Altos, Calif., Fourth Edition) and references cited therein, and in Harlow and Lane "Antibodies, A Laboratory Manual" Cold Spring Harbor Publications, New York, 1988.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Growth of *Physcomitrella patens* Cultures

For this study, plants of the species *Physcomitrella patens* (Hedw.) B. S. G. from the collection of the genetic studies section of the University of Hamburg were used. They originate from the strain 16/14 collected by H. L. K. Whitehouse in Gransden Wood, Huntingdonshire (England), which was subcultured from a spore by Engel (1968, Am. J. Bot. 55, 438–446). Proliferation of the plants was carried out by means of spores and by means of regeneration of the gametophytes. The protonema developed from the haploid spore as a chloroplast-rich chloronema and chloroplast-low caulonema, on which buds formed after approximately 12 days. These grew to give gametophores bearing antheridia and archegonia. After fertilization, the diploid sporophyte with a short seta and the spore capsule resulted, in which the meiospores matured.

Culturing was carried out in a climatic chamber at an air temperature of 25° C. and light intensity of 55 micromol s$^{-1}$ m$^{-2}$ (white light; Philips TL 65W/25 fluorescent tube) and a light/dark change of 16/8 hours. The moss was either modified in liquid culture using Knop medium according to Reski and Abel (1985, Planta 165:354–358) or cultured on Knop solid medium using 1% oxoid agar (Unipath, Basingstoke, England). The protonemas used for RNA and DNA isolation were cultured in aerated liquid cultures. The protonemas were comminuted every 9 days and transferred to fresh culture medium.

Example 2

Total DNA Isolation from Plants

The details for the isolation of total DNA relate to the working up of one gram fresh weight of plant material. The materials used include the following buffers: CTAB buffer: 2% (w/v) N-cethyl-N,N,N-trimethylammonium bromide (CTAB); 100 mM Tris HCl pH 8.0; 1.4 M NaCl; 20 mM EDTA; N-Laurylsarcosine buffer: 10% (w/v) N-laurylsarcosine; 100 mM Tris HCl pH 8.0; and 20 mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 μl of N-laurylsarcosine buffer, 20 μl of β-mercaptoethanol, and 10 μl of proteinase K solution, 10 mg/ml) and incubated at 60° C. for one hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000×g and room temperature for 15 minutes in each case. The DNA was then precipitated at −70° C. for 30 minutes using ice-cold isopropanol. The precipitated DNA was sedimented at 4° C. and 10,000 g for 30 minutes and resuspended in 180 μl of TE buffer (Sambrook et al., 1989, Cold Spring Harbor Laboratory Press: ISBN 0-87969-309-6). For further purification, the DNA was treated with NaCl (1.2 M final concentration) and precipitated again at −70° C. for 30 minutes using twice the volume of absolute ethanol. After a washing step with 70% ethanol, the DNA was dried and subsequently taken up in 50 μl of H$_2$O+RNAse (50 mg/ml final concentration). The DNA was dissolved overnight at 4° C., and the RNAse digestion was subsequently carried out at 37° C. for 1 hour. Storage of the DNA took place at 4° C.

Example 3

Isolation of Total RNA and Poly-(A)+ RNA and cDNA Library Construction from *Physcomitrella patens*

For the investigation of transcripts, both total RNA and poly-(A)$^+$ RNA were isolated. The total RNA was obtained from wild-type 9 day old protonemata following the GTC-method (Reski et al., 1994, Mol. Gen. Genet., 244:352–359). The Poly(A)+ RNA was isolated using Dyna Beads$^R$ (Dynal, Oslo, Norway) following the instructions of the manufacturer's protocol. After determination of the concentration of the RNA or of the poly(A)+ RNA, the RNA was precipitated by addition of 1/10 volumes of 3 M sodium acetate pH 4.6 and 2 volumes of ethanol and stored at −70° C.

For cDNA library construction, first strand synthesis was achieved using Murine Leukemia Virus reverse transcriptase (Roche, Mannheim, Germany) and oligo-d(T)-primers, second strand synthesis by incubation with DNA polymerase I, Klenow enzyme and RNAseH digestion at 12° C. (2 hours), 16° C. (1 hour), and 22° C. (1 hour). The reaction was stopped by incubation at 65° C. (10 minutes) and subsequently transferred to ice. Double stranded DNA molecules were blunted by T4-DNA-polymerase (Roche, Mannheim) at 37° C. (30 minutes). Nucleotides were removed by phenol/chloroform extraction and Sephadex G50 spin columns. EcoRI adapters (Pharmacia, Freiburg, Germany) were ligated to the cDNA ends by T4-DNA-ligase (Roche, 12° C., overnight) and phosphorylated by incubation with polynucleotide kinase (Roche, 37° C., 30 minutes). This mixture was subjected to separation on a low melting agarose gel. DNA molecules larger than 300 base pairs were eluted from the gel, phenol extracted, concentrated on Elutip-D-columns (Schleicher and Schuell, Dassel, Germany), and were ligated to vector arms and packed into lambda ZAPII phages or lambda ZAP-Express phages using the Gigapack Gold Kit (Stratagene, Amsterdam, Netherlands) using material and following the instructions of the manufacturer.

Example 4

Sequencing and Function Annotation of *Physcomitrella patens* ESTs cDNA libraries as described in Example 3 were used for DNA sequencing according to standard methods, and in particular, by the chain termination method using the ABI PRISM Big Dye Terminator Cycle Sequencing Ready Reaction Kit (Perkin-Elmer, Weiterstadt, Germany). Random sequencing was carried out subsequent to preparative plasmid recovery from cDNA libraries via in vivo mass excision, retransformation, and subsequent plating of DH10B on agar plates (material and protocol details from Stratagene, Amsterdam, Netherlands). Plasmid DNA was prepared from overnight grown *E. coli* cultures grown in Luria-Broth medium containing ampicillin (See Sambrook et al., 1989, Cold Spring Harbor Laboratory Press: ISBN 0-87969-309-6) on a Qiagene DNA preparation robot (Qiagen, Hilden) according to the manufacturer's protocols. Sequencing primers with the following nucleotide sequences were used:

| | |
|---|---|
| 5'-CAGGAAACAGCTATGACC-3' | SEQ ID NO:18 |
| 5'-CTAAAGGGAACAAAAGCTG-3' | SEQ ID NO:19 |
| 5'-TGTAAAACGACGGCCAGT-3' | SEQ ID NO:20 |

Sequences were processed and annotated using the software package EST-MAX commercially provided by Bio-Max (Munich, Germany). The program incorporates practically all bioinformatics methods important for functional and structural characterization of protein sequences. For reference, see the website at pedant.mips.biochem.mpg.de. The most important algorithms incorporated in EST-MAX are: FASTA (Very sensitive sequence database searches with estimates of statistical significance; Pearson W. R., 1990, Rapid and sensitive sequence comparison with FASTP and FASTA. Methods Enzymol. 183:63–98); BLAST (Very sensitive sequence database searches with estimates of statistical significance. Altschul S. F. et al., Basic local alignment search tool, Journal of Molecular Biology 215:403–10); PREDATOR (High-accuracy secondary structure prediction from single and multiple sequences. Frishman, D. and Argos, P., 1997, 75% accuracy in protein secondary structure prediction. Proteins, 27:329–335); CLUSTALW: Multiple sequence alignment. Thompson, J. D. et al., 1994, CLUSTAL W (improving the sensitivity of progressive multiple sequence alignment through sequence weighting, positions-specific gap penalties and weight matrix choice, Nucleic Acids Research, 22:4673–4680); TMAP (Transmembrane region prediction from multiply aligned sequences. Persson, B. and Argos, P., 1994, Prediction of transmembrane segments in proteins utilizing multiple sequence alignments. J. Mol. Biol. 237:182–192); ALOM2 (Transmembrane region prediction from single sequences. Klein, P. et al., Prediction of protein function from sequence properties: A discriminate analysis of a database. Biochim. Biophys. Acta 787:221–226 (1984). Version 2 by Dr. K. Nakai); PROSEARCH (Detection of PROSITE protein sequence patterns. Kolakowski L. F. Jr., Leunissen J. A. M., Smith J. E., 1992, ProSearch: fast searching of protein sequences with regular expression patterns related to protein structure and function. Biotechniques 13, 919–921); BLIMPS (Similarity searches against a database of ungapped blocks, J. C. Wallace and Henikoff S., 1992); PATMAT (a searching and extraction program for sequence, pattern and block queries and databases, CABIOS 8:249–254. Written by Bill Alford).

Example 5

Identification of *Physcomitrella patens* ORFs Corresponding to PpAKT-1, PpAKT-2, and PpZT-1

The *Physcomitrella patens* partial cDNAs (ESTs) for partial PpAKT-1 (SEQ ID NO:1), partial PpAKT-2 (SEQ ID NO:4), and partial PpZT-1 (SEQ ID NO:7) were identified in the *Physcomitrella patens* EST sequencing program using the program EST-MAX through BLAST analysis. These particular clones, which were found to encode for ion transporters, were chosen for further analyses (See Tables 1–4 below). The PpAKT-1 and PpAKT-2 cDNAs are 46% identical, while the PpAKT-1 and PpAKT-2 proteins are 12% identical and 25% similar.

TABLE 1

Identification of Open Reading Frames

| Name | Total Nucleotides in cDNA | ORF position | Total Amino Acids in ORF | Domain Position |
|---|---|---|---|---|
| PpAKT-1 | — | 258-695 | — | — |
| PpAKT-2 | 2553 | 55-2523 | 823 | 91-751 |
| PpZT-1 | 1462 | 21-1094 | 358 | 207-348 |

TABLE 2

Degree of amino acid identity and similarity of PpAKT-1 and other homologous proteins (GCG Gap program was used: gap penalty: 10; gap extension penalty: 0.1; score matrix: blosum62)

| Swiss-Prot # | O04242 | O24382 | Q38998 | Q9LEG6 | Q9LKP3 |
|---|---|---|---|---|---|
| Protein name | Potassium channel | Potassium channel | AKT1 potassium transporter | Potassium channel | Putative Potassium channel protein MKT1P |
| specie | Zea mays (Maize) | Solanum tuberosum (Potato) | Arabidopsis thaliana (Mouse-ear cress) | Lycopersicon esculentum (Tomato) | Mesembryanthemum crystallinum (Common ice plant) |
| Identity % | 41% | 40% | 41% | 41% | 40% |
| Similarity % | 55% | 56% | 55% | 56% | 56% |

TABLE 3

Degree of amino acid identity and similarity of PpAKT-2 and other homologous proteins (Pairwise comparison program was used: gap penalty: 10; gap extension penalty: 0.1; score matrix: blosum62)

| Swiss-Prot # | O64769 | O22398 | Q9LEQ2 | Q9SGA3 | O22881 |
|---|---|---|---|---|---|
| Protein name | Putative Potassium Transporter | Putative Potassium Transporter AKT-2 | Putative Cation Transport Protein | Putative Potassium Transporter | Putative Potassium Transporter |

TABLE 3-continued

Degree of amino acid identity and similarity of PpAKT-2 and other homologous proteins (Pairwise comparison program was used: gap penalty: 10; gap extension penalty: 0.1; score matrix: blosum62)

| Swiss-Prot # | O64769 | O22398 | Q9LEQ2 | Q9SGA3 | O22881 |
|---|---|---|---|---|---|
| Species | Arabidopsis thaliana (Mouse-ear cress | Arabidopsis thaliana (Mouse-ear cress | Arabidopsis thaliana (Mouse-ear cress | Arabidopsis thaliana (Mouse-ear cress) | Arabidopsis thaliana (Mouse-ear cress |
| Identity % | 45% | 41% | 41% | 41% | 41% |
| Similarity % | 62% | 57% | 56% | 56% | 57% |

TABLE 4

Degree of amino acid identity and similarity of PpZT-1 and other homologous proteins (Pairwise comparison program was used: gap penalty: 10; gap extension penalty: 0.1; score matrix: blosum62)

| Swiss-Prot # | O81124 | Q9LTH9 | Q38856 | Q9SLG3 | O81125 |
|---|---|---|---|---|---|
| Protein name | Putative Zinc Transporter | Zinc Transporter | Fe(II) Transport Protein | Putative Fe(II) Transporter | Putative Zinc Transporter |
| Species | Arabidopsis thaliana (Mouse-ear cress) | Arabidopsis thaliana (Mouse-ear cress) | Arabidopsis thaliana (Mouse-ear cress) | Arabidopsis thaliana (Mouse-ear cress) | Arabidopsis thaliana (Mouse-ear cress) |
| Identity % | 46% | 46% | 19% | 22% | 22% |
| Similarity % | 60% | 60% | 37% | 40% | 40% |

Example 6

Cloning of the Full-Length *Physcomitrella patens* cDNA Encoding for PpAKT-1, PpAKT-2, and PpZT-1

As described below, a full-length sequence corresponding to the partial cDNA PpAKT-1 (SEQ ID NO:1) was obtained by performing polymerase chain reaction (PCR) with gene-specific EST as the template DNA.

The synthetic oligonucleotide primers (MWG-Biotech) for the reaction were: 14F: 5'-ATCCCGGGCGTTTCG-TAGTGAGCAGTCTCCCA-3' (SEQ ID NO:21) and 14R: 5'-GCGAGCTCAGACACTGTCGCTGATCTCGTGAT-3' (SEQ ID NO:22). The primers designed contained a XmaI site in the 5' region and a SacI site in the 3' region for cloning purposes. The conditions for the reaction were standard conditions with PWO DNA polymerase (Roche). PCR was performed according to standard conditions and to manufacture's protocols (Sambrook et al., 1989, Biometra T3 Thermocycler). The parameters for the reaction were: five minutes at 94° C. followed by five cycles of one minute at 94° C., one minute at 50° C., and 4 minutes at 72° C. This was followed by twenty-five cycles of one minute at 94° C., one minute at 65° C., and 4 minutes at 72° C. These parameters generated a fragment 4.0 kilobases long. The fragment was extracted from agarose gel with a QIAquick Gel Extraction Kit (Qiagen) and ligated into the TOPO pCR 2.1 vector (Invitrogen) following manufacturer's instructions. Recombinant vectors were transformed into Top10 cells (Invitrogen) using standard conditions (Sambrook et al., 1989). Transformed cells were selected for on LB agar containing 100 µg/ml carbenicillin, 0.8 mg X-gal (5-bromo-4-chloro-3-indolyl-β-D-galactoside), and 0.8 mg IPTG (iso-propylthio-β-D-galactoside) grown overnight at 37° C. White colonies were selected and used to inoculate 3 ml of liquid LB containing 100 µg/ml ampicillin and grown overnight at 37° C. Plasmid DNA was extracted using the QIAprep Spin Miniprep Kit (Qiagen) following manufacturer's instructions. Analyses of subsequent clones and restriction mapping was performed according to standard molecular biology techniques (Sambrook et al., 1989).

To isolate full-length PpAKT-2 (SEQ ID NO:5) and PpZT-1 (SEQ ID NO:8) from *Physcomitrella patens*, PCR was performed (as described below in Full-Length Amplification) using the original ESTs described in Example 5 as template since they were full-length. The primers used for amplification are listed below in Table 5.

Full-Length Amplification

Full-length clones corresponding PpAKT-2 (SEQ ID NO:5) and PpZT-1 (SEQ ID NO:8) were obtained by performing polymerase chain reaction (PCR) with gene-specific primers (See Table 5) and the original EST as the template. The conditions for the reaction were standard conditions with PWO DNA polymerase (Roche). PCR was performed according to standard conditions and according to manufacturer's protocols (Sambrook et al., 1989, Molecular Cloning, A Laboratory Manual. 2nd Edition. Cold Spring Harbor Laboratory Press. Cold Spring Harbor, N.Y., Biometra T3 Thermocycler). The parameters for the reaction were: five minutes at 94° C. followed by five cycles of one minute at 94° C., one minute at 50° C., and 1.5 minutes at 72° C. This was followed by twenty five cycles of one minute at 94° C., one minute at 65° C., and 1.5 minutes at 72° C.

The amplified fragments were extracted from agarose gel with a QIAquick Gel Extraction Kit (Qiagen) and ligated into the TOPO pCR 2.1 vector (Invitrogen) following manufacturer's instructions. Recombinant vectors were transformed into Top10 cells (Invitrogen) using standard conditions (Sambrook et al., 1989, Molecular Cloning, A Laboratory Manual. 2nd Edition. Cold Spring Harbor Laboratory Press. Cold Spring Harbor, N.Y.). Transformed cells were selected for on LB agar containing 100 μg/ml carbenicillin, 0.8 mg X-gal (5-bromo-4-chloro-3-indolyl-β-D-galactoside), and 0.8 mg IPTG (isopropylthio-β-D-galactoside) grown overnight at 37° C. White colonies were selected and used to inoculate 3 ml of liquid LB containing 100 μg/ml ampicillin and grown overnight at 37° C. Plasmid DNA was extracted using the QIAprep Spin Miniprep Kit (Qiagen) following manufacturer's instructions. Analyses of subsequent clones and restriction mapping was performed according to standard molecular biology techniques (Sambrook et al., 1989, Molecular Cloning, A Laboratory Manual, 2nd Edition, Cold Spring Harbor Laboratory Press, Cold Spring Harbor, N.Y.).

conditions to strip the bound probes and returned to the hybridization chambers for another round of hybridization. The hybridization and imaging cycle was repeated until the set of 288 oligomers was completed.

After completion of the hybridizations, a profile was generated for each spot (representing a cDNA insert), as to which of the 288 $^{33}$P radiolabeled 7-mer oligonucleotides bound to that particular spot (cDNA insert), and to what degree. This profile is defined as the signature generated from that clone. Each clone's signature was compared with all other signatures generated from the same organism to identify clusters of related signatures. This process "sorts" all of the clones from an organism into clusters before sequencing.

TABLE 5

| Gene Name | Cloning Site | Cloning Method | Primers Race | Primer RT-PCR |
|---|---|---|---|---|
| PpAKT-2 | XmaI/SacI | 5' RACE and RT-PCR for Full-length clone | RC126<br>5'CCAAGCCAACATCGCTGGTCCGAAC3'<br>(SEQ ID NO:23) | RC325:<br>5'ATCCCGGGCGTCGCAGTTTACGTGTGTTCACC3'<br>(SEQ ID NO:25) |
|  |  |  | RC086<br>5'GAGCCCGACTCCCGGAACTCGAGAG3'<br>SEQ ID NO:24 | RC326:<br>5'ATCCCGGGCGTCGCAGTTTACGTGTGTTCACC3'<br>SEQ ID NO:26 |
| PpZT-1 | XmaI/SacI | RT-PCR for Full-length clone |  | RC015:<br>5'CTGAGCTCAAGTCCCACTATAAGAAGTAGTCT3'<br>(SEQ ID NO:27) |
|  |  |  |  | RC016:<br>5'TGAGCTCAAGTCAAGCATCCCAGATCATGACA3'<br>(SEQ ID NO:28) |

Tissue Harvest, RNA Isolation, and cDNA Library Construction

Canola, soybean, and rice plants were grown under a variety of conditions and treatments, and different tissues were harvested at various developmental stages. Plant growth and harvesting were done in a strategic manner such that the probability of harvesting all expressable genes in at least one or more of the resulting libraries is maximized. The mRNA was isolated as described in Example 3 from each of the collected samples, and cDNA libraries were constructed. No amplification steps were used in the library production process in order to minimize redundancy of genes within the sample and to retain expression information. All libraries were 3' generated from mRNA purified on oligo dT columns. Colonies from the transformation of the cDNA library into E. coli were randomly picked and placed into microtiter plates.

Probe Hybridization

Plasmid DNA was isolated from the E. coli colonies and then spotted on membranes. A battery of 288 $^{33}$P radiolabeled 7-mer oligonucleotides were sequentially hybridized to these membranes. To increase throughput, duplicate membranes were processed. After each hybridization, a blot image was captured during a phosphorimage scan to generate a hybridization profile for each oligonucleotide. This raw data image was automatically transferred via LIMS to a computer. Absolute identity was maintained by barcoding for the image cassette, filter, and orientation within the cassette. The filters were then treated using relatively mild Gene Isolation The clones were sorted into various clusters based on their having identical or similar hybridization signatures. A cluster should be indicative of the expression of an individual gene or gene family. A by-product of this analysis is an expression profile for the abundance of each gene in a particular library. One-path sequencing from the 5' end was used to predict the function of the particular clones by similarity and motif searches in sequence databases.

The full-length DNA sequence of the Physcomitrella patens PpAKT-2 (SEQ ID NO:5) or PpZT-1 (SEQ ID NO:8) was blasted against proprietary contig databases of canola, rice, and soybean at E value of E-10. (Altschul, Stephen et al., Gapped BLAST and PSI_BLAST: a new generation of protein database search program, Nucleic Acids Res. 25: 3389–3402). All the contig hits were analyzed for the putative full length sequences, and the longest clones representing the putative full length contigs were fully sequenced. Four such contigs isolated from the proprietary contig databases are BnAKT-2, GmZT-1, GmZT-2, and OsZT-1. The homology of the BnAKT-2, GmZT-1, GmZT-2, and OsZT-1 amino acid sequences to the closest known prior art is indicated in Tables 6–8. The OsZT-1 sequence (SEQ ID NO:17) was 48% identical and 63% similar to the ZT-1 sequence from Physcomitrella patens (SEQ ID NO:9), but did not have significant identity or similarity to a protein sequence in the public database.

TABLE 6

Degree of Amino Acid Identity and Similarity of BnAKT-2 and a Similar Protein (Pairwise Comparison was used: gap penalty: 10; gap extension penalty: 0.1; score matrix: blosum62)

| Gene Name | Public Database Sequence | Protein Name | Species | Sequence Identity (%) | Sequence Similarity (%) |
| --- | --- | --- | --- | --- | --- |
| BnAKT-2 | AAC12845 | Putative potassium transporter | Arabidopsis thaliana | 75% | 77% |

TABLE 7

Degree of Amino Acid Identity and Similarity of GmZT-1 and a Similar Protein (Pairwise Comparison was used: gap penalty: 10; gap extension penalty: 0.1; score matrix: blosum62)

| Gene Name | Public Database Sequence | Protein Name | Species | Sequence Identity (%) | Sequence Similarity (%) |
| --- | --- | --- | --- | --- | --- |
| GmZT-1 | aag09635 | Zinc transporter | Medicago truncatula | 73% | 82% |

TABLE 8

Degree of Amino Acid Identity and Similarity of GmZT-2 and a Similar Protein (Pairwise Comparison was used: gap penalty: 10; gap extension penalty: 0.1; score matrix: blosum62)

| Gene Name | Public Database Sequence | Protein Name | Species | Sequence Identity (%) | Sequence Similarity (%) |
| --- | --- | --- | --- | --- | --- |
| GmZT-2 | aag09635 | Zinc transporter | Medicago truncatula | 54% | 60% |

TABLE 9

Listed are the amino acid positions of the PFAM domain in BnAKT-2, GmZT-1, GmZT-2, and OsZT-1.

| Name | Domain Position |
| --- | --- |
| BnAKT-2 | 59-637 |
| GmZT-1 | 189-342 |
| GmZT-2 | 203-356 |
| OsZT-1 | 201-354 |

Example 7

Engineering Stress-Tolerant *Arabidopsis* Plants by Overexpressing the Genes PpAKT-1, PpAKT-2, and PpZT-1

Subcloning of PpAKT-1, PpAKT-2 and PpZT-1 into the Binary Vector

The fragments containing the different *Physcomitrella patens* ion transporters were excised from the recombinant PCR2.1 TOPO vectors by double digestion with restriction enzymes (See Table 10) according to manufacturer's instructions. The subsequent fragments were excised from agarose gel with a QIAquick Gel Extraction Kit (Qiagen) according to manufacturer's instructions, ligated into binary vectors, cleaved with appropriate enzymes (See Table 10), and dephosphorylated prior to ligation. The resulting recombinant vectors contained the corresponding ion transporter in the sense orientation under the control of the constitutive superpromoter.

TABLE 10

Listed are the names of the constructs of the *Physcomitrella patens* ion transporters used for plant transformation.

| Gene | Enzymes used to generate gene fragment | Enzymes used to restrict binary vector | Recombinant binary vector construct |
| --- | --- | --- | --- |
| PpAKT-1 | XmaI/SacI | XmaI/SacI | pBPS-LVM001 |
| PpAKT-2 | XmaI/SacI | XmaI/SacI | pBPS-LVM072 |
| PpZT-1 | XmaI/HpaI | XmaI/SacI | pBPS-MI003 |

*Agrobacterium* Transformation

The recombinant vectors were transformed into *Agrobacterium tumefaciens* C58C1 and PMP90 according to standard conditions (Hoefgen and Willmitzer, 1990).

Plant Transformation

*Arabidopsis thaliana* ecotype C24 were grown and transformed according to standard conditions (Bechtold, 1993, Acad. Sci. Paris. 316:1194–1199; Bent et al., 1994, Science 265:1856–1860).

Screening of Transformed Plants

T1 seeds were sterilized according to standard protocols (Xiong et al., 1999, Plant Molecular Biology Reporter 17: 159–170). Seeds were selected on ½ Murashige and Skoog media (MS) (Sigma-Aldrich), 0.6% agar and supplemented with 1% sucrose, and 2 µg/ml benomyl (Sigma-Aldrich). Seeds on plates were vernalized for four days at 4° C. The seeds were germinated in a climatic chamber at an air temperature of 22° C. and light intensity of 40 micromol $s^{-1} m^{-2}$ (white light; Philips TL 65W/25 fluorescent tube) and 16 hours light and 8 hours dark day length cycle. Transformed seedlings were selected after 14 days and transferred to ½ MS media supplemented with 0.6% agar, 1% sucrose, and allowed to recover for five to seven days.

Drought Tolerance Screening

T1 seedlings were transferred to dry, sterile filter paper in a petri dish and allowed to desiccate for two hours at 80% RH (relative humidity) in a Sanyo Growth Cabinet MLR-350H, micromol $s^{-1} m^{-2}$ (white light; Philips TL 65W/25 fluorescent tube). The RH was then decreased to 60%, and the seedlings were desiccated further for eight hours. Seedlings were then removed and placed on ½ MS 0.6% agar plates supplemented with 2 µg/ml benomyl (Sigma-Aldrich) and scored after five days. The transgenic plants were then screened for their improved drought tolerance.

Under drought stress conditions, PpAKT-1 overexpressing *Arabidopsis thaliana* plants showed a 75% survival rate (6 survivors from 8 stressed plants). Under the same conditions, wild-type plants showed much a much lower survival rate (below 20%). This result clearly indicates that the transgenic lines overexpressing the PpAKT-1 gene acquired drought stress tolerance. Additionally, PpAKT-2 over-expressing *Arabidopsis thaliana* plants showed a 53% survival rate (8 survivors from 15 stressed plants) whereas the untransformed control only showed a 6% survival rate. It is noteworthy that the analyses of these transgenic lines were performed with T1 plants, and therefore, the results will be better when a homozygous, strong expresser is found.

Transgenic plants over-expressing PpZT-1 are also screened for their improved drought tolerance demonstrating that transgene expression confers drought tolerance.

TABLE 11

| | Drought Stress Test | | |
|---|---|---|---|
| Gene Name | Number of survivors | Total number of plants | Percentage of survivors |
| PpAKT-1 | 6 | 8 | 75% |
| PpAKT-2 | 8 | 15 | 53% |
| Control for PpAKT-2 | 1 | 18 | 6% |

Freezing Tolerance Screening

Seedlings are moved to petri dishes containing ½ MS 0.6% agar supplemented with 2% sucrose and 2 μg/ml benomyl. After four days, the seedlings are incubated at 4° C. for 1 hour and then covered with shaved ice. The seedlings are then placed in an Environmental Specialist ES2000 Environmental Chamber and incubated for 3.5 hours beginning at −1.0° C., and decreasing 1° C. each hour. The seedlings are then incubated at −5.0° C. for 24 hours and then allowed to thaw at 5° C. for 12 hours. The water is poured off, and the seedlings are scored after 5 days.

The transgenic plants are screened for their improved cold tolerance, demonstrating that transgene expression confers cold tolerance.

Salt Tolerance Screening

Seedlings were transferred to filter paper soaked in ½ MS and placed on ½ MS 0.6% agar supplemented with 2 μg/ml benomyl the night before the salt tolerance screening. For the salt tolerance screening, the filter paper with the seedlings was moved to stacks of sterile filter paper, soaked in 50 mM NaCl, in a petri dish. After two hours, the filter paper with the seedlings was moved to stacks of sterile filter paper, soaked with 200 mM NaCl, in a petri dish. After two hours, the filter paper with the seedlings was moved to stacks of sterile filter paper, soaked in 600 mM NaCl, in a petri dish. After 10 hours, the seedlings were moved to petri dishes containing ½ MS 0.6% agar supplemented with 2 μg/ml benomyl. The seedlings were scored after 5 days.

PpZT-1 overexpressing *Arabidopsis thaliana* plants showed a 40% survival rate (4 survivors from 10 stressed plants) to the salt stress screening whereas the untransformed control only showed a 13% survival rate. It is noteworthy that these analyses were performed with T1 plants, and therefore, the results will be better when a homozygous, strong expresser is found.

Transgenic plants over-expressing PpAKT-1 and PpAKT-2 are also screened for their improved salt tolerance demonstrating that transgene expression confers salt tolerance.

TABLE 12

| | Salt Stress Test | | |
|---|---|---|---|
| Gene Name | Number of survivors | Total number of plants | Percentage of survivors |
| PpZT-1 | 4 | 10 | 40% |
| Control | 3 | 23 | 13% |

Example 8

Detection of the PpAKT-1, PpAKT-2, and PpZT-1 Transgenes in the Transgenic *Arabidopsis* Lines One leaf from a wild type and a transgenic *Arabidopsis* plant was homogenized in 250 μl Hexadecyltrimethyl ammonium bromide (CTAB) buffer (2% CTAB, 1.4 M NaCl, 8 mM EDTA, and 20 mM Tris, pH 8.0) and 1 μl β-mercaptoethanol. The samples were incubated at 60–65° C. for 30 minutes, and 250 μl of Chloroform was then added to each sample. The samples were vortexed for 3 minutes and centrifuged for 5 minutes at 18,000×g. The supernatant was taken from each sample, and 150 μl isopropanol was added. The samples were incubated at room temperature for 15 minutes, and centrifuged for 10 minutes at 18,000×g. Each pellet was washed with 70% ethanol, dried, and resuspended in 20 μl TE. Then, 2.5 μl of the above suspension was used in a 50 μl PCR reaction using Taq DNA polymerase (Roche Molecular Biochemicals) according to the manufacturer's instructions. Binary vector plasmid with each gene cloned in was used as positive control, and the wild type C24 genomic DNA was used as negative control in the PCR reactions. Then, 10 μl of each PCR reaction was analyzed on 0.8% agarose/ethidium bromide gel.

The PCR program was as follows: 30 cycles of 1 minute at 94° C., 30 seconds at 62° C., and 1 minute at 72° C., followed by 5 minutes at 72° C. The gene-specific primers are listed below.

```
PpAKT-1
Primers:
5'ACTCCGCATGGGTGTCACCTTTCGA3'     (SEQ ID NO:29)
5'CTTCTCCACCCTCGCAAACACGTCA3'    (SEQ ID NO:30)

PpAKT-2:
Primers:
5'CAGGAAGCGAGGCGATGTTTGCAG3'     (SEQ ID NO:31)
5'GAGCATGATGAGCGTGAGGAGGCACGT3'  (SEQ ID NO:32)

PpZT-1:
Primers:
5'GGCGACCTCATCATCCAGCGGCTGA3'    (SEQ ID NO:33)
5'CCAGTCTGCCACAGCGCCTTCTGTAG3'   (SEQ ID NO:34)
```

The transgenes were successfully amplified from the T1 transgenic lines, but not from the wild type C24. This result indicates that the T1 transgenic plants contain at least one copy of the transgene. There was no indication of existence of either identical or very similar genes in the untransformed *Arabidopsis thaliana* control that could be amplified by this method.

Example 9

Detection of the PpAKT-1, PpAKT-2, and PpZT-1 Transgene mRNA in Transgenic *Arabidopsis* Lines Transgene expression was detected using RT-PCR. Total RNA was isolated from stress-treated plants using a procedure adapted from (Verwoerd et al., 1989, NAR 17:2362). Leaf samples (50–100 mg) were collected and ground to a fine powder in liquid nitrogen. Ground tissue was resuspended in 500 µl of a 80° C., 1:1 mixture, of phenol to extraction buffer (100 mM LiCl, 100 mM Tris pH8, 10 mM EDTA, 1% SDS), followed by brief vortexing to mix. After the addition of 250 µl of chloroform, each sample was vortexed briefly. Samples were then centrifuged for 5 minutes at 12,000×g. The upper aqueous phase was removed to a fresh eppendorf tube. RNA was precipitated by adding $1/10^{th}$ volume 3 M sodium acetate and 2 volumes 95% ethanol. Samples were mixed by inversion and placed on ice for 30 minutes. RNA was pelleted by centrifugation at 12,000×g for 10 minutes. The supernatant was removed and pellets briefly air-dried. RNA sample pellets were resuspended in 10 µl DEPC treated water.

To remove contaminating DNA from the samples, each was treated with RNase-free DNase (Roche) according to the manufacturer's recommendations. cDNA was synthesized from total RNA using the Superscript First Strand cDNA Synthesis System for RT-PCT (Gibco-BRL) following the manufacturer's recommendations. PCR amplification of a gene-specific fragment from the synthesized cDNA was performed using Taq DNA polymerase (Roche) and gene-specific primers (See Table 13 for primers) in the following reaction: 1×PCR buffer, 1.5 mM $MgCl_2$, 0.2 µM each primer, 0.2 µM dNTPs, 1 unit polymerase, 5 µl cDNA from synthesis reaction. Amplification was performed under the following conditions: Denaturation, 95° C., 1 minute; annealing, 62° C., 30 seconds; extension, 72° C., 1 minute, 35 cycles; extension, 72° C., 5 minutes; hold, 4° C., forever. PCR product were run on a 1% agarose gel, stained with ethidium bromide, and visualized under UV light using the Quantity-One gel documentation system (Bio-Rad). Expression of the transgenes was detected in the T1 transgenic line.

These results demonstrate that the transgenes are expressed in the transgenic lines and strongly suggested that their gene product improved plant stress tolerance in the transgenic lines. In agreement with the previous statement, no expression of identical or very similar endogenous genes could be detected by this method. These results are in agreement with the data from Example 8.

TABLE 13

Primers used for the amplification of respective transgene mRNA in PCR using RNA isolated from transgenic *Arabidopsis thaliana* plants as template

| Gene | 5' primer | 3' primer |
|---|---|---|
| PpAKT-1 | (SEQ ID NO:29)<br>5'ACTCCGCATGGGTGT<br>CACCTTTCGA3' | (SEQ ID NO:30)<br>5'CTTCTCCACCCTCGCA<br>AACACGTCA3' |
| PpAKT-2 | RC1185 (SEQ ID NO:31)<br>5'CAGGAAGCGAGGCG<br>ATGTTTGCAG3' | RC1186 (SEQ ID NO:32)<br>5'GAGCATGATGAGCGT<br>GAGGAGGCACGT3' |
| PpZT-1 | RC1179 (SEQ ID NO:33)<br>5'GGCGACCTCATCATC<br>CAGCGGCTGA3' | RC1180 (SEQ ID NO:34)<br>5'CCAGTCTGCCACAGC<br>GCCTTCTGTAG3' |

Example 10

Engineering Stress-Tolerant Soybean Plants by Over-Expressing the PpAKT-1, PpAKT-2, and PpZT-1 Gene The constructs pBPS-LVM001, pBPS-LVM072, and pBPS-MI003 are used to transform soybean as described below.

Seeds of soybean are surface sterilized with 70% ethanol for 4 minutes at room temperature with continuous shaking, followed by 20% (v/v) Clorox supplemented with 0.05% (v/v) Tween for 20 minutes with continuous shaking. Then, the seeds are rinsed 4 times with distilled water and placed on moistened sterile filter paper in a Petri dish at room temperature for 6 to 39 hours. The seed coats are peeled off, and cotyledons are detached from the embryo axis. The embryo axis is examined to make sure that the meristematic region is not damaged. The excised embryo axes are collected in a half-open sterile Petri dish and air-dried to a moisture content less than 20% (fresh weight) in a sealed Petri dish until further use.

*Agrobacterium tumefaciens* culture is prepared from a single colony in LB solid medium plus appropriate selection agents followed by growth of the single colony in liquid LB medium to an optical density at 600 nm of 0.8. Then, the bacterial culture is pelleted at 7000 rpm for 7 minutes at room temperature, and resuspended in MS (Murashige and Skoog, 1962) medium supplemented with 100 µM acetosyringone. Bacterial cultures are incubated in this pre-induction medium for 2 hours at room temperature before use. The axes of soybean zygotic seed embryos at approximately 15% moisture content are imbibed for 2 hours at room temperature with the pre-induced *Agrobacterium* suspension culture. The embryos are removed from the imbibition culture and are transferred to Petri dishes containing solid MS medium supplemented with 2% sucrose and incubated for 2 days in the dark at room temperature. Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/L carbenicillin or 300 mg/L cefotaxime to kill the Agrobacteria. The liquid medium is used to moisten the sterile filter paper. The embryos are incubated for 4 weeks at 25° C., under 150 µmol $m^{-2}sec^{-1}$ and 12 hours photoperiod. Once the seedlings produce roots, they are transferred to sterile metromix soil. The medium of the in vitro plants is washed off before the plants are transferred to soil. The plants are kept under a plastic cover for 1 week to favor the acclimatization process. Then the plants are transferred to a growth room where they are incubated at 25° C., under 150 µmol $m^{-2}sec^{-1}$ light intensity and 12 hours photoperiod for about 80 days.

The transgenic plants are screened for their improved drought, salt, and/or cold tolerance according to the screening method described in Example 7, demonstrating that transgene expression confers stress tolerance.

Example 11

Engineering Stress-Tolerant Rapeseed/Canola Plants by Overexpressing the PpAKT-1, PpAKT-2, or PpZT-1 Gene The constructs pBPS-LVM001, pBPS-LVM072, and pBPS-MI003 are used to transform rapeseed as described below.

The method of plant transformation described herein is also applicable to *Brassica* and other crops. Seeds of canola are surface sterilized with 70% ethanol for 4 minutes at room temperature with continuous shaking, followed by 20% (v/v) Clorox supplemented with 0.05% (v/v) Tween for 20 minutes, at room temperature with continuous shaking. Then, the seeds are rinsed 4 times with distilled water and placed on moistened sterile filter paper in a Petri dish at room temperature for 18 hours. Then the seed coats are removed, and the seeds are air dried overnight in a half-open sterile Petri dish. During this period, the seeds lose approximately 85% of their water content. The seeds are then stored at room temperature in a sealed Petri dish until further use. DNA constructs and embryo imbibition are as described in Example 10. Samples of the primary transgenic plants (T0) are analyzed by PCR to confirm the presence of T-DNA. These results are confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

The transgenic plants are screened for their improved stress tolerance according to the screening method described in Example 7, demonstrating that transgene expression confers stress tolerance.

Example 12

Engineering Stress-Tolerant Corn Plants by Over-Expressing the PpAKT-1, PpAKT-2, or PpZT-1 Gene The constructs pBPS-LVM001, pBPS-LVM072, and pBPS-MI003 are used to transform corn as described below.

Transformation of maize (*Zea Mays* L.) is performed with the method described by Ishida et al., 1996, Nature Biotech. 14745–50. Immature embryos are co-cultivated with *Agrobacterium tumefaciens* that carry "super binary" vectors, and transgenic plants are recovered through organogenesis. This procedure provides a transformation efficiency of between 2.5% and 20%. The transgenic plants are screened for their improved drought, salt, and/or cold tolerance according to the screening method described in Example 7, demonstrating that transgene expression confers stress tolerance.

Example 13

Engineering Stress-Tolerant Wheat Plants by Over-Expressing the PpAKT-1, PpAKT-2, or PpZT-1 Gene The constructs pBPS-LVM001, pBPS-LVM072 and pBPS-MI003 are used to transform wheat as described below.

Transformation of wheat is performed with the method described by Ishida et al., 1996, Nature Biotech. 14745–50. Immature embryos are co-cultivated with *Agrobacterium tumefaciens* that carry "super binary" vectors, and transgenic plants are recovered through organogenesis. This procedure provides a transformation efficiency between 2.5% and 20%. The transgenic plants are screened for their improved stress tolerance according to the screening method described in Example 7, demonstrating that transgene expression confers stress tolerance.

Example 14

Identification of Homologous and Heterologous Genes

Gene sequences can be used to identify homologous or heterologous genes from cDNA or genomic libraries. Homologous genes (e.g. full-length cDNA clones) can be isolated via nucleic acid hybridization using for example cDNA libraries. Depending on the abundance of the gene of interest, 100,000 up to 1,000,000 recombinant bacteriophages are plated and transferred to nylon membranes. After denaturation with alkali, DNA is immobilized on the membrane by, e.g., UV cross linking. Hybridization is carried out at high stringency conditions. In aqueous solution, hybridization and washing is performed at an ionic strength of 1 M NaCl and a temperature of 68° C. Hybridization probes are generated by, e.g., radioactive ($^{32}$P) nick transcription labeling (High Prime, Roche, Mannheim, Germany). Signals are detected by autoradiography.

Partially homologous or heterologous-genes that are related but not identical can be identified in a manner analogous to the above-described procedure using low stringency hybridization and washing conditions. For aqueous hybridization, the ionic strength is normally kept at 1 M NaCl while the temperature is progressively lowered from 68 to 42° C.

Isolation of gene sequences with homologies (or sequence identity/similarity) only in a distinct domain of (for example 10–20 amino acids) can be carried out by using synthetic radio labeled oligonucleotide probes. Radiolabeled oligonucleotides are prepared by phosphorylation of the 5-prime end of two complementary oligonucleotides with T4 polynucleotide kinase. The complementary oligonucleotides are annealed and ligated to form concatemers. The double stranded concatemers are then radiolabeled by, for example, nick transcription. Hybridization is normally performed at low stringency conditions using high oligonucleotide concentrations.

Oligonucleotide Hybridization Solution:
6×SSC
0.01 M sodium phosphate
1 mM EDTA (pH 8)
0.5% SDS
100 μg/ml denatured salmon sperm DNA
0.1% nonfat dried milk During hybridization, the temperature is lowered stepwise to 5–10° C. below the estimated oligonucleotide $T_m$, or down to room temperature, followed by washing steps and autoradiography. Washing is performed with low stringency, such as 3 washing steps using 4×SSC. Further details are described by Sambrook, J. et al., 1989, "Molecular Cloning: A Laboratory Manual", Cold Spring Harbor Laboratory Press or Ausubel, F. M. et al., 1994, "Current Protocols in Molecular Biology", John Wiley & Sons.

Example 15

Identification of Homologous Genes by Screening Expression Libraries with Antibodies c-DNA clones can be used to produce recombinant protein for example in *E. coli* (e.g. Qiagen QIAexpress pQE system). Recombinant proteins are then normally affinity purified via Ni-NTA affinity chromatography (Qiagen). Recombinant proteins are then used to produce specific antibodies for example by using standard techniques for rabbit immunization. Antibodies are affinity purified using a Ni-NTA column saturated with the recombinant antigen as described by Gu et al., 1994, BioTechniques 17:257–262. The antibody can be used to screen expression cDNA libraries to identify homologous or heterologous genes via an immunological screening (Sambrook, J. et al., 1989, "Molecular Cloning: A Laboratory Manual", Cold Spring Harbor Laboratory Press or Ausubel, F. M. et al., 1994, "Current Protocols in Molecular Biology", John Wiley & Sons).

Example 16

In vivo Mutagenesis

In vivo mutagenesis of microorganisms can be performed by passage of plasmid (or other vector) DNA through *E. coli* or other microorganisms (e.g. Bacillus spp. or yeasts such as *Saccharomyces cerevisiae*) which are impaired in their capabilities to maintain the integrity of their genetic information. Typical mutator strains have mutations in the genes for the DNA repair system (e.g., mutHLS, mutD, mutT, etc.; for reference, see Rupp, W. D., 1996, DNA repair mechanisms, in: *Escherichia coli* and *Salmonella*, p. 2277–2294, ASM: Washington.) Such strains are well known to those skilled in the art. The use of such strains is illustrated, for example, in Greener, A. and Callahan, M., 1994, Strategies 7:32–34. Transfer of mutated DNA molecules into plants is preferably done after selection and testing in microorganisms. Transgenic plants are generated according to various examples within the exemplification of this document.

Example 17

In vitro Analysis of the Function of *Physcomitrella* Genes in Transgenic Organisms The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications, and examples for the determination of many enzyme activities may be found, for example, in the following references: Dixon, M., and Webb, E. C., 1979, Enzymes. Longmans: London; Fersht, 1985, Enzyme Structure and Mechanism. Freeman: New York; Walsh, 1979, Enzymatic Reaction Mechanisms. Freeman: San Francisco; Price, N. C., Stevens, L., 1982, Fundamentals of Enzymology. Oxford Univ. Press: Oxford; Boyer, P. D., ed., 1983, The Enzymes, $3^{rd}$ ed. Academic Press: New York; Bisswanger, H., 1994, Enzymkinetik, $2^{nd}$ ed. VCH: Weinheim (ISBN 3527300325); Bergmeyer, H. U., Bergmeyer, J., Graβl, M., eds., 1983–1986, Methods of Enzymatic Analysis, $3^{rd}$ ed., vol. I–XII, Verlag Chemie: Weinheim; and Ullmann's Encyclopedia of Industrial Chemistry, 1987, vol. A9, Enzymes. VCH: Weinheim, p. 352–363.

The activity of proteins which bind to DNA can be measured by several well-established methods, such as DNA band-shift assays (also called gel retardation assays). The effect of such proteins on the expression of other molecules can be measured using reporter gene assays (such as that described in Kolmar, H. et al., 1995, EMBO J. 14: 3895–3904 and references cited therein). Reporter gene test systems are well known and established for applications in both pro- and eukaryotic cells, using enzymes such as β-galactosidase, green fluorescent protein, and several others.

The determination of activity of membrane-transport proteins can be performed according to techniques such as those described in Gennis, R. B., 1989, Pores, Channels and Transporters, in Biomembranes, Molecular Structure and Function, pp. 85–137, 199–234 and 270–322, Springer: Heidelberg.

Example 18

Purification of the Desired Product from Transformed Organisms

Recovery of the desired product from plant material (i.e., *Physcomitrella patens* or *Arabidopsis thaliana*), fungi, algae, ciliates, *C. glutamicum* cells, or other bacterial cells transformed with the nucleic acid sequences described herein, or the supernatant of the above-described cultures can be performed by various methods well known in the art. If the desired product is not secreted from the cells, the cells can be harvested from the culture by low-speed centrifugation, and the cells can be lysed by standard techniques, such as mechanical force or sonification. Organs of plants can be separated mechanically from other tissue or organs. Following homogenization, cellular debris is removed by centrifugation, and the supernatant fraction containing the soluble proteins is retained for further purification of the desired compound. If the product is secreted from desired cells, then the cells are removed from the culture by low-speed centrifugation, and the supernate fraction is retained for further purification.

The supernatant fraction from either purification method is subjected to chromatography with a suitable resin, in which the desired molecule is either retained on a chromatography resin while many of the impurities in the sample are not, or where the impurities are retained by the resin while the sample is not. Such chromatography steps may be repeated as necessary, using the same or different chromatography resins. One skilled in the art would be well-versed in the selection of appropriate chromatography resins and in their most efficacious application for a particular molecule to be purified. The purified product may be concentrated by filtration or ultrafiltration, and stored at a temperature at which the stability of the product is maximized.

There is a wide array of purification methods known to the art and the preceding method of purification is not meant to be limiting. Such purification techniques are described, for example, in Bailey, J. E. & Ollis, 1986, D. F. Biochemical Engineering Fundamentals, McGraw-Hill: New York. Additionally, the identity and purity of the isolated compounds may be assessed by techniques standard in the art. These include high-performance liquid chromatography (HPLC), spectroscopic methods, staining methods, thin layer chromatography, NIRS, enzymatic assay, or microbiologically. Such analysis methods are reviewed in: Patek et al., 1994, Appl. Environ. Microbiol. 60:133–140; Malakhova et al., 1996, Biotekhnologiya 11:27–32; and Schmidt et al., 1998, Bioprocess Engineer. 19:67–70; Ulmann's Encyclopedia of Industrial Chemistry, 1996, vol. A27, VCH: Weinheim, p. 89–90, p. 521–540, p. 540–547, p. 559–566, 575–581, and p. 581–587; Michal, G., 1999, Biochemical Pathways: An Atlas of Biochemistry and Molecular Biology, John Wiley and Sons; Fallon, A. et al., 1987, Applications of HPLC in Biochemistry in: Laboratory Techniques in Biochemistry and Molecular Biology, vol. 17.

APPENDIX

Nucleotide sequence of the partial AKT-1 from *Physcomitrella patens* (SEQ ID NO:1)
GCACGAGCAGATGAAGGCTGAGTCACTTCGGAAGTGCAGTGATCGTCTCTGTTT
CTGAGGAATATTTATCGTACAGTGCTCGTTTTGTTGAACTCGTCTTTATGTCTTGG
TCGCGAAGCCTTCCGTGACGCGGATTTGATAGCAGTTTTGCAGCTCACTGGGTAG
GAGCGTTCTTCACGCTCATGGTTTCAGTTTGGATGTTGTCGCTGGCTTTAGATTGC
CTTTGGACGATGACTCAATTCGGTGAAAATTCGATAAGTTGCGTTTCGTAGTGAG
CAGTCTCCCAGAGGAATCTGCCATTGTGTAGCGAGGTGTAGGATCATGGGGTGG
TCGGTAAGCGGGTTGACCCACAAGGTCCTTGGAGCAGTGGGGCTGATGAAGTAC
GGCAATCAGCGCAAGGCCTCTACCCCCAGCATCTTCAGCCATGCATACAGCAGC
GGAATGTTGCCGGCTCTTGGATCCAACCAGAGTACGAAGAACGTCCTTCAAAAG
AAATACGTTATTCATCCTTACAACAAGAATTACAGGTACTGGCAGGGGATTTTG
GTGGTGCTAGTGTTTTACTCCGCATGGGTGTCACCTTTCGAGTTTGGGTTCGTGC
AAAATCCTCGCGGTGCTCTGTTAACTGTCGACAATATTGTCAACTTTCTCTTCTTC
ATCGACATCGTATTGACCTTCTTCGTCGCGTATCTCGACA Nucleotide sequence of the full-length AKT-1 from *Physcomitrella patens* (SEQ ID NO:2)
GAATTCGCCCTTATCCCGGGCGTTTCGTAGTGAGCAGTCTCCCAGAGGAATCTGC
CATTGTGTAGCGAGGTGTAGGATCATGGGGTGGTCGGTAAGCGGGTTGACCCAC
AAGGTCCTTGGAGCAGTGGGGCTGATGAAGTACGGCAATCAGCGCAAGGCCTCT
ACCCCCAGCATCTTCAGCCATGCATACAGCAGCGGAATGTTGCCGGCTCTTGGAT
CCAACCAGAGTACGAAGAACGTCCTTCAAAAGAAATACGTTATTCATCCTTACA
ACAAGAATTACAGGTACTGGCAGGGGATTTTGGTGGTGCTAGTGTTTTACTCCGC
ATGGGTGTCACCTTTCGAGTTTGGGTTCGTGCAAAATCCTCGCGGTGCTCTGTTA
ACTGTCGACAATATTGTCAACTTTCTCTTCTTCATCGACATCGTATTGACCTTCTT
CGTCGCGTATCTCGACACCTCAACTTTTTTGATGGAAGACAACTTGAAGAAGATC
GCCATCAGGTATTTGAGAACATGGTTTATTTTGGATGTTGTGTCGACTGTTCCAT
TGGCCGCAGTAATAGCGATTTTCACTGGAAAATATGAGACAGGGTTTGCGGCCA
GTTTTGTCAATTTGTTGCGCCTCTGGCGATTGCGCCGTGTGAGTGACGTGTTTGC
GAGGGTGGAGAAGAATGTGAAATTTAGTTACTTCTGGACTCGATGCCTCAAACT
CTTTCTGGTGACTGTGTTTGTTTGCCACTTTGCGGCCTGCTCGTACTACTTATTGG
CTGCTCGACATCCGGCAAGCAAAGAGGCAGATACGTGGCTAGGAGCTGTGCTCC
CAAATTTTAAAGAGGAGTCACTGTGGGCGCGGTACGTGACGAGTATGTACTGGT CCATCACTACACTGGCGACTGTGGGATATGGCGATTTGCATCCAGTCAACCGTG
GTGAAATGATCTTCACCATCCTTTACATGTTGCTGAATCTGGCATTGACTGCGTA
CATCATAGGAAACATGACCAATCTCATCACTCGTCTTACCGCACGAACTCGTGAC
TATCGTGACTCGGTGCAACAATTGGTGGAGTTTGCAACTAGAAATCAGTTGCCA
CGCAAGCTTCACGAGCAAATGATCTCCCACGTGCAGCTCAAGTTCAAGACAGAG
AGCCTTCAGCATCAAGGGACCATAGCCACCCTACCAAAGGCTATCCGCTCATCT
GTTGCGCAATTTCTGTTTTTAACACAGTCGAGAAAGTGTACCTTTTCCAAGGCA
CTTCTTACAATTTTCGTACTCAGCTGGTGTCGGAGATGAAGGTCGAGTTCTTCCC
TCCTCGCGAGGAAATTATTCTGGTTAACGAGGCCCCCTCCGAGTTTTACATAGTT
GTGAATGGTTCCGCGGATGTAATAATTCGAAGGGAGGAAGCCGGATCAGAGCAA
ATTCTAATGACGGCTCAGGCAACTGATGTAATTGGCGAGATAGGGGTGATTTGTT
ACAGGCCACAGCCTTTCACTGTGCGAAGTCGAAAGTTATCCCAGCTCTTGCGACT
TGACCGCATTGTGTTTATGAACATTGTGCAACAATACAAGGAAGACGGCCAGAA
GATTGTTGACAATCTGTTGCAGCGCTTGCGAGAAGCCTATGATCCTCGATTTGAG
GAGCTTTCCTCTGAGATTGAAGCCCTCCTTGTTGAAGGCGGCGAAATATCGGAA
CCAAGCGTATGTGCGGTTGCTGCCGGAGGAAATGTGGAGGTTATGCAGCAGCTG
TTGAGCAAAGGCGCGGAGGTGGACAAGACAGATTATCACGGTCGGACTGCTCTG
GTCATTGCATCATCAAAAGGTTACGAGGAGTGCGTCAAGCTCCTTCTGGAACAC
GGAGCTGACCCCAACAAGGCTGATGTGTATGGGAAGGTTCCTCTACTTGAGGCC
CTTATTGCCCGCGACACGGCTACCGTGAAGCTCTTATCAGAGAACGGGGCGACC
TTGAAAAATGCGGACATGGGGGTATACCTCGGGCAAGCTGTGCTCGACTGTAAT
CGAGACCTCATTGACGACTACTTAAAATATGGAACCGACATAAACACAGCAGGC
GAATCTGAAGGACTGAGTGCGCTCCACATTGCTGTTATTGATGGCAACATGGAT
ATGGTGAGGTTTTTAGTATCCCGAGGAGCCGACCCTCACATCAAGCCTGGTGAT
GAGGCCACCCTTACCGCATACGAGCTAGCTGAGAGAAGTGCAGATCACCCCGAA
ATAGCTTCCTTTTGAAGGCCCAATCAGTCCGCGATGAACCATACAGTTCCATCA
CGCCTAGAGAGTCGACATCTAACGCAAATCAGAAGAGGCTTCCAAGGAAGGGA
AGCTCCAATGTTGAATTCCAGATTGATGAGGTAACACCCCCGCCTAGTCCAAAT
AAAGGATTTTCCGGAGAGCGAACGATACACTCATTAATGCGAAAGCAGTCGGCT
CGGGGCCGTCTCATGACTATAAGAGGACAGAAAACCCTCAGCCGGCAACTAAAC
GCAAACCAGAACCCTTCAGGTTGGGGCTTGAGACGGCGTGACAATCGAGACCCT
CTTCAGACTTTTCCATCAGCTGGCGCTGCTAAGGAGGTTCCTCTTCGTGTCATCA
TCCATTCTTATCATCCTTGGAACAAGGAAGCGGTGGGACTTGGAAAGGTCGTTTT
GCTGCCGAAAACTATTGAAGAGGTTCTCAAGATTGCGAACGAGAAATTCAACAA TCATCCAACGAAGGTGTTGAACAAAGAGGCAGCTGAGATTGACGACTTGAGTGT
CATCCGAGAAAACGACAACTTGTATGTCATTAACGATTCAGAGAAGTTGAACAC
GAGTTCCCCCCCAGGGATGGACACAGATGACCTCATAGCAAGATTGCAAGCAAT
AGTCACAGCATTGTCTCAACCCAAACCATAGACTCATGCATGCGACCAAGGTTG
GGTATGTACTTCTCATAAGCTTAGGACTCGACTTAGGATATCACGAGATCAGCG
ACAGTGTCTGAGCTCGCAAGGGCGAATTC Deduced amino acid sequence of AKT-1 from *Physcomitrella patens* (SEQ ID NO.3)
MGWSVSGLTHKVLGAVGLMKYGNQRKASTPSIFSHAYSSGMLPALGSNQSTKNVL
QKKYVIHPYNKNYRYWQGILVVLVFYSAWVSPFEFGFVQNPRGALLTVDNIVNFLFF
IDIVLTFFVAYLDTSTFLMEDNLKKIAIRYLRTWFILDVVSTVPLAAVIAIFTGKYETGF
AASFVNLLRLWRLRRVSDVFARVEKNVKFSYFWTRCLKLFLVTVFVCHFAACSYYL
LAARHPASKEADTWLGAVLPNFKEESLWARYVTSMYWSITTLATVGYGDLHPVNR
GEMIFTILYMLLNLALTAYIIGNMTNLITRLTARTRDYRDSVQQLVEFATRNQLPRKL
HEQMISHVQLKFKTESLQHQGTIATLPKAIRSSVAQFLFFNTVEKVYLFQGTSYNFRT
QLVSEMKVEFFPPREEIILVNEAPSEFYIVVNGSADVIIRREEAGSEQILMTAQATDVIG
EIGVICYRPQPFTVRSRKLSQLLRLDRIVFMNIVQQYKEDGQKIVDNLLQRLREAYDP
RFEELSSEIEALLVEGGEISEPSVCAVAAGGNVEVMQQLLSKGAEVDKTDYHGRTAL
VIASSKGYEECVKLLLEHGADPNKADVYGKVPLLEALIARDTATVKLLSENGATLKN
ADMGVYLGQAVLDCNRDLIDDYLKYGTDINTAGESEGLSALHIAVIDGNMDMVRFL
VSRGADPHIKPGDEATLTAYELAERSADHPEIASFLKAQSVRDEPYSSITPRESTSNAN
QKRLPRKGSSNVEFQIDEVTPPPSPNKGFSGERTIHSLMRKQSARGRLMTIRGQKTLS
RQLNANQNPSGWGLRRRDNRDPLQTFPSAGAAKEVPLRVIIHSYHPWNKEAVGLGK
VVLLPKTIEEVLKIANEKFNNHPTKVLNKEAAEIDDLSVIRENDNLYVINDSEKLNTSS
PPGMDTDDLIARLQAIVTALSQPKP*

Nucleotide sequence of the partial PpAKT-2 from *Physcomitrella patens* (SEQ ID NO:4)
GCTACTTCAAATGATGCGTGGGATGGATTGACTGTATGCTTCGGTCGATCGAGTC
CTCTCAACGAATCCAAGAATTGTTCGTCGTCAAAAGAACAATTATGCCGTTGGAA
CGGGATTGGAACTCTCAGACGTAATACTCCATGCCCACCTTCAGCAACCTGTCTT
TAGGGATGCTTAAGTACAGCGTGTTGTTGCGGCAGTTCCGTCGCAAAAACTTGTA
AATCTTATTGATGATGATGCGTTTAGGAAACCACGAGTCGCTCTTGGCGTGGATG
TCACTGTCGCCAAGCACGTACACGACGCCTGCTTCTCTGGCCTTCTGCAAGAACA
GAACTTCCTCGTTGGTGTAAGCTTCTTGATCGGCTTCCAGCTCATCCACAGTCTTT GCGCCGATGTCTGACCCACAGGAGTCGTTCGAAACCGACGACTCGCAGGGCCTA
TCTAATTTGTGATGGCTAGGAGAGGCGGCATGGGAGGAGGCCAGCCCTGATTCA
GGAGTGACTTCCGCCGCTTCCGTTCTGATGAACCTTTCCAGGCTCGCAAGGAGCA
TGTTTTCAAAGGTCTGGCCGTCTGATTCAGCCCCATCCACATGATCTGTGTAGCC
GTAGCGAACTGCACAACGGAACATGCGGTAGTTTCTGGGACCGAGCCTGCGGAT
AAGGATTCGCTCATCTTCGGGGACGGTGCTGACAGAGATGTGGCGGATGCAGAC
GAACACTAGAGTGGAGTGGATAGCAGGGAGATTCGAGATGAAGTGGCGAAATA
TTGCTGGAACTCCCTGCGGAAGCTCAGTGTATACGAGCCCGACTCCCGGAACTCG
AGAGATTCCTAGGCTATGGCCAAGAGACAGAACCCAGTCCAAGGAAATCTTATG
AGAGACCTCATACAAGCGTTTCATCCTGGTGCCGAAGTTCCACGAGTACATGATC
GTGAGGAAGCATGCGGCGATAACGAGGGGAACCCATCCGCCCTGCGTCACCTTG
GAGAGCACCCTGGTGC Nucleotide sequence of the full-length PpAKT-2 from *Physcomitrella patens* (SEQ ID NO:5)
ATCCCGGGCGTCGCGTTTACGTGTGTTCACCGTATATCTGGTCAATTCTTGATCAT
GGAGACGTCGGCGGTTGAATTGCAAATGTCTACAGACGCAGTCCATCAGAGAGA
AACTGGAGAGAGACCTCCATTAGAACAAACTGCGCAAGATGAAGAGACCAGTC
GGGAGGCCTTGCACGCGGATGAGGCTGCCTATCGAGAGAAGGAAGGTCCCTTTC
GACGGTTGTCGCGGAAGCTCACGCGGCCCGATTCCCTTGACGTGGAGTCCATGC
GAGTGAAAGAAATGGACCATGCTGCACCTGTAGCATCGTTTTCGTTCATTCTGAA
GCTGGCGTATCAGAGCATCGGGGTGGTGTATGGTGATCTGGGTACGTCCCCGCTC
TACGTGTACAGTAGCACTTTCACAAGCGGCATCAAAACGAACGACGACATTCTG
GGCGTTCTCTGTCTCATCATCTACACCATCATTGCCACTCCGCTCGTCAAGTACAT
CTTTATCGTCCTTCGGGCAAACGACAATGGCGAAGGGGGTACATTTGCGTTGTAT
TCATTGATTTGTCGACACGTTAAGCTGAGCGGGGCTCACGCGCAGCAGCCCACA
GACTTGAACATTTCAAGCTACAAGCTGGAGACACCGTCCACGAAGATGGCTAGG
GCGACGCGCATTAAGGAGGCGCTTGAGAAAAGCAGAGCTTGGCAGAATGTCCTG
CTTCTGATTGTTCTGTTAGGGCCTTGCTTGGTCATCGGCGATGGGTCCCTAACGCC
CGCCATCTCAGTTCTATCGGCCATTCAGGGTATCAGCGTGAACGTTAGTGGCCTT
TCTCCCAATGTGTCGGTGATTATCACGGTCGTTGTATTGGCAGCCCTCTTCAGCCT
TCAGCGATTTGGCACTCACAGGGTGGCTTTCTTGTTCGGACCAGCGATGTTGGCT
TGGTTCTTCTCCATCGGCATCATAGGGCTGTACAACATTTTCAGATGGGATCCTT
CGGTGTTCAAGGCTCTCAATCCTTGGTATGGACTTAATTACTTCATCAGAAACAA
AGTAGACGCTTGGGCTTCCCTCGGAGGTATCGTTCTCTGCATTACAGGAAGCGAG GCGATGTTTGCAGATTTGGGCCATTTTACTGTCAAGTCAATGCAGGTTGCCTTCA
CATTCTTGGTGTTCCCGTCTCTCCTATGTGCATACATCGGCCAGGCTTCATTTCTT
ATGAAGAATCAGCTTGATGACGATGTGGCCTACACATTCTACCGCTCCGTTCCAA
AGCCTATTTACTGGCCCATGTTCGGGGTCGCTACATGCGCGGCGATCATCGCCAG
TCAAGCTATGATTTCAGCGACATACTCGATGATCAGAAATGCCATGTCCCTGGGT
TGCTTCCCGCGTGTCACCATAGTTCACACCTCTAAGAAGGTGCACGGCCAGATTT
ACATTCCGGAGATCAATTGGATCATCATGGTGTTGAGTATCACCATCGTCGGAGG
GTTCCGCAGCACCACTCAAATCGGCCACGCCTACGGGATTGCGGTAGTGGGGGT
GTTTTTCATCTCCACGTGCCTCCTCACGCTCATCATGCTCATGATCTGGCAGACAA
ATATTTTCCTGTGCGCCTTGTTCTTTACCGTCTTCTTTATCATCGAGGGAATTTATT
TCTCAGCGGTGCTCTCCAAGGTGACGCAGGGCGGATGGGTTCCCCTCGTTATCGC
CGCATGCTTCCTCACGATCATGTACTCGTGGAACTTCGGCACCAGGATGAAACGC
TTGTATGAGGTCTCTCATAAGATTTCCTTGGACTGGGTTCTGTCTCTTGGCCATAG
CCTAGGAATCTCTCGAGTTCCGGGAGTCGGGCTCGTATACACTGAGCTTCCGCAG
GGAGTTCCAGCAATATTTCGCCACTTCATCTCGAATCTCCCTGCTATCCACTCCA
CTCTAGTGTTCGTCTGCATCCGCCACATCTCTGTCAGCACCGTCCCCGAAGATGA
GCGAATCCTTATCCGCAGGCTCGGTCCCAGAAACTACCGCATGTTCCGTTGTGCA
GTTCGCTACGGCTACACAGATCATGTGGATGGGGCTGAATCAGACGGCCAGACC
TTTGAAAACATGCTCCTTGCGAGCCTGGAAAGGTTCATCAGAACGGAAGCGGCG
GAAGTCACTCCTGAATCAGGGCTGGCCTCCTCCCATGCCGCCTCTCCTAGCCATC
ACAAATTAGATAGGCCCTGCGAGTCGTCGGTTTCGAACGACTCCTGTGGGTCAG
ACATCGGCGCAAAGACTGTGGATGAGCTGGAAGCCGATCAAGAAGCTTACACCA
ACGAGGAAGTTCTGTTCTTGCAGAAGGCCAGAGAAGCAGGCGTCGTGTACGTGC
TTGGCGACAGTGACATCCACGCCAAGAGCGACTCGTGGTTTCCTAAACGCATCAT
CATCAATAAGATTTACAAGTTTTTGCGACGGAACTGCCGCAACAACACGCTGTAC
TTAAGCATCCCTAAAGACAGGTTGCTGAAGGTGGGCATGGAGTATTACGTCTGA
GAGTTCCAATCCCGTTCCAACGGAGCTCGC Deduced amino acid sequence of PpAKT-2 from *Physcomitrella patens* (SEQ ID NO:6)
METSAVELQMSTDAVHQRETGERPPLEQTAQDEETSREALHADEAAYREKEGPFRR
LSRKLTRPDSLDVESMRVKEMDHAAPVASFSFILKLAYQSIGVVYGDLGTSPLYVYS
STFTSGIKTNDDILGVLCLIIYTIIATPLVKYIFIVLRANDNGEGGTFALYSLICRHVKLS
GAHAQQPTDLNISSYKLETPSTKMARATRIKEALEKSRAWQNVLLLIVLLGPCLVIGD
GSLTPAISVLSAIQGISVNVSGLSPNVSVIITVVVLAALFSLQRFGTHRVAFLFGPAMLA WFFSIGIIGLYNIFRWDPSVFKALNPWYGLNYFIRNKVDAWASLGGIVLCITGSEAMF
ADLGHFTVKSMQVAFTFLVFPSLLCAYIGQASFLMKNQLDDDVAYTFYRSVPKPIYW
PMFGVATCAAIIASQAMISATYSMIRNAMSLGCFPRVTIVHTSKKVHGQIYIPEINWII
MVLSITIVGGFRSTTQIGHAYGIAVVGVFFISTCLLTLIMLMIWQTNIFLCALFFTVFFIIE
GIYFSAVLSKVTQGGWVPLVIAACFLTIMYSWNFGTRMKRLYEVSHKISLDWVLSLG
HSLGISRVPGVGLVYTELPQGVPAIFRHFISNLPAIHSTLVFVCIRHISVSTVPEDERILIR
RLGPRNYRMFRCAVRYGYTDHVDGAESDGQTFENMLLASLERFIRTEAAEVTPESG
LASSHAASPSHHKLDRPCESSVSNDSCGSDIGAKTVDELEADQEAYTNEEVLFLQKA
REAGVVYVLGDSDIHAKSDSWFPKRIIINKIYKFLRRNCRNNTLYLSIPKDRLLKVGM
EYYV*

Nucleotide sequence of the partial PpZT-1 from *Physcomitrella patens* (SEQ ID NO:7)
GCACGAGGCGATACAAGAAGGAGTCTATTTCTCTCCAGCGTTGAGCATTTCTGGG
CACTGCATGTCGCACTGGTTGTCCACATTGTTGCTGATGAAATGATGTCTCCCAC
TTGTAGAAGGTCTGGTTCCGTGCGTGCTCGGGTGACCACAGGAAACTGCGTTGA
AAGGATTGGGAAGATTGCTCGGTTTGTAACGCTGTTATTGATTTTTGCTGTTTGG
ATAGAGCTTGCTGCGGCTCACGGCGGTGCAGCTGATGAAGCAACACCGGAAGAC
GGACCTCCGCCGAACTTGCGGGCGAAGGGCCTGATTCTTGTGAAGGTGTATTGCC
TGATAATCGTGTTTTTTGTGACGCTGTTGGGTGGAATCTCGCCCTACTTCGTTCCA
TGGAACGCTTCGTTTTGGTGCTGGGAACTCAGTATGCCGCAGGTGTATTTCTGA
CGACTGCGTTGCTACATTTCCTGAGCGACGCGCACAACATCTTTCAAGCGCTTAC
TACCAAACAGTATGCGTTTGCGGAGATGCTTGCCATTGCAGGCTATTTGATCACA
CTGTTTGGCGACCTCATCATCCAGCGGCTGATCCTCCGCGGTGCTCGTTCGTCTG
CGCAGCTAGGTTCTTTGGACGGCGAAAAGGATGGGGCTGCGAATTAGATGAGAA
GGGTCGGGCCAGAAGTGAATTGCGACGCTGTTACATCGAGCTTCATTTGGAGAA
TACTCTGTGGTCATCNGGGCCTGTGTTCCACTCTGTCTTGAAGGATGCCACGGGT
CAGGAGAACAGAACATGGAAACTTGGAATACTTCAAAGATTCCCGCTGCGGTTG
CCTGCTGTGCCACGCCTGTGTNATTGGGCCCACACGGTGTGGTCATCCCACGGCG
TTC Nucleotide sequence of the full-length PpZT-1 from *Physcomitrella patens* (SEQ ID NO:8)
TCCACATTGTTGCTGATGAAATGATGTCTCCCACTTGTAGAAGGTCTGGTTCCGT
GCGTGCTCGGGTGACCACAGGAAACTGCGTTGAAAGGATTGGGAAGATTGCTCG
GTTTGTAACGCTGTTATTGATTTTTGCTGTTTGGATAGAGCTTGCTGCGGCTCACG GCGGTGCAGCTGATGAAGCAACACCGGAAGACGGACCTCCGCCGAACTTGCGGG
CGAAGGGCCTGATTCTTGTGAAGGTGTATTGCCTGATAATCGTGTTTTTGTGAC
GCTGTTGGGTGGAATCTCGCCCTACTTCGTTCCATGGAACGCTTCGTTTTTGGTGC
TGGGAACTCAGTATGCCGCAGGTGTATTTCTGACGACTGCGTTGCTACATTTCCT
GAGCGACGCGCACAACATCTTTCAAGCGCTTACTACCAAACAGTATGCGTTTGCG
GAGATGCTTGCCATTGCAGGCTATTTGATCACACTGTTTGGCGACCTCATCATCC
AGCGGCTGATCCTCCGCGGTGCTCGTTCGTCTGCGCAGCTAGGTTCTTTGGACGG
CGAAAAGGATGGGGCTGCGAAATTAGATGAGAAGGGTCGGGCAGAAGTGAATG
CGACGCTGTTACATCGAGCTTCATTTGGAGATACTCTGCTGCTCATTCTGGCCCT
GTGTTTCCACTCTGTCTTTGAAGGCATTGCCATCGGCGTTTCAGTGACGAAGCAG
GACGCATGGAAAGCCTTTTGGACAATTACTCTTCACAAAGTATTCGCAGCCATTG
CCATGGGTATCGCACTCTTGCGCATGCTGCCAAATCGGCCACTCCTGTCGTGCTT
CTGCTATTCTTTTGCATTCGCCATCTCCACTCCAATCGGTATTGCAATCGGCATCA
TCATTGATGCCACTACAGAAGGCGCTGTGGCAGACTGGATTTATGCGATTGCCAT
GGGGTTAGCCACGGGAGTGTTCATCTATGTGGCCATCAACCATCTGCTTGGCAAG
GAGTACATGCCTTCCAAAACTTCTGTGGAACAGCCCTTCAAGAAATTCATTGCCC
TTACCTTGGGAGCTGCAACCATGGCTATTGTCATGATCTGGGATGCTTGACTTTC
TATTTCGCTTGACTTCTATTTCACTTGATAAGAGACAGTTTAACCATCTTCATAGT
GGTGCATGTTCTCAAATATTGTTTCATGTTCGCTGTACAGCGTGCTCAGAGGGAG
AGCATCACTGGTTATTAGGGCTTTTGCGATTCACATCTGAGTGTTGACAACTTAG
GCTCGAAGTACCAAACAAGGTAGCCGGCAGATTGTCGTCAGGTTTTGTGCGTTG
ATGCCTTTCCTGGAATCGAAGCCAATTCCAGTTGATTGAAAGATTAAACAGTTTC
CTCAATCCATTTAATGTATTAAACAAATCCACCTTAATATGGAAAATTTGATCTC
AATGACCAAAGCGGTGATGTTTTTGAGACCAAG Deduced amino acid sequence of PpZT-1 from *Physcomitrella patens* (SEQ ID NO:9)
MMSPTCRRSGSVRARVTTGNCVERIGKIARFVTLLLIFAVWIELAAAHGGAADEATP
EDGPPPNLRAKGLILVKVYCLIIVFFVTLLGGISPYFVPWNASFLVLGTQYAAGVFLTT
ALLHFLSDAHNIFQALTTKQYAFAEMLAIAGYLITLFGDLIIQRLILRGARSSAQLGSLD
GEKDGAAKLDEKGRAEVNATLLHRASFGDTLLLILALCFHSVFEGIAIGVSVTKQDA
WKAFWTITLHKVFAAIAMGIALLRMLPNRPLLSCFCYSFAFAISTPIGIAIGIIIDATTEG
AVADWIYAIAMGLATGVFIYVAINHLLGKEYMPSKTSVEQPFKKFIALTLGAATMAI
VMIWDA*

Nucleotide sequence of the full-length BnAKT-2 from *Brassica napus* (SEQ ID NO:10)

GCAGCTCTTACGACATTCCCTCTTTAAGCACTTTCCTGTCTTCTTGAAAAATCTGT
TTGTATTTGTGAAAAGTTTCACACTTTTATTGTTTTGCTTGTAAAGATCTGAGCTT
TATGAGTTAAAAAAAATGGCGGCAAGAGTAGAAGCAGCAACAATGGGTGGTGG
TGAGATTGATGAAGAGAGTGATGAGAGAGGTAGCATGTGGGATTTGGACCAGAA
GCTTGATCAATCTATGGATGAAGAAGCTGGTCGGCTTAGGAACATGTACAAAGA
AAAGAAATTCTCTGCTCTTCTGCTTCTGCAGCTTTCGTTTCAGAGCCTCGGTGTTG
TGTATGGAGACTTAGGGACTTCTCCTCTCTATGTTTTCTACAATACATTCCCTCAT
GGGATCAAAGATCCTGAAGATACCATTGGAGCTCTATCTCTCATTATCTATTCAC
TCACACTCATCCCTCTCCTCAAATACGTTTTCGTTGTATGTAAAGCCAATGACAA
TGGTCAAGGTGGAACCTTTGCTCTGTATTCATTGCTATGTAGACATGCCAAAGTG
AAAACGATAAAGAACCAGCACCGTACCGATGAAGAGCTTACTACTTACAGCCGG
TCTACCTTTCATGAGCATTCCTTTGCTGCCAAAACCAAAAGGTGGTTAGAAGACA
GGACATCTAGGAAAACAGCTCTTCTTGTTTTGGTTCTTGTTGGTACTTGTATGGTC
ATTGGTGATGGTATCCTTACTCCAGCCATTTCTGTTCTGTCAGCTGCAGGTGGGCT
AAGAGTAAACCTTCCTCATATAAGCAATGGTGTTGTTGTTCTTGTTGCTGTTGTGA
TACTAGTCAGCTTGTTTAGCGTACAGCATTACGGAACAGACCGTGTTGGTTGGCT
TTTCGCTCCCATTGTCTTTCTCTGGTTTCTCTCCATTGCAAGTATCGGTATGTACA
ACATCTGGAAACACGACACCACCGTCTTGAAAGCTTTCTCCCCTGTGTATATCTA
CCGTTATTTCAAAAGAGGAGGTATAGATCGCTGGACATCTCTTGGAGGCATCATG
CTTAGTATAACAGGGATTGAAGCACTCTTCGCTGACCTATCTCACTTTCCTGTTTC
CGCTGTTCAAATAGCTTTCACTGCCATTGTGTTTCCTTGCCTTCTCTTGGCTTATA
GTGGACAAGCTGCCTACATTAGAAACCACCCTCATCACGTGGCTGATGCGTTTTA
CCGTTCCATTCCAGGAAGTGTGTATTGGCCAATGTTCATTATTGCAACTGCTGCA
GCCATTGTTGCAAGCCAAGCCACGATCTCAGCCACGTTCTCTTTGATCAAGCAAG
CTCTAGCACACGGTTGTTTCCCTAGGGTTAAAGTAGTCCACACTTCTAGAAAGTT
TCTTGGTCAGATCTACGTTCCGGACATCAACTGGATCTTGATGATCCTCTGCATC
GCCGTCACGGCTGGATTCAAGAACCAGAGTCAGATAGGTAACGCTTACGGAACA
GCAGTTGTGATCGTCATGCTTGTCACAACTCTGCTTATGACATTGATCATGATCCT
AGTGTGGCGTTGCCATTGGGTTCTTGTTCTTGTGTTCACCGTCCTCTCGCTTGTGG
TTGAATGCACTTACTTCTCAGCCATGCTATTCAAAGTGGACCAAGGAGGTTGGGT
TCCGCTTGTTATCGCTGCAGCGTTTCTCCTCATCATGTCGGTATGGCATTACGGAA
CTTTGAAGAGGTATGAGTTTGAGATGCATAGTAGAGTCTCAATGGCTTGGATTCT
TGGACTTGGGCCTAGCCTTGGGCTTGTTCGTGTTCCTGGTGTTGGGCTTGTCTACA

CTGAGCTAGCTAGTGGAGTCCCTCACATCTTCTCTCACTTCATTACAAACCTACC
GGCTATTCACTCTGTTGTGGTGTTTGTATGCGTCAAGAACCTTCCGGTTTACACTG
TTCCCGAGGAAGAACGGTTCCTTGTTAAAAGGATTGGTCCTAAAAAACTTCCACA
TGTTCCGTTGCGTTGCAAGGTATGGATATGGAGACTTGCACAAGAAAGACGATG
ACTTCAAAAAACGTCTCTTCGAGAGCCTCTTCTTGTTCATACGACTTGAGTCCAT
GATGGAAGGAGGCTGTTCTGATTCAGATGACTACAGCATATGTGGAAGCCAGAA
TCATTTCAAAGAAAAGAACGAGAATGTTGCAACCTTTGATACGTTTGACTCTATA
GAGTCCATAACGCCGGTGAAACGGGTGAGCCACACGGTGACGGCGTCGAGCCAG
ATGAGCGGTGGAGTGGATGAGCTGGAGTTTATAAATAGGTGTAGAGATGCGGGA
GTGGTGCATATAATGGGGAACACGGTGGTTAGAGCGAGGAGGCAAGCGAGGTTC
TACAAGAAGATAGCTATTGATTATGTGTATGCGTTTTTGAGGAAGATTTGTAGAG
AACATAGTGTTATCTTCAATGTTCCTCAGGAGAGCCTTCTGAATGTTGGTCAGAT
CTTCTATGTATAAGATATGAGATATGTGTATGCACTAATGCACGGATGATATTGC
ATGTGTTGTATGTATATCCCTTTTTGAATGTAATGTTGTCTATCATGTTGTCAAAA
AAAAAAAAAAAAA

Deduced amino acid sequence of BnAKT-2 from *Brassica napus* (SEQ ID NO:11)
MAARVEAATMGGGEIDEESDERGSMWDLDQKLDQSMDEEAGRLRNMYKEKKFSA
LLLLQLSFQSLGVVYGDLGTSPLYVFYNTFPHGIKDPEDTIGALSLIIYSLTLIPLLKYVF
VVCKANDNGQGGTFALYSLLCRHAKVKTIKNQHRTDEELTTYSRSTFHEHSFAAKT
KRWLEDRTSRKTALLVLVLVGTCMVIGDGILTPAISVLSAAGGLRVNLPHISNGVVVL
VAVVILVSLFSVQHYGTDRVGWLFAPIVFLWFLSIASIGMYNIWKHDTTVLKAFSPVY
IYRYFKRGGIDRWTSLGGIMLSITGIEALFADLSHFPVSAVQIAFTAIVFPCLLLAYSGQ
AAYIRNHPHHVADAFYRSIPGSVYWPMFIIATAAAIVASQATISATFSLIKQALAHGCF
PRVKVVHTSRKFLGQIYVPDINWILMILCIAVTAGFKNQSQIGNAYGTAVVIVMLVTT
LLMTLIMILVWRCHWVLVLVFTVLSLVVECTYFSAMLFKVDQGGWVPLVIAAAFLLI
MSVWHYGTLKRYEFEMHSRVSMAWILGLGPSLGLVRVPGVGLVYTELASGVPHIFS
HFITNLPAIHSVVVFVCVKNLPVYTVPEEERFLVKRIGPKKLPHVPLRCKVWIWRLAQ
ERR*

Nucleotide sequence of the full-length GmZT-1 from *Glycine max* (SEQ ID NO:12)
CCCATGGCTTCTTCCAACAAAATGAAGATCATCAAGTCAACGTTCCTTGTTTTGT
GCCTCTCAGCCTCGTCGTTCCTCTGTCCAATCAAGGCTCACGGAGGAAGCGGTGA
TTCTCATGACGATGAATCTGATAGCGAAGGTTTGCATTCTCGGGGTCTGATCGTG GTGAAAATATGGTGTTTGATCATCTTCCTTGTGAGCACTTTCGCTGGTGGGGTTTC
TCCTTACTTCTACCGTTGGAACGAGTCTTTTCTTCTTTTGGGGACTCAGTTCGCTG
GTGGGGTTTTCTTGGGAACCTCTTTGATGCATTTCTTGAGCGATTCTGATGAGAC
CTTCCGAGACCTTACCACAAAATCTTACCCTTTTGCCTATATGCTGGCTTCATCTG
GGTACCTTCTCACCATGCTTGGTGACTGTGTTATCACTTATGTCACCAGCAATAG
CAAGAGGGAAGCCAAAGTGGTGGAACTGGAAGGAGGGACAACACCACCCCAAG
AGCATGAGCATGACCAAGCCAGAGATCATTGCGCAGTGGCGGAGACAACAAAC
CCTGTATTATTGAAGACTTCTTCTGTTGGAGACACCATTCTACTCATCCTTGCACT
GTGTTTCCATTCAGTTTTTGAGGGCATTGCAGTTGGAGTTGCAGGTACTAAGGCG
GACGCATGGAGGAACTTATGGACAATATCCTTGCACAAGATATTTGCTGCTATTG
CAATGGGAATTGCTTTGCTAAGGATGTTACCTAAGAGACCCTTTGTAACAACAGC
AGCATATTCATTGGCCTTTGCTGTCTCAAGCCCCATTGGTGTGGGGATTGGCATT
GCCATAAATGCCACAACACAAGGAAGCACCGCAGATTGGATGTTCGCTATAACA
ATGGGTATTGCTTGTGGGGTCTTCATCTATGTTGCTATCAATCATTTAATATCCAA
AGGCTTCAAACCACACAAGACAACACGTTACGACACTCCCTGGTTTAGGTTTGTC
GCCGTGCTTTCTGGTGTTGCTGTTATAGCTGTAGTCATGATCTGGGACTGATCATC
ATGTTTCAATTCCTGTTTTTCTTTGTTCATTAATAATTGTTCTACGAAATTGTGCGT
GTGTGATAATTATGATGAATGTACCATTATATGCTCGCCACAATATTAAACGTTC
GTTTAATATTTTGAATAAAAATTTATAGTCTTTGTTCTTTCAAAAAAAAAAAAAA
AAAA Deduced amino acid sequence of GmZT-1 from *Glycine max* (SEQ ID NO:13)
MASSNKMKIIKSTFLVLCLSASSFLCPIKAHGGSGDSHDDESDSEGLHSRGLIVVKIWC
LIIFLVSTFAGGVSPYFYRWNESFLLLGTQFAGGVFLGTSLMHFLSDSDETFRDLTTKS
YPFAYMLASSGYLLTMLGDCVITYVTSNSKREAKVVELEGGTTPPQEHEHDQARDH
CAVAETTNPVLLKTSSVGDTILLILALCFHSVFEGIAVGVAGTKADAWRNLWTISLHK
IFAAIAMGIALLRMLPKRPFVTTAAYSLAFAVSSPIGVGIGIAINATTQGSTADWMFAI
TMGIACGVFIYVAINHLISKGFKPHKTTRYDTPWFRFVAVLSGVAVIAVVMIWD*

Nucleotide sequence of the full-length GmZT-2 from *Glycine max* (SEQ ID NO:14)
ACATTACCATATTCCAATAAAAAAAAATGTCACCTTCTTTTCGCACATCCCTCTTC
CTCTTCACACTCTCCCTTCTCTTCTTCTTCTCCCTCTCCGTCTCCGCCCACAGCGGC
CACCTCGACGACGACGACGACGACGACGCGGACGCCGGAGGCGACGCCATCCC
CAACCTCCGTGCTCGGTCCTTGATTCTCGCAAAGGTGTGGTGTTTGATCGTTATTT TTTTTGCTACTTTTGTATCGGGCGTTTCCCCCTACATTCTGAAATGGAACGAGGG
GTTCTTAGTTCTGGGGACCCAGTTTGCTGGAGGAGTGTTTCTGGGAACTGCAATG
ATGCATTTTCTCAGCGACGCTAATGAAACCTTCGGGGACTTAACTCGCAAGGAGT
ACCCCTTCGCGTTCATGCTCGCGTGTGCAGGGTACTTGATGACCCTGCTCGCTGA
TGCTGTCATTTCCTCGGTTTTGAAGAATACGGGGCGTGACCAACCGCGTGATGCT
GAGGATGTCCAAGTTCAAGGGGCTGATGTGAGCAAAGTAAGTAACAACAGTGTT
AGATCTCAGTCACAACACCGGAGCCATTCTATTTCTAGCTCTGATCATCATCACT
TAGCAAACCCTGCACTTGGATCTGTCCGTTCGCTTGGAGACACCATTTTATTGAT
TGTTGCCCTTTGTGCACATTCTGTGTTTGAGGGCTTAGCAATTGGAGTTGCTGAG
ACCAAAGCAAATGCATGGAAAGCCTTATGGACAATCTGTCTGCACAAGATATTT
GCAGCCATTGCCATGGGAATTGCTCTCCTCAGAATGATTCCTAACCGTCCCCTTG
TGTCGTGTGCAGCCTATGCTTTTGCTTTTGCCATCTCGAGTCCAATTGGTGTGGCC
ATTGGAATTATATTGGATGCCACAACTCAGGGTCATGTGGCGGATTGGATCTTTG
CCATATCAATGGGTCTGGCTTGTGGAGTATTTATCTATGTATCAGTAAACCATCT
GTTGGCAAAAGGGTACATGCCCCACATACCAACAAAGGTTGACTCAGCCTATTT
CAAGTTTCTTGCCGTGTTGTTGGGTGTGGGAGTGATAGCGGTTGTGATGATTTGG
GACACCTAAGGTTGTTCCAAGATAACTTCTCTTTACAGCATTTGCAGAATCTTTT
CTTTTTCTTTTTTTTATCTTTTTGATAATGAATACGTACATTACAGAAAAAGTTGT
GGTAGTTCCTAGGTCAGATTTGGTATTTGGATATTCTTGTCAGAAATGATTTCGTC
AATCATTTATAAGGTAGAAAAGATGACAGAAATTTGCCTCAAATGATAGAAAAG
ATGAGCATGTATTGAGAATTAAGAGGACTTATAAAAGTCTTGGGAAGAAGGGTA
GTTCACATGGAGGGTAGCCTAAATCATTATAGGCAAAGGGGAACGGAGAAGAA
ATATATACAAAGCTATAGAAATGAATTTATAGATCAATAGTTTGTCTGTAGACAT
GATTTATAATAGAAGCTATGCTGTTATTTAATTCATGTAGCCTATACCACCTTGTG
GGGAAAAAGGTTGGTTGGTGGTGGTGTGTATACTTTATTGATTGAATAATTATTA
TGAGTTTTGTTCGTAATAAAAAAAAAAAAAAAAAAA Deduced amino acid sequence of GmZT-2 from *Glycine max* (SEQ ID NO:15)
MSPSFRTSLFLFTLSLLFFFSLSVSAHSGHLDDDDDDDADAGGDAIPNLRARSLILAKV
WCLIVIFFATFVSGVSPYILKWNEGFLVLGTQFAGGVFLGTAMMHFLSDANETFGDL
TRKEYPFAFMLACAGYLMTLLADAVISSVLKNTGRDQPRDAEDVQVQGADVSKVS
NNSVRSQSQHRSHSISSSDHHHLANPALGSVRSLGDTILLIVALCAHSVFEGLAIGVAE
TKANAWKALWTICLHKIFAAIAMGIALLRMIPNRPLVSCAAYAFAFAISSPIGVAIGIL

DATTQGHVADWIFAISMGLACGVFIYVSVNHLLAKGYMPHIPTKVDSAYFKFLAVLL
GVGVIAVVMIWDT*

Nucleotide sequence of the full-length OsZT-1 from *Oryza sativa* (SEQ ID NO:16)
CGCACCCGTCATCGGTCGAACACCACACCTGCGTCCATGGCGGGAGGCAGGGGA
GCCCGCGCCAGCCTCCACCTCCACCTCGCCTGGCTCTGCGCCTTCGCGACCACCG
CGTGGGCGCATGGCGGTGGCGGCGGCGGGGGCGATTCTGACGCCGACGCCGACG
GCGGCGGCGAGGGGAAGCCGGACCTGCGGGCGCGGGGGCTGGTGGCGGCGAAG
CTGTGGTGCTTGGCGGTGGTGTTCGCCGGGACGCTGGCCGGCGGCGTGTCCCCT
ACTTCATGCGGTGGAACGATGCGTTCCTGGCGCTGGGCACGCAGTTCGCGGGGG
GAGTCTTCCTCGGCACCGCCATGATGCACTTCCTCGCCGACGCCAACGAGACTTT
CGCCGACCTCCTCCCCGGCACCGCCTACCCCTTCGCGTTCATGCTCGCCTGCGCC
GGCTACGTCCTCACCATGCTCGCCGACTGCGCCATCTCCTTCGTCGTCGCCCGCG
GCGGCGGCCGGACCGAACCCGCCGCCGCCGCCGGTGCAGGGCTGGAGGAGGGT
AAGCTGAGCAGCACAAATGGCAACGCCTCTGACCCACCAGCAGCTGATGCGGCG
GCGCAAGACCACTCCGTGGCGTCGATGCTGCGGAACGCGAGCACGCTCGGCGAC
AGCGTGCTGCTCATCGCCGCGCTCTGCTTCCACTCCGTCTTCGAGGGCATCGCCA
TCGGAGTCGCCGAGACGAAGGCTGACGCATGGAAGGCGCTGTGGACGATCAGCC
TGCACAAGATCTTCGCGGCCATCGCCATGGGCATCGCGCTGCTCCGGATGCTGCC
GGACCGGCCGTTCCTCTCCTGCTTCGGCTACGCCTTCGCCTTCGCCGTCTCCAGCC
CCGTCGGCGTCGGCATCGGCATCGTCATCGACGCCACCACGCAGGGCCGGGTGG
CCGACTGGATCTTCGCCGTCTCCATGGGCCTCGCCACCGGCATCTTCATCTACGT
CTCCATCAACCACCTCCTCTCCAAGGGCTACACCCCGCTGAGGCCCGTCGCCGCC
GACACGCCGGCGGGGAGGCTGCTCGCCGTCGTCCTCGGCGTCGCCGTCATCGCC
GTCGTCATGATCTGGGACACCTGATGCCGCTCATGATTTCGGACGTTTGTTGGTT
CTTGCAGGAATGTGTGTGTGTAGTAAGTTCGTCGTGAAATTAGCATGTGTAAAGT
TTGTGCCACTCCAACCAAAGTTTCAGGATTATTTATAGCTTTGAATATATCATCA
ACGCTGGGGCACCAAAAAAAAAAAAAAAAAAAA Deduced amino acid sequence of OsZT-1 from *Oryza sativa* (SEQ ID NO:17)
MAGGRGARASLHLHLAWLCAFATTAWAHGGGGGGDSDADADGGGEGKPDLRA
RGLVAAKLWCLAVVFAGTLAGGVSPYFMRWNDAFLALGTQFAGGVFLGTAMMHF
LADANETFADLLPGTAYPFAFMLACAGYVLTMLADCAISFVVARGGGRTEPAAAAG
AGLEEGKLSSTNGNASDPPAADAAAQDHSVASMLRNASTLGDSVLLIAALCFHSVFE GIAIGVAETKADAWKALWTISLHKIFAAIAMGIALLRMLPDRPFLSCFGYAFAFAVSS
PVGVGIGIVIDATTQGRVADWIFAVSMGLATGIFIYVSINHLLSKGYTPLRPVAADTPA
GRLLAVVLGVAVIAVVMIWDT*

We claim:

1. An isolated nucleic acid, wherein the nucleic acid comprises a polynucleotide selected from the group consisting of: a) a polynucleotide as defined in SEQ ID NO: 5; b) a polynucleotide encoding a polypeptide as defined in SEQ ID NO: 6; c) a polynucleotide having at least 90% sequence identity to SEQ ID NO: 5; and d) a polynucleotide encoding a polypeptide having at least 95% sequence identity to SEQ ID NO: 6; wherein a polypeptide encoded by the polynucleotide, of a)–d) when expressed in a plant confers increased tolerance to the plant against high salinity, drought and low temperature.

2. The nucleic acid of claim 1, wherein the nucleic acid comprises a polynucleotide encoding the polypeptide of SEQ ID NO:6.

3. A vector comprising the nucleic acid of claim 1.

4. A transgenic plant cell transformed with the nucleic acid of claim 1.

5. A transgenic plant comprising the plant cell of claim 4.

6. The plant of claim 5, wherein the plant is a monocot.

7. The plant of claim 5, wherein the plant is a dicot.

8. The plant of claim 5, wherein the plant is selected from the group consisting of maize, wheat, rye, oat, triticale, rice, barley, soybean, peanut, cotton, rapeseed, canola, manihot, pepper, sunflower, tagetes, solanaceous plants, potato, tobacco, eggplant, tomato, Vicia species, pea, alfalfa, coffee, cacao, tea, Salix species, oil palm, coconut, perennial grass and a forage crop plant.

9. A plant seed produced by the plant of claim 5, wherein the plant seed comprises the nucleic acid.

10. The seed of claim 9, wherein the seed is true breeding for increased tolerance to high salinity, drought and low temperature as compared to a wild type variety of the seed.

11. A method of producing a transgenic plant containing a nucleic acid wherein the plant has an increased tolerance to an environmental stress of high salinity, drought or low temperature as compared to a wild type variety of the plant comprising, transforming a plant cell with an expression vector comprising the nucleic acid and regenerating from the plant cell the transgenic plant, wherein the nucleic acid encodes a polypeptide that functions to increase a plant's stress response, and wherein the nucleic acid is selected from the group consisting of: a) a polynucleotide as defined in SEQ ID NO: 5; b) a polynucleotide encoding a polypeptide as defined in SEQ ID NO: 6; c) a polynucleotide encoding a polypeptide having at least 95% sequence identity with the polypeptide as defined in SEQ ID NO: 6; and d) a polynucleotide having at least 90% sequence identity to SEQ ID NO: 5; wherein a polypeptide encoded by the polynucleotide, of a)–d) when expressed in a plant confers increased tolerance to the plant against high salinity, drought and low temperature.

12. The method of claim 11, wherein the plant is a monocot.

13. The method of claim 11, wherein the plant is a dicot.

14. The method of claim 11, wherein the plant is selected from the group consisting of maize, wheat, rye, oat, triticale, rice, barley, soybean, peanut, cotton, rapeseed, canola, manihot, pepper, sunflower, tagetes, solanaceous plants, potato, tobacco, eggplant, tomato, Vicia species, pea, alfalfa, coffee, cacao, tea, Salix species, oil palm, coconut, perennial grass and a forage crop plant.

15. The method of claim 11, wherein the nucleic acid comprises a polynucleotide encoding the polypeptide as defined in SEQ ID NO:6.

16. The method of claim 11, wherein the nucleic acid comprises a polynucleotide encoding a polypeptide having at least 95% sequence identity to the polypeptide as defined in SEQ ID NO:6.

17. The method of claim 11, wherein the plant is transformed with a promoter that directs expression of the nucleic acid, and wherein said promoter is selected from one or more of the group consisting of tissue-preferred, developmentally regulated, and stress-inducible promoter.

18. The nucleic acid of claim 1, wherein the nucleic acid comprises the polynucleotide as defined in SEQ ID NO:5.

19. The nucleic acid of claim 1, wherein the nucleic acid comprises a polynucleotide having at least 90% sequence identity to SEQ ID NO:5.

20. The isolated nucleic acid of claim 1, wherein the nucleic acid comprises a polynucleotide having at least 90% sequence identity to SEQ ID NO: 5.

21. The isolated nucleic acid of claim 1, wherein the nucleic acid encodes a polypeptide having at least 95% sequence identity to SEQ ID NO: 6.

22. A transgenic plant cell transformed with the nucleic acid of claim 21.

23. A transgenic plant comprising the plant cell of claim 22.

24. The plant of claim 23, wherein the plant is a monocot.

25. The plant of claim 23, wherein the plant is a dicot.

26. The plant of claim 23, wherein the plant is selected from the group consisting of maize, wheat, rye, oat, triticale, rice, barley, soybean, peanut, cotton, rapeseed, canola, manihot, pepper, sunflower, tagetes, solanaceous plants, potato, tobacco, eggplant, tomato, Vicia species, pea, alfalfa, coffee, cacao, tea, Salix species, oil palm, coconut, perennial grass and a forage crop plant.

27. A plant seed produced by the plant of claim 23, wherein the plant seed comprises the nucleic acid.

28. The seed of claim 27, wherein the seed is true breeding for an increased tolerance to high salinity, drought and low temperature as compared to a wild type variety of the seed.

29. The method of claim 11, wherein the nucleic acid comprises the polynucleotide of SEQ ID NO:5.

30. The method of claim 11, wherein the nucleic acid comprises a polynucleotide having at least 90% sequence identity to SEQ ID NO:5.

* * * * *